US009546375B2

(12) United States Patent
Couture et al.

(10) Patent No.: US 9,546,375 B2
(45) Date of Patent: *Jan. 17, 2017

(54) INFLUENZA VIRUS IMMUNIZING EPITOPE

(75) Inventors: Manon Couture, Saint-Augustin-de-Desmaures (CA); Louis-Philippe Vezina, Neuville (CA); Nathalie Landry, Saint-Romuald (CA)

(73) Assignee: MEDICAGO INC., Quebec (CA)

( * ) Notice: Subject to any disclaimer, the term of this patent is extended or adjusted under 35 U.S.C. 154(b) by 384 days.

This patent is subject to a terminal disclaimer.

(21) Appl. No.: 13/054,452

(22) PCT Filed: Jul. 15, 2009

(86) PCT No.: PCT/CA2009/001040
§ 371 (c)(1),
(2), (4) Date: Apr. 19, 2011

(87) PCT Pub. No.: WO2010/006452
PCT Pub. Date: Jan. 21, 2010

(65) Prior Publication Data
US 2011/0191915 A1  Aug. 4, 2011

Related U.S. Application Data

(60) Provisional application No. 61/081,811, filed on Jul. 18, 2008.

(51) Int. Cl.
| A61K 39/145 | (2006.01) |
| C12N 15/82 | (2006.01) |
| C12N 15/79 | (2006.01) |
| C12N 15/44 | (2006.01) |
| C12N 15/62 | (2006.01) |
| C07K 16/10 | (2006.01) |
| C12N 7/00 | (2006.01) |
| A61K 39/12 | (2006.01) |
| A61K 39/00 | (2006.01) |

(52) U.S. Cl.
CPC ......... *C12N 15/8257* (2013.01); *A61K 39/12* (2013.01); *A61K 39/145* (2013.01); *C07K 16/1018* (2013.01); *C12N 7/00* (2013.01); *A61K 2039/517* (2013.01); *A61K 2039/5258* (2013.01); *A61K 2039/543* (2013.01); *C12N 2760/16123* (2013.01); *C12N 2760/16134* (2013.01); *C12N 2760/16151* (2013.01); *C12N 2760/16223* (2013.01); *C12N 2760/16234* (2013.01); *C12N 2760/16251* (2013.01)

(58) Field of Classification Search
None
See application file for complete search history.

(56) References Cited

U.S. PATENT DOCUMENTS

| 5,312,746 A | 5/1994 | Longo et al. |
| 5,945,326 A | 8/1999 | Morgan et al. |
| 5,958,422 A | 9/1999 | Lomonossoff |
| 6,042,832 A | 3/2000 | Koprowski et al. |
| 6,287,570 B1 | 9/2001 | Foley |
| 6,489,537 B1 | 12/2002 | Rea et al. |
| 7,125,978 B1 | 10/2006 | Vezina |
| 7,132,291 B2 | 11/2006 | Cardineau et al. |
| 7,763,450 B2 | 7/2010 | Robinson et al. |
| 2001/0006950 A1 | 7/2001 | Punnonen et al. |
| 2004/0002061 A1 | 1/2004 | Kawaoka et al. |
| 2005/0048074 A1* | 3/2005 | Cardineau et al. ........ 424/186.1 |
| 2005/0223430 A1 | 10/2005 | Bakker et al. |
| 2006/0010519 A1 | 1/2006 | Kadowaki |
| 2006/0252132 A1 | 11/2006 | Yang et al. |
| 2006/0253928 A1 | 11/2006 | Bakker et al. |

FOREIGN PATENT DOCUMENTS

| AU | 2008261527 | 8/2014 |
| CA | 2700180 | 12/2008 |
| CA | 2615372 A1 | 1/2009 |
| CA | 2693956 A1 | 1/2009 |
| CA | 2707235 A1 | 6/2009 |
| CA | 2700180 | 10/2011 |
| CA | 2700180 | 6/2012 |
| CA | 2707235 | 6/2012 |
| IL | 203018 C1 | 1/2011 |
| SG | 187500 | 8/2014 |
| WO | 8603224 A1 | 6/1986 |
| WO | 97/20056 A2 | 6/1997 |
| WO | 0129242 A2 | 4/2001 |
| WO | 01/31045 A1 | 5/2001 |

(Continued)

OTHER PUBLICATIONS

Mishin et al (Journal of Virology, 79(19), pp. 12416-12424, 2005; Mishin).*
Pushko et al (Vaccine, 23, pp. 5751-5759, 2005; Pushko; cited on IDS).*
Bright et al (Virology, 308, pp. 270-278, 2003; Bright; cited on IDS).*
Smith (GenBank nucleotide sequence EF541394, published Apr. 21, 2007).*
Spitsin et al (Vaccine, 27, pp. 1289-1292, 2009).*
Lelivelt et al (Plant Molecular Biology, 58, pp. 763-744, 2005).*
Warzecha (Biotechnology and Genetic Engineering Reviews, 25(1), pp. 315-330, 2008).*
International Search Report dated Oct. 8, 2008 (PCT/CA2008/001139).

(Continued)

*Primary Examiner* — Anne Kubelik
*Assistant Examiner* — Stephen Uyeno
(74) *Attorney, Agent, or Firm* — Quarles & Brady LLP

(57) ABSTRACT

A method for synthesizing influenza virus-like particles (VLPs) within a plant or a portion of a plant is provided. The method involves expression of a novel influenza HA protein in plants and its purification The invention is also directed towards a VLP comprising influenza HA protein and plants lipids. The invention is also directed to a nucleic acid encoding improved influenza HA as well as vectors. The VLPs may be used to formulate influenza vaccines, or may be used to enrich existing vaccines.

23 Claims, 29 Drawing Sheets

(56) References Cited

FOREIGN PATENT DOCUMENTS

| WO | 02/57468 A2 | 6/2002 |
|---|---|---|
| WO | 03/078637 A2 | 9/2003 |
| WO | 03078637 A2 | 9/2003 |
| WO | 2004065540 A2 | 8/2004 |
| WO | 2004098533 A2 | 11/2004 |
| WO | 2006119516 A2 | 11/2006 |
| WO | 2007011904 A2 | 1/2007 |
| WO | 2007019094 A2 | 2/2007 |
| WO | 2007047831 A2 | 4/2007 |
| WO | 2007095318 A2 | 8/2007 |
| WO | 2009008573 A1 | 1/2009 |
| WO | 2009009876 A1 | 1/2009 |
| WO | 2010/003225 A1 | 1/2010 |
| ZA | 20111231 | 8/2001 |
| ZA | 2010/00207 | 9/2013 |
| ZA | 2010/05917 | 10/2013 |

OTHER PUBLICATIONS

International Preliminary Report on Patentability dated Oct. 26, 2009 (PCT/CA2008/001139).
International Search Report dated Oct. 7, 2008 (PCT/CA2008/001281).
International Preliminary Report on Patentability dated Nov. 12, 2009 (PCT/CA2008/001281).
International Search Report dated Apr. 30, 2009 (PCT/CA2009/000032).
International Preliminary Report on Patentability dated Jul. 27, 2010 (PCT/CA2009/000032).
International Search Report dated Sep. 11, 2009 (PCT/CA2009/000926).
International Preliminary Report on Patentability dated Nov. 5, 2010 (PCT/CA2009/000926).
Canadian Office Action dated Jan. 26, 2011 (CA 2,693,956).
Canadian Office Action dated Sep. 22, 2011 (CA 2,693,956).
Canadian Office Action dated Jan. 20, 2012 (CA 2,693,956).
Canadian Office Action dated Aug. 13, 2010 (CA 2,700,180).
Canadian Office Action dated Mar. 14, 2011 (CA 2,700,180).
Canadian Office Action dated Feb. 16, 2012 (CA 2,762,042).
Canadian Office Action dated Feb. 13, 2012 (CA 2,700,180).
Canadian Office Action dated Jun. 1, 2011 (CA 2,707,235).
Canadian Office Action dated Oct. 28, 20122 (CA 2,707,235).
Canadian Office Action dated Jun. 28, 2011 (CA 2,730,185).
Canadian Office Action dated Nov. 30, 2011 (CA 2,730,185).
Canadian Office Action dated Apr. 27, 2012 (CA 2,730,185).
Chinese Office Action dated Oct. 9, 2011 (CN 200880103174.3).
Chinese Office Action dated May 10, 2012 (CN 200880103174.3).
Chinese Office Action dated Sep. 27, 2011 (CN 200880107072.9).
Chinese Office Action dated Jan. 21, 2012 (CN 200980109781.5).
Eurasian Office Action dated Dec. 13, 2011 (EA 201000195/28).
Egyptian Office Action dated May 16, 2012 (EG/PCT/1826/2009).
Egyptian Office Action dated Nov. 18, 2011 (EG PCT 1222/2010).
European Search Report dated Sep. 13, 2010 (EP 08783201.1).
European Office Action dated May 26, 2011 (EP 08783201.0).
Examination Report dated Mar. 7, 2011 (EP 09700061.6).
European Search Report dated Dec. 20, 2011 (EP 0979733.6).
European Search Report dated Aug. 9, 2011 (EP 09793741.1).
New Zealand Examination Report dated Oct. 26, 2010 (NZ 581944).
New Zealand Office Action dated Nov. 8, 2010 (NZ 582360).
New Zealand Examination Report dated Mar. 21, 2011 (NZ 587108).
New Zealand Examination Report dated May 4, 2011 (NZ 590351).
New Zealand Examination Report dated Feb. 28, 2012 (NZ 598417).
New Zealand Examination Report dated Apr. 15, 2011 (NZ590144).
Russian Office Action dated Mar. 7, 2012 (RU 2010101024).
Singaporean Office Action dated May 2, 2011 (SG 201000090-9).
Singaporean Certificate of Grant of Patent dated Apr. 30, 2012 (SG 201000090-9).
Singaporean Written Opinion dated Mar. 12, 2012 (SG 201009568-5).
Chandler, Garvin Lee, Influenza Hemagglutinin Expression in Nicotiana tabacum and Nicotiana benthamiana. Masters in Science Thesis, Baylor University, Waco, Texas, 2007, 70 pages.
D'Aoust, et al. Influenza virus-like particles produced by transient expression in Nicotiana benthamiana induce a protective immune response against a lethal viral challenge in mice. Plant Biotechnology Journal vol. 6, 2008, pp. 930-940.
D'Aoust, et al., The production of hemagglutinin-based virus-like particles in plants: a rapid, efficient and safe response to pandemic influenza. Plant Biotech. J. 8:607-619 (2010).
Ferrara, C. et al. Modulation of therapeutic antibody effector functions by glycosylation engineering: influence of Golgi enzyme localization domain and co-expression of heterologous β1, 4-N-acetylglucosaminyltransferase III and Golgi α-mannosidase II. Biotechnol. Bioeng. 93(5), 851-861 (2006).
Galarza, Virus-Like particle (VLP) vaccine conferred complete protection against a lethal influenza virus challenge. Viral Immunity, vol. 18, No. 1, 2005, pp. 244-251.
Frugis, MsJ1, an alfalfa DnaJ-like gene, is tissue specific and transcriptionally regulated during cell cycle. Plant molecular Biology, vol. 40, 1999. pp. 397-408.
Garcea. Virus like particles as vaccines and vessels for the delivery of small molecules. Current Opinion in Biotechnology. vol. 15, 2004. pp. 513-517.
Garten, Genbank accession No. FJ966082.Emergence of a Novel Swine-Origin Influenza A (H1N1) Virus in Humans, N. Engl. J. Med 2009.
Hahn Expression of hemagglutinin-neuraminidase protein of Newcastle disease virus in transgenic tobacco. Plant Biotechnology Reporter, vol. 1, 2007, pp. 85-92.
Hamilton, A., Voinnet, O., Chappell, L. & Baulcombe, D. Two classes of short interfering RNA in RNA silencing. EMBO J. 21, 4671-4679 (2002).
Marozin, S., et al. Antigenic and genetic diversity among swine influenza A H1N1 and H1N2 viruses in Europe. Journal of General Virology, 2002, 83, 735-745.
Mason Expression of Norwalk virus capsid protein in transgenic tobacco and potato and its oral immunogenicity in mice. Proceedigns of the National Academy of Sciences USA, vol. 93, 1996, pp. 5335-5340.
Mena, Rescue of Synthetic Chloramphenicol Acetyltransferase RNA into influenza virus-like particles obtained from recombinant plasmics. Journal of Virology, vol. 70, No. 8, 1996, pp. 5016-5024.
Mett, A plant-produced influenza subunit vaccine protects ferrets against virus challenge. Influenza Other Resp. Viruses 2(1):33-40, 2008.
Musiychuk A launch vector fhr the production of vaccine antigens in plants. Influenza do other respiratory viruses. vol. 1, 2007, pp. 19-25.
Plotkin, Hemagglutinin sequence clusters and the antigenic evolution of influenza a virus. PNAS, vol. 99, No. 9, 2002, pp. 6263-6268.
Pushko, Influenza virus-like particles comprises of the HA,NA and M1 proteins of H9N2 influenza virus induce protective immune responses in BALB/c mice. Vaccine, vol. 23, 2005, pp. 5751-5759.
Sainsbury, Expression of multiple proteins using full-length and deleted versions of cowpea mosaic virus RNA-2. Plant Biotechnology Journal, vol. 6, 2008, pp. 82-921.
Shoji, Plant expressed HA as a seasonal influenza vaccine candidate. Vaccine. vol. 26,2008. pp. 2930-2934.
Sourrouille, C. et al. Down-regulated expression of plant-specific glycoepitopes in alfalfa. Plant Biotechnol J. 6(7), 702-721 (2008).
Staehelin, The plant ER: a dynamic organelle composed of a large number of discrete functional domains. The Plant Journal. vol. 11, No. 6, 1997, pp. 1151-1165.
Toukach, Sharing of worldwide distributed carbohydrate related digital resources: online connection of the bacterial carbohydrate structure database and GLYCOSCIENCES. de Nucleic Acids Research. vol. 35, 2007.

(56) References Cited

OTHER PUBLICATIONS

Treanor, Safety and immunogenicity of a Baculovirus-expressed hamegglutinin influenza vaccine: a randomized control trial. Journal of the American Medicago Association, vol. 297, No. 14, 2007, pp. 1577-1582.
Vaccaro, Plasticity of influenza hemagglutinin fusion peptides and their interaction with lipid bilayers. Biophysical journal. vol. 88, 2005. pp. 25-36.
Van Ree, Ronald, et al. Beta (1,2)-Xylose and alpha (1,3)-fucose residues have a strong contribution in IgE binding to plant glycoallergens. Journal of Biological Chemistry, vol. 275:15, 11451-11458, 2000.
Wilson, Iain, et al., Core alpa 1,3-fucose is a key part of the epitope recognized by antibodies reacting against plant N-linked oligosaccharides and is present in a wide variety of plant extracts. Glycobiology vol. 8:7, 651-661. 1998.
Wydro, M. et al. Optimization of transient Agrobacterium-mediated gene expression system in leaves of *Nicotiana benthamiana*. Acta Biochimica Polonica 53(2), 289-298.
Chatterjee, (*Homo sapiens*) Beta-1,4-galactosyltransferase, GenBank AAA68219, Mar. 13, 2001.
Abe et al., Effect of the Addition of Oligosaccharides on the Biological Activities and Antigenicity of Influenza A/H3N2 Virus Hemagglutinin, Journal of Virology 78:9605-9611, 2004.
Bright et al., Impact of Glycosylation on the Immunogenicity of a DNA-Based Influenza H5 HA Vaccine, Virology 308:270-278, 2003.
Brigneti et al., Viral Pathogenicity Determinants are Suppressors of Transgene Silencing in Nicotiana Benthamiana, The EMBO Journal 17(22):6739-6746, 1998.
Chen et al., Influenza Virus Hemagglutinin and Neuraminidase, But Not the Matrix Protein, are Required for Assembly and Budding of Plasmid-Derived Virus-Like Particles, Journal of Virology 81:7111-7123, 2007.
Chiba et al., Diverse Suppressors of RNA Silencing Enhance Agroinfection by a Viral Replicon, Virology 346:7-14, 2006.
Crawford et al., Baculovirus-Derived Hemagglutinin Vaccines Protect Against Lethal Influenza Infections by Avian H5 and H7 Subtypes, Vaccine 17:2265-2274, 1999.
Gallagher et al., Glycosylation Requirements for Intracellular Transport and Function of the Hemagglutinin of Influenza Virus, Journal of Virology 66(12):7136-7145, 1992.
Gallagher et al., Addition of Carbohydrate Side Chains at Novel Sites on Influenza Virus Hemagglutinin Can Modulate the Folding, Transport, and Activity of the Molecule, Journal of Cell Biology 107(6):2059-2073, 1988.
Gomez-Puertas et al., Efficient Formation of Influenza Virus-Like Particles: Dependence on the Expression Levels of Viral Proteins, Journal of General Virology 80:1635-1645, 1999.
Gomez-Puertas et al., Influenza Virus Matrix Protein is the Major Driving Force in Virus Budding, Journal of Virology 74:11538-11547, 2000.
Grgacic et al., Virus-Like Particles: Passport to Immune Recognition, Methods 40:60-65, 2006.
Ha et al., H5 Avian and H9 Swine Influenza Virus Haemagglutinin Structures: Possible Origin of Influenza Subtypes, The EMBO Journal 21(5):865-875, 2002.
Huang et al., Virus-Like Particle Expression and Assembly in Plants: Hepatitis B and Norwalk Viruses, Vaccine 23:1851-1858, 2005.
Johansson, Immunization with Influenza A Virus Hemagglutinin and Neuraminidase Produced in Recombinant Baculovirus Results in a Balanced and Broadened Immune Response Superior to Conventional Vaccine, Vaccine 17:2073-2080, 1999.
Kendal et al., Laboratory-Based Influenza Surveillance of Influenza Virus Infections, Part B Procedures, Atlanta: CDC; p. B17-B35, 1982.
Kuroda et al., The Oligosaccharides of the Influenza Virus Hemagglutinin Expressed in Insect Cells by a Baculovirus Vector, Virology 174:418-429, 1990.

Latham et al., Formation of Wild-Type and Chimeric Influenza Virus-Like Particles Following Simultaneous Expression of Only Four Structural Proteins, Journal of Virology 75:6154- 6165, 2001.
Mongrand et al., Lipid Rafts in Higher Plant Cells, The Journal of Biological Chemistry 279(35):36277-36286, 2004.
Neumann et al., Plasmid-Driven Formation of Influenza Virus-Like Particles, Journal of Virology 74(1):547-551, 2000.
Olsen et al., Immunogenicity and Efficacy of Baculovirus—Expressed and DNA-Based Equine Influenza Virus Hemagglutinin Vaccines in Mice, Vaccine 15:1149-1156, 1997.
Quan et al., Virus-Like Particle Vaccine Induces Protective Immunity Against Homologous and Heterologous Strains of Influenza Virus, Journal of Virology 81(7):3514-3524, 2007.
Saint-Jore-Dupas et al., From Planta to Pharma with Glycosylation in the Toolbox, Trends in Biotechnology 25(7):317-328, 2007.
Suzuki, Sialobiology of Influenza Molecular Mechanism of Host Range Variation of Influenza Viruses, Biol. Pharm. Bull. 28:399-408, 2005.
Vigerust et al., N-Linked Glycosylation Attenuates H3N2 Influenza Viruses, Journal of Virology 81(16): 8593-8600, 2007.
Wagner et al., Interdependence of Hemagglutinin Glycosylation and Neuraminidase as Regulators of Influenza Virus Growth: A Study by Reverse Genetics, Journal of Virology 74(14):6316-6323, 2000.
Wakefield et al., RNA-Binding Properties of Influenza A Virus Matrix Protein M1, Nucleic Acids Research 17(21):8569-8580, 1989.
Office Action dated Jan. 31, 2013 for U.S. Appl. No. 12/664,567.
Office Action dated Sep. 11, 2013 for U.S. Appl. No. 12/664,567.
Restriction Requirement Office Action dated Aug. 13, 2012.for U.S. Appl. No. 12/669,033.
Office Action dated Oct. 4, 2012 for U.S. Appl. No. 12/669,033.
Restriction Requirement Office Action dated Sep. 27, 2012 for U.S. Appl. No. 12/863,772.
Office Action dated Dec. 14, 2012 for U.S. Appl. No. 12/863,772.
Office Action dated Nov. 25, 2013 for U.S. Appl. No. 13/734,886.
Restriction Requirement Office Action dated Mar. 25, 2013 for U.S. Appl. No. 13/748,531.
Office Action dated Sep. 12, 2013 for U.S. Appl. No. 13/748,531.
Office Action dated Jul. 17, 2013 for U.S. Appl. No. 13/003,570.
Bakker, H. et al., "An antibody produced in tobacco expressing a hybrid beta-1,4-galactosyltransferase is essentially devoid of plant carbohydrate epitopes," Proc. Natl. Acad. Sci. U.S.A. (2006) 103, pp. 7577-7582.
Bakker, H., et al., "Galactose-extended glycans of antibodies produced by transgenic plants," Proc. Nat'l. Acad. Sci. U.S.A. 2001, vol. 98, pp. 2899-2904.
Bright, R.A., et al., "Influenza virus-like particles elicit broader immune responses than whole virion inactivated influenza virus or recombinant hemagglutinin," Vaccine (2007) 25, pp. 3871-3878.
Chubet, R., et al., "Vectors for Expression and Secretion of FLAG Epitope-Tagged Proteins in mammalian Cells," BioTechniques, vol. 20:1 (1991), pp. 136-141.
Daugherty, B. et al., "Isolation and Bacterial Expression of a Murine Alpha Leukocyte Interferon Gene," Journal of Interferon Research, 1984, vol. 4, pp. 635-643.
Elmayan, T. & Vaucheret, H., "Expression of single copies of a strongly expressed 35S transgene can be silenced post-transcriptionally," Plant J. (1996) 9: pp. 787-797.
Essl, D., et al., "The N-terminal 77 amino acids from tobacco N-acetylglucosaminyltransferase I are sufficient to retain a reporter protein in the Golgi apparatus of Nicotiana benthamiana cells," FEBS Letters 453 (1999) pp. 169-173.
Fitchette-Laine, A.C., et al., "Distribution of xylosylation and fucosylation in the plang Golgi apparatus," The Plant Journal (1994), vol. 5:5, pp. 673-682.
Garten, et al., "Antigenic and genetic characteristics of swine-origin 2009 A(H1N1) Influenza viruses circulating in Humans," Science (2009) vol. 325, pp. 197-201.
Garten et al., "Emergence of a Novel Swine-Origin Influenza A (H1N1) Virus in Humans," New England Journal of Medicine, Jun. 2009, vol. 360, No. 25, pp. 197-201.

(56) References Cited

OTHER PUBLICATIONS

Gleba, Y., et al., "Magnifection—a new platform for expressing recombinant vaccines in plants," Vaccine 2005, vol. 23, pp. 2042-2048.
Houston, N., et al., "Phylogenetic Analyses Identify 10 Classes of the Protein Disulfide Isomerase Family in Plants, Including Single-Domain Protein Disulfide Isomerase-Related Proteins," Plant Physiology, 2005, vol. 137, pp. 762-778.
Howard, M., et al., "Sequence Specificity of Aminoglycoside-Induced Stop Codon Readthrough: Potential Implications for Treatment of Duchaaenne Muscular Dystrophy," Annals of Neurology 48:1 (2000), pp. 164-169.
Klopfleisch, R., et al., "Neurotropism of Highly Pathogenic Avian Influenza Virus A/Chicken/Indonesia/2003 (H5N1) in Experimentally Infected Pigeons (*Columbia livia* f. domestica)," Vet Pathol. vol. 43, pp. 463-470, 2006.
Kobayashi, Y. et al., "Chaperones Hsp70 and Hsp40 Suppress Aggregate Formation and Apoptosis in cultured Neuronal Cells Expressing Truncated Androgen Receptor Protein with Expanded Polyglutamine Tract," (The Journal of Biological Chemistry, 275(12), pp. 8772-8778, 2000).
Lerouge, P., et al., "N-Glycoprotein biosynthesis in plants: recent developments and future trends," 1998 Plant Molecular Biology 38, pp. 31-48.
Lelivelt, C., et al., "Stable Plastic Transformation in Lettuce (*Lctuca sativa* L.)," Plant Molecular Biology vol. 58, pp. 763-774, 2005.
Li, Wong-Wei, et al., "Antiviral silencing in animals," FEBS Letters 2005, vol. 579, pp. 5965 to 5973.
Liu, L., et al., "Cowpea mosaic virus-based systems for the production of antigens and antibodies in plants," Vaccine 23 (2005) pp. 1788-1792.
Ma, Julian K-C., et al., "The Production of Recombinant Pharmaceutical Proteins in Plants," Nature 2003, vol. 4, pp. 794-805.
Malissard, M., et al., "Improving the solubility of the catalytic domain of human beta-1,4-galactosyltransferase 1 through rationally designed amino-acid replacements," Eur. J. Biochem 268 (2001), pp. 4352-4358.
Okada, K., et al., "Expression and integration of genes introduced into highly synchronized plant protoplasts," Mol Gen Genet (1986) vol. 205, pp. 398-403.
Palacpac, N.Q., et al., "Stable expression of human beta 1,4-galactosyltransferase in plant cells modifies N-linked glycosylation patterns," Proc. Natl. Acad. Sci. USA, 1999, vol. 96, pp. 4692-4697.
Pwee, K-H. & Gray, J.C., "The pea plastocyanin promoter directs cell-specific but not full light-regulated expression in transgenic tobacco plants," Plant J. (1993) 3, pp. 437-449.
Rivard, D., et al., "An in-built proteinase inhibitor system for the protection of recombinant proteins recovered from transgenic plants," Plant Biotechnology Journal, 4, (2006) pp. 359-368.
Roth, B., et al., "Plant viral suppressors of RNA silencing," Virus Research 2004, vol. 102, pp. 97-108.
Sainsbury, Frank, et al., "Extremely high-level and rapid transient protein production in plants without the use of viral replication," Plant Physiology. (2008) vol. 148, pp. 1212-1218.
Shorrosh, B.S., et al., "Molecular Cloning of a Putative Plant Endomembrane Protein Resembling Vertebrate Protein Disulfide-Isomerase and a Phosphatidylinositol-Specific Phospholipase C", proceedings of the National Academy of Sciences, (Dec. 1, 1991) vol. 88:23, pp. 10941-10945.
Shorrosh, B. S., et al.,"Sequence analysis and developmental expression of an alfalfa protein disulfide isomerase," Plant Molecular Biology, vol. 19, (1992) pp. 319-321.
Strasser, R., et al., "Molecular cloning and characterization of cDNA coding for beta1,2N-acetylglucosaminyltransferase I (GlcNAc-T1) from Nicotiana tabacum," Glycobiology, vol. 9:8, (1999) pp. 779-785.
Takahashi, S., et al., "Metabolic engineering of coenzyme Q by modificaiton of isoprenoid side chain in plant," FEBS Letters 580 (2006), pp. 955-959.
van Rij, R., et al., "The RNA silencing endonuclease Argonaute 2 mediates specific antiviral immunity in *Drosophila melanogaster*," Genes and Development 2006 vol. 20, pp. 2985-2995.
Wang, Weili, "Isolation, Identification and Molecular analysis of the Main of Genes Avian Influenza virus Isolates from Different Hosts," China Doctoral Dissertations Full-text Database, Agricultural Science and Technology (2008).
Warzecha, H., "Biopharmaceuticals from Plants: A multitude of Options for Posttranslational Modifications," Biotechnology and Genetic Engineering Reviews, vol. 25, pp. 315-330, 2008.
Whitelam, G., "The Production of Recombinant Proteins in Plants," J Sci Food Agric., 68, (1995) pp. 1-9.
Office Action dated May 21, 2013 for Australian application No. AU2008278222.
Office Action dated Jun. 13, 2013 for Australian application No. AU 2009202819.
Office Action dated Sep. 6, 2012 for Canadian application No. CA 2,615,372.
Office Action dated Sep. 26, 2013 for Canadian application No. CA 2,615,372.
Office Action dated Oct. 16, 2012 for Canadian application No. CA 2,693,956.
Office Action dated Mar. 1, 2013 for Canadian application No. CA 2,693,956.
Notice of Allowance dated Oct. 2, 2012 for Canadian application No. CA 2,700,180.
Office Action dated Jan. 3, 2014 for Canadian application No. CA 2,700,180.
Office Action dated Sep. 28, 2012 for Canadian application No. CA 2,707,235.
Office Action dated Mar. 1, 2013 for Canadian application No. CA 2,707,235.
Notice of Allowance dated Aug. 14, 2013 for Canadian application No. CA 2,707,235.
Office Action dated Sep. 6, 2012 for Canadian application No. CA 2,730,185.
Office Action dated Feb. 4, 2013 for Canadian application No. CA 2,795,379.
Office Action dated May 13, 2013 for Canadian application No. CA 2,795,379.
Office Action dated Aug. 30, 2013 for Canadian application No. CA 2,795,379.
Office Action dated Nov. 28, 2012 for Chinese application No. CN 200880103174.3.
Office Action dated Nov. 27, 2012 for Chinese application No. CN 200980109781.5.
Office Action dated Jul. 24, 2012 for Chinese application No. CN 200880107072.9.
Office Action dated Feb. 21, 2013 for Chinese application No. CN 200880107072.9.
Office Action dated Jul. 16, 2012 for Chinese application No. CN 200980134868.8.
Office Action dated Jan. 15, 2013 for Chinese application No. CN 200980134868.8.
Office Action dated May 30, 2013 for Chinese application No. CN 200980134868.8.
Office Action dated Mar. 8, 2013 for Chinese application No. CN 200980136376.2.
Office Action dated Oct. 10, 2013 for Chinese application No. CN 200980136376.2.
Notice of Allowance dated Aug. 28, 2012 for Eurasian application No. EA 201001198.
Office Action dated Apr. 24, 2013 for Eurasian application No. EA 201001198.
Office Action dated Dec. 9, 2012 for Egyptian application No. EG PCT1826/2009.
Office Action dated Aug. 27, 2013 for Egyptian application No. EG PCT 61/2010.
European Search Report dated Jul. 1, 2010 for European application No. EP 08772802.8.
Exam Report dated Sep. 14, 2012 for European application No. EP 08772802.8.

(56) References Cited

OTHER PUBLICATIONS

Office Action dated Oct. 26, 2012 for European application No. EP 08783201.0.
Decision to Grant dated May 31, 2013 for European application No. EP 08783201.0.
Decision to Grant dated Aug. 17, 2012 for European application No. EP 09700061.6.
Int'l Search Report dated Feb. 15, 2013 for European application No. EP 12181077.4.
Office Action dated Sep. 18, 2012 for Indonesian application No. ID W-0020102481.
Office Action dated May 10, 2013 for Indonesian application No. ID W-0020102481.
Office Action dated Jun. 12, 2013 for Israeli application No. IL 202568.
Office Action dated Aug. 18, 2013 for Israeli application No. IL 203018.
Office Action dated May 9, 2012 for Israeli application No. IL 206967.
Office Action dated Oct. 25, 2012 for Israeli application No. IL 210215.
Office Action dated Nov. 25, 2012 for Israeli application No. IL 210451.
Office Action dated Jul. 10, 2013 for Israeli application No. IL 224035.
Office Action Jul. 31, 2013 for Japanese application No. JP 2010-511461.
Office Action dated Jul. 17, 2013 for Japanese application No. JP 2010-516334.
Office Action dated Aug. 30, 2013 for Japanese application No. JP 2010-542486.
Office Action dated Dec. 5, 2013 for Mexican application No. MX/a/2010/007962.
Office Action dated Sep. 11, 2013 for Korean application No. KR 10-2010-7000811.
Office Action dated Oct. 16, 2012 for Mexican application No. MX/a/2009/013665.
Office Action dated Mar. 6, 2013 for Mexican application No. MX/a/2010/000525.
Office Action dated Mar. 6, 2013 for Mexican application No. MX/a/2010/007962.
Office Action dated Mar. 6, 2013 for Mexican application No. MX/a/2011/000459.
Office Action dated Sep. 19, 2012 for Mexican application No. MX/a/2011/000657.
Office Action dated May 20, 2013 for Mexican application No. MX/a/2011/000657.
Office Action dated Oct. 29, 2013 for Mexican application No. MX/a/2011/000657.
Exam Report dated Feb. 28, 2012 for New Zealand application No. NZ 598417.
Notice of Acceptance dated Jun. 6, 2013 for New Zealand application No. NZ 598417.
Office Action dated Jun. 27, 2012 for New Zealand application No. NZ 587108.
Office Action dated Jan. 28, 2013 for New Zealand application No. NZ 587108.
Office Action dated Dec. 14, 2012 for Russian application No. RU 2010101024/10.
Office Action dated Apr. 5, 2013 for Russian application No. RU2011105073/10.
Office Action dated Oct. 21, 2013 for Russian application No. 2011105073/10.
Office Action dated Aug. 1, 2013 for Russian application No. RU 2011105885/10 with associate's translation.
Restriction Requirement Office Action dated Oct. 26, 2012 for U.S. Appl. No. 12/664,567.
Mortimer et al. "Setting up a platform for plant-based influenza virus vaccine production in South Africa" BMC Biotechnology 2012, 12:14.
Golovkin et al. "Smallpox subunit vaccine produced in planta confers protection in mice" PNAS, Apr. 17, 2007, pp. 6864-6869, vol. 104, No. 16.
Chen et al. "Influenza Virus Hemagglutinin and Neuraminidase, but Not the Matrix Protein, Are Required for Assembly and Budding of Plasmid-Derived Virus-Like Particles" J. Virology, Jul. 2007, p. 7111-7123, vol. 81, No. 13.
Bertoli, D J., et al., "Transgenic plants and insect cells expressing the coat protein of arabis mosaic virus produce empty virus-like particles," J. Gen Virol. (1991) vol. 72:8, pp. 1801-1809.
Ellis, R.J., "The molecular chaperone concept," Seminars in Cell Biology (1990) (1) pp. 1-9 (Abstract only).
Influenza A virus (A/Caledonia/20/99(H1N1)) hemagglutinin (HA) gene. Genbank Accession No. AY289929, 2003, pp. 1-2, http://www.ncbi.nlm.nih.gov/nuccore/ A Y289929.
McCauley, John W., "Structure and function of the influenza virus genome," Biochemical Journal (1983), vol. 211, pp. 281-294.
Office Action dated Mar. 21, 2013 re AU Application No. 2008261527.
AU Certificate of Grant No. 2008261527 dated Aug. 28, 2014.
Office Action dated Jun. 2, 2014 re CA Application No. 2,730,185.
Decision on Rejection dated Feb. 20, 2014 re CN Application No. 200980134868.8 (English translation only).
Office Action dated Jul. 1, 2014 re CN Application No. 200980136376.2 (with English translation).
Office Action dated Jan. 13, 2014 re CN Application No. 201310021693.8 (English translation only).
Office Action dated Sep. 23, 2014 re CN Application No. 201310021693.8 (with English translation).
Office Action dated Dec. 26, 2013 re EA Application No. 201001198 (with English translation).
Office Action dated Sep. 3, 2014 re EA Application No. 201001198 (English translation only).
Office Action dated Sep. 3, 2014 re EG Application No. 2010010061—PCT 61/2010 (with English translation).
Office Action dated Feb. 6, 2014 re EU Application No. 09797336.6.
Office Action dated Sep. 22, 2014 re ID Application No. W-0020102481 (with English translation).
Office Action dated Jan. 15, 2014 re JP Application No. 2011-516934 (English translation only).
Office Action dated Sep. 3, 2014 re JP Application No. 2010-511461 (with English translation).
Office Action dated Dec. 15, 2013 re JP Application No. 2010-516334 (English translation only).
Office Action dated Aug. 30, 2013 re JP Application No. 2010-542486 (with English translation).
Office Action dated Feb. 13, 2014 re JP Application No. 2011-517725 (English translation only).
Office Action dated Sep. 15, 2014 re MY Application No. PI2010000142 (English translation only).
Office Action dated Jul. 9, 2014 re MX Application No. MX/a/2011/000657.
Office Action Feb. 27, 2014 re RU Application No. 2011105885/10 (with English translation).
SG Certificate of Grant No. 187500 dated Aug. 26, 2014.
Search Report dated May 15, 2014 re SG Application No. 201206648-6 (English translation only). Written Opinion dated May 15, 2014 re SG Application No. 201206648-6 (English translation only).
ZA Letters Patent No. 2010/05917 dated Oct. 20, 2013 (first page only).
Final Office Action dated Mar. 28, 2014 re U.S. Appl. No. 12/664,567.
Final Office Action dated Aug. 21, 2014 re U.S. Appl. No. 12/664,567.
Final Office Action dated Mar. 20, 2014 re U.S. Appl. No. 13/734,886.
Final Office Action dated Dec. 5, 2014 re U.S. Appl. No. 13/734,886.
Final Office Action dated Jun. 18, 2014 re U.S. Appl. No. 13/748,531.

(56) References Cited

OTHER PUBLICATIONS

Final Office Action dated May 8, 2014 re U.S. Appl. No. 13/003,570.
ZA Letters Patent No. 2010/0207 dated Sep. 25, 2013 (first page only).
Garten et al. "Emergence of a Novel Swine-Origin Influenza A (H1N1) Virus in Humans," New England Journal of Medicine, Jun. 2009, vol. 360, No. 25, pp. 2605-2615.
Nuttall. ER-resident chaperone interactions with recombinant antibodies in transgenic plants. Eur. J. Biochem. (2002) vol. 269, pp. 6042-6051.
Sorensen, Hans Peter. Advanced genetic strategies for recombinant protein expression in *Escherichia coli*. Journal of Biotechnology 115 (2005) pp. 113-128.
Wang, Wangxia, et al. Role of plant heat-shock proteins and molecular chaperones in the abiotic stress response. Trends in Plant Science, vol. 9:5, 2004, pp. 244-252.
Yokoyama, Naoaki, et al. Co-expression of human chaperone Hsp70 and Hsdj or Hsp40 co-factor increases solubility of overexpressed target proteins in insect cells. Biochimica et Biophysica Acta 1493 (2000) pp. 119-124.
Exam Report dated Dec. 16, 2014 re AU Application No. 2009270404.
Exam Report dated May 7, 2015 re AU Application No. 2009270404.
Notice of Allowance dated Jun. 1, 2015 re CA Application No. 2,730,185.
Office Action dated Apr. 14, 2015 re CA Application No. 2,730,668.
Notice of Reexam dated Jun. 18, 2014 re CN Application No. 200880103174.3. [English Translation only].
Decision on Reexamination dated Mar. 26, 2015 re CN Application No. 200880103174.3. [English Translation only].
Office Action dated May 26, 2015 re CN Application No. 201310021693.8. [English Translation only].
Office Action dated Mar. 25, 2015 re CN Application No. 200980136376.2. [English Translation only].
Office Action dated Jan. 9, 2015 re ID Application No. W-0020102481. [English Translation included].
Office Action dated Apr. 2, 2015 re ID Application No. W-00200903537. [English Translation included].
Office Action dated Jan. 13, 2015 re JP Application No. 2011-516934. [English Translation included].
Exam Report dated Jul. 29, 2015 re in Application No. 8104/DELNP/2009.
Exam Report dated Aug. 6, 2015 re in Application No. 212/DELNP/2010.
Office Action dated May 27, 2015 re JP Application No. 2014-039035. [English Translation only].
Office Action dated Dec. 22, 2014 re KR Application No. 10-2010-7002538. [English Translation only].
Decision to Grant dated Jul. 20, 2015 re KR Application No. 10-2010-7002538. [English Translation included].
Office Action dated May 21, 2015 re KR Application No. 10-2010-7018343. [English Translation included].
Decision of Grant dated Jan. 23, 2015 re RU Application No. 2011105885/10. [English Translation only].
Office Action dated Jul. 8, 2015 re U.S. Appl. No. 12/664,567.
Office Action dated Jun. 25, 2015 re U.S. Appl. No. 13/734,886.
Office Action dated Jan. 5, 2015 re U.S. Appl. No. 13/748,531.
Final Office Action dated Jun. 23, 2015 re U.S. Appl. No. 13/748,531.
Office Action dated Feb. 11, 2015 re U.S. Appl. No. 13/003,570.
Denis, J. et al. "Immunogenicity of papaya mosaic virus-like particles fused to a hepatitis C virus epitope: Evidence for the critical function of multimerization." Virology 363 (Feb. 2007), pp. 59-68.
Hartl, F. Ulrich. "Molecular chaperones in cellular protein folding." Nature, (Jun. 1996) vol. 381, pp. 571-580.
Helenius, A., et al. "Roles of N-Linked Glycans in the Endoplasmic Reticulum." Annu. Rev. Biochem. 2004, 73: pp. 1019-1049. First published online as a Review in Advance on Mar. 25, 2004.
Genbank Accession AFU70328 Influenza A/Vietnam/1203/04 (H5N1) virus HA protein VN1203-ha-spc-opt.
Search Report dated Jul. 28, 2015 in connection with Singapore Patent Application No. SG 2013053467.
Examination Report dated Aug. 14, 2015 in connection with Singapore Patent Application No. SG 2013053467.
Decision on Rejection dated Dec. 14, 2015 in connection with Chinese Patent Application No. 200980136376.2.
Office Action dated Aug. 12, 2015 in connection with European Patent Application No. 09797336.6.
Intent to Grant dated Feb. 5, 2016 in connection with European Patent Application No. 09797336.6.
Office Action dated Jan. 26, 2015 in connection with Japanese Patent Application No. 2011-517725. [English translation only].
Decision to Grant dated Aug. 17, 2015 in connection with Japanese Patent Application No. 2011-517725. [Japanese only].
Office Action dated Aug. 19, 2015 in connection with Korean Patent Application No. 10-2011-7002827. [English translation only].
Office Action dated Nov. 26, 2015 in connection with Chinese Patent Application No. 201310021693.8. [English translation only].
Office Action dated Oct. 1, 2015 in connection with Eurasian Patent Application No. 201001198. [English translation only].
Notice of Allowability dated Sep. 18, 2015 in connection with Indonesian Patent Application No. W-00201002481. [English translation only].
Certificate of Grant dated May 27, 2015 in connection with Israeli Patent Application No. 203018.
Final Rejection dated Jan. 22, 2016 in connection with Korean Patent Application No. 10-2010-7018343. [English translation only].
Advisory Action dated Nov. 3, 2015 in connection with U.S. Appl. No. 13/734,886.
Non-final Office Action dated Feb. 12, 2016 in connection with U.S. Appl. No. 13/734,886.
Final Office Action dated Oct. 6, 2015 in connection with U.S. Appl. No. 13/748,531.
Final Office Action dated Dec. 2, 2015 in connection with U.S. Appl. No. 13/003,570.
Search Report dated Apr. 6, 2016 in connection with United Arab Emirates Patent Application No. UAE/P/ 00652011.
Decision to Grant dated May 27, 2016 in connection with European Patent Application No. 09797336.5.
Office Action dated Mar. 31, 2016 in connection with Malaysian Patent Application No. PI 2011000210.
GenBank Accession EF541394—Influenza A virus (A/Indonesia/5/05(H5N1)) segment 4 hemagglutinin (HA) gene.
Naito, Tadasuke, et al., "Involvement of Hsp90 in Assembly and Nuclear Import of Influenza Virus RNA Polymerase Subunits" J. Virology, Feb. 2007, vol. 81, No. 3, pp. 1339-1349.
Notice of Grounds for Rejection dated Jun. 2, 2016 in connection with Korean Patent Application No. 10-2010-7018343 [English translation only].
Notice of Allowance dated May 26, 2016 in connection with U.S. Appl. No. 13/748,531.
Intention to Grant dated Mar. 2, 2016 in connection with European Patent Application No. 08772802.8.
Notification of Allowability dated Aug. 5, 2015 in connection with Indonesian Patent Application No. W-00200903537 [English translation only].
Office Action date May 18, 2016 in connection with Egyptian Patent Application No. PCT 61/2010 [English translation only].
Chen, B.J., et al. Influenza virus hemagglutinin and neuraminidase, but not the matrix protein, are required for assembly and budding of plasmid-derived virus-like particles. J. Virol. 81: 13 7111-7123, 2007.
Gomord, V., Chamberlain, P., Jefferis, R. & Faye, L. Biopharmaceutical production in plants: problems, solutions and opportunities. Trends Biotechnol. 23, 559-565 (2005).

(56) References Cited

OTHER PUBLICATIONS

Hull, A. K. et al. Human-derived, plant-produced monoclonal antibody for the treatment of anthrax. Vaccine 23, 2082-2086 (2005).

Johansen, L.K. and Carrington, J.C. Silencing on the spot. Induction and suppression of RNA silencing in the Agrobacterium-mediated transient expression system. Plant Physiology 126(3), 930-938 (2001).

Ko, K. et al. Function and glycosylation of plant-derived antiviral monoclonal antibody. Proc. Natl. Acad. Sci. U.S.A. 100, 8013-8018 (2003).

Ko, K. & Koprowski, H. Plant biopharming of monoclonal antibodies. Virus Res. 111, 93-100 (2005).

Verch, T, Yusibov, V. & Koprowski, H. Expression and assembly of a full-length monoclonal antibody in plants using a plant virus vector. J. Immunol. Methods 220, 69-75 (1998).

* cited by examiner

Potential antigenic domains

Sites and type of glycosylation

Stem
- N11: Complex [A-C]
- N23: Complex and High-mannose [A] Conserved

Head
- N154: Non conserved
- N165: High-mannose [B] Non conserved
- N286: High-mannose [B] Non conserved Stem
- N484: Complex [A-C] Conserved TmD and Cyto. tail
- N543

Figure 1A
Representation of the localisation of glycosylation sites on the structure of a monomer from influenza virus HA H5 A/Indonesia/5/05.

*AGAGGTACCCCGGGCTGGTATATTTATATGTTGTCAAATAACTCAAAAACCATA*
*AAAGTTTAAGTTAGCAAGTGTGTACATTTTTACTTGAACAAAAATATTCACCTAC*
*TACTGTTATAAATCATTATTAAACATTAGAGTAAAGAAATATGGATGATAAGAAC*
*AAGAGTAGTGATATTTTGACAACAATTTTGTTGCAACATTTGAGAAAATTTTGTT*
*GTTCTCTCTTTTCATTGGTCAAAAACAATAGAGAGAGAAAAAGGAAGAGGGAG*
*AATAAAAACATAATGTGAGTATGAGAGAGAAAGTTGTACAAAAGTTGTACCAAA*
*ATAGTTGTACAAATATCATTGAGGAATTTGACAAAAGCTACACAAATAAGGGTT*
*AATTGCTGTAAATAAATAAGGATGACGCATTAGAGAGATGTACCATTAGAGAAT*
*TTTTGGCAAGTCATTAAAAAGAAAGAATAAATTATTTTTAAAATTAAAAGTTGAG*
*TCATTTGATTAAACATGTGATTATTTAATGAATTGATGAAAGAGTTGGATTAAAG*
*TTGTATTAGTAATTAGAATTTGGTGTCAAATTTAATTTGACATTTGATCTTTTCCT*
*ATATATTGCCCCATAGAGTCAGTTAACTCATTTTTATATTTCATAGATCAAATAA*
*GAGAAATAACGGTATATTAATCCCTCCAAAAAAAAAAACGGTATATTTACTAAA*
*AAATCTAAGCCACGTAGGAGGATAACAGGATCCCCGTAGGAGGATAACATCCA*
*ATCCAACCAATCACAACAATCCTGATGAGATAACCCACTTTAAGCCCACGCATC*
*TGTGGCACATCTACATTATCTAAATCACACATTCTTCCACACATCTGAGCCACA*
*CAAAAACCAATCCACATCTTTATCACCCATTCTATAAAAAATCACACTTTGTGAG*
*TCTACACTTTGATTCCCTTCAAACACATACAAAGAGAAGAGACTAATTAATTAAT*
*TAATCATCTTGAGAGAAA*<u>ATGGCGAAAAACGTTGCGATTTTCGGCTTATTGTTT</u>
<u>TCTCTTCTTGTGTTGGTTCCTTCT</u>AGATCT

GAGCTCTAAGTTAAAATGCTTCTTCGTCTCCTATTTATAATATGGTTTGTTATTG
TTAATTTTGTTCTTGTAGAAGAGCTTAATTAATCGTTGTTGTTATGAAATACTATT
TGTATGAGATGAACTGGTGTAATGTAATTCATTTACATAAGTGGAGTCAGAATC
AGAATGTTTCCTCCATAACTAACTAGACATGAAGACCTGCCGCGTACAATTGTC
TTATATTTGAACAACTAAAATTGAACATCTTTTGCCACAACTTTATAAGTGGTTA
ATATAGCTCAAATATATGGTCAAGTTCAATAGATTAATAATGGAAATATCAGTTA
TCGAAATTCATTAACAATCAACTTAACGTTATTAACTACTAATTTTATATCATCCC
CTTTGATAAATGATAGTACA

Figure 3

Antibody Titers against Whole Inactivated Viruses (WIV) after first and second dose.

Hemagglutination-inhibition (HI) antibody titers after first and second dose.

SEQ ID NO. 1. HA0 from H1

AGATCTTCGCTGACACAATATGTATAGGCTACCATGCCAACAACTCAACCGACACTGTTGACA
CAGTACTTGAGAAGAATGTGACAGTGACACACTCTGTCAACCTACTTGAGGACAGTCACAATG
GAAAACTATGTCTACTAAAAGGAATAGCCCCACTACAATTGGGTAATTGCAGCGTTGCCGGAT
GGATCTTAGGAAACCCAGAATGCGAATTACTGATTTCCAAGGAATCATGGTCCTACATTGTAG
AAACACCAAATCCTGAGAATGGAACATGTTACCCAGGGTATTTCGCCGACTATGAGGAACTGA
GGGAGCAATTGAGTTCAGTATCTTCATTTGAGAGATTCGAAATATTCCCCAAAGAAAGCTCAT
GGCCCAACCACACCGTAACCGGAGTATCAGCATCATGCTCCCATAATGGGAAAAGCAGTTTTT
ACAGAAATTTGCTATGGCTGACGGGGAAGAATGGTTTGTACCCAAACCTGAGCAAGTCCTATG
TAAACAACAAAGAGAAAGAAGTCCTTGTACTATGGGGTGTTCATCACCCGCCTAACATAGGGA
ACCAAAGGGCACTCTATCATACAGAAAATGCTTATGTCTCTGTAGTGTCTTCACATTATAGCAG
AAGATTCACCCCAGAAATAGCCAAAAGACCCAAAGTAAGAGATCAGGAAGGAAGAATCAACTA
CTACTGGACTCTGCTGGAACCTGGGGATACAATAATATTTGAGGCAAATGGAAATCTAATAGC
GCCATGGTATGCTTTTGCACTGAGTAGAGGCTTTGGATCAGGAATCATCACCTCAAATGCACC
AATGGATGAATGTGATGCGAAGTGTCAAACACCTCAGGGAGCTATAAACAGCAGTCTTCCTTT
CCAGAATGTACACCCAGTCACAATAGGAGAGTGTCCAAAGTATGTCAGGAGTGCAAAATTAAG
GATGGTTACAGGACTAAGGAACATCCCATCCATTCAATCCAGAGGTTTGTTTGGAGCCATTGC
CGGTTTCATTGAAGGGGGGTGGACTGGAATGGTAGATGGGTGGTATGGTTATCATCATCAGA
ATGAGCAAGGATCTGGCTATGCTGCAGATCAAAAAAGTACACAAAATGCCATTAACGGGATTA
CAAACAAGGTCAATTCTGTAATTGAGAAAATGAACACTCAATTCACAGCTGTGGGCAAAGAGT
TCAACAAATTGGAAAGAAGGATGGAAAACTTAAATAAAAAAGTTGATGATGGGTTTCTAGACAT
TTGGACATATAATGCAGAATTGTTGGTTCTACTGGAAAATGAAAGGACTTTGGATTTCCATGAC
TCCAATGTGAAGAATCTGTATGAGAAAGTAAAAAGCCAATTAAAGAATAATGCCAAAGAAATAG
GAAACGGGTGTTTTGAGTTCTATCACAAGTGTAACAATGAATGCATGGAGAGTGTGAAAAATG
GTACCTATGACTATCCAAAATATTCCGAAGAATCAAAGTTAAACAGGGAGAAAATTGATGGAG
TGAAATTGGAATCAATGGGAGTATACCAGATTCTGGCGATCTACTCAACTGTCGCCAGTTCCC
TGGTTCTTTTGGTCTCCCTGGGGGCAATCAGCTTCTGGATGTGTTCCAATGGGTCTTTGCAGT
GTAGAATATGCATCTAAGAGCTCAGGCCT

Figure 8

SEQ ID NO. 2. subtype H2
>gi|408516|gb|L11132.1|FLADE88HA Influenza A virus (A/herring gull/DE/677/88 (H2N8)) hemagglutinin (HA) gene, complete cds AGCAAAAGCAGGGGTTATACCATAGACAACCAAAGGCAAGACAATGGCCATCATTTATCTAATTCTTCTG
TTCACAGCAGTGAGAGGGACCAAATATGCCAAATTGCATTGGATACCATTCCAACAATTCCACAGAAAAGGTTGACA
CAATCCTAGAGAGAGAAATGTCACTGTCACTCACGCTGAATTCAGCAGCATTCTTGAGAAGACTCACAATGGAAGTT
ATGCAAACTAAATGGAATCCCTCCACTTGAATTAAGGGATTGCAGCATTGCCGGATGGCTCCTTGGGAAT
CCAGAATGTGATATACTTCTAACTGTGCCAGAATGGTCATACATAATGAAAAGAAATCCAAGGAACG
GCTTGTGCTACCCAGGCAGTTTCAATGATTATGAAGAATTGAAGCATCTTATCAGCAGCGTGACACATTT
TGAGAAAGTAAAGATTCTGCCCAGAAATGAATGGACACAGCATACAACAACTGGAGAGTTCACAGGCTTGC
GCAGACTATGGTGGTCCGTCATTCTTCCGGAACATGGGGAACAAGTGTCTGGTTGACAAAGAAAAGGTCGAATTATCCAA
TTGCCAAAAGATCTTACAACAATACAAGTGGGAACAAATGCTGATCATTTGGGGGATACATCAACACTG
TGATGAAAGTGAACAAAGAGCATTGTATCAGAATGTGGGGACCTATGAATGGACAAGACCTAAAGTAGAACCAGAATGGAATTCT
AACAAAGATCATCCCAGAAATGACAACAGACAATAATAATTTGAGAGTACTGGCAATCTAATTGCACCAGAATA
CGTGGACTATCTCTTAGATATATGGGACACGAGGTAGTTCAGGGATCATGAAAAACATTCAGGAAGGAAACTTGAAAACTGCGAG
TGGTTTCAAATATCCAAACGAGGTAGTTCAGGGATCATAAATACAACATTACCCTTCCACAGAAACTTCCACCCACTGACCA
ACCAAGTGCCAAACTCCTTTGGGAGCAATAATAATCGGAAAGATTAGTCTGGTTTTATAGAGGGTGGATGGCAAGAATGGTTGAT
GATTGAGTCAAGGGATTGTTTGGGCAATGACCAGGCATCTGGGTATGCAGCAGACAAAGAATCCACTCAAA
GGTTGGTATGGGTATCATCACAGCAATGACCAGGCATCTGGGTATGCAGCAGACAAAGAATCCACTCAAA
AGGCAATTGATGGAATCACCAACAAGGTAATTCTGTGAAGAAGATGAACACCCAATTCGGAGCTGT
TGGAAAAGAATTCAGTAACTGGAGAGAATGGAGAACTTGAATAAAGATGGAGGACGGATTCTA
GATGTGTGGACATACAATGCCGAGCTCCTAGTTCTCAATGTGAAAATGAGAGGACACTTGACTTTCATGATT
CTAAGTCAAGAATCTATATGATAAGTCAGAATGCAACTGAGAGACAATGCAAAAGAACTAGGGAATGG
ATGTTTTGAATTTTATCACAAAATGTGATGATGAATGCATGAACAGTGAACAGTGGACATATGATTAT
TCCAAGTATGAAGAGGAGTCTAAACTAAACAGGACTGAAATCAAAGGGTTAAATTGAGCAATGATGGGGG
TTTATCAAATCCTTGCCATCTATGCTACAGTAGCAGGTTCCCTGTCAATGCAGTTCCTGTCAATCATGATAGCTGGGAT
TTCTATATGGATGTCTCCAACGGGTCTCTGCAATGCCAATGCAGAATCTGCATATGATCATCAGTCATTTGTAA
TTAAAAACACCCTTGTTTCTACT

Figure 9

SEQ ID No. 3.
subtype H3

>BHB2107299|gb:EF473574|Symbol:HA|Name:hemagglutinin|organism:Influenza A
Virus A/Texas/32/2003|Segment:4|Subtype:H3|Host:Human

CAAAAACTTCCCGGAAATGACAACAGCACGGCAACGCTGTGCCTTGGGCACCATGCAGTACCAAACGGAA

CGATAGTGAAAACAATCACGAATGACCAAATTGAAGTTACTAATGCTACTGAGCTGGTACAGAGTTCCTC

AACAGGTGGAATATGCGACAGTCCTCATCAGATCCTTGATGGAGAAAACTGCACACTAATAGATGCTCTA

TTGGGAGACCCTCAGTGTGATGGCTTCCAAAATAAGAAATGGGACCTTTTTGTTGAACGCAGCAAAGCCT

ACAGCAACTGTTACCCTTATGATGTGCCGGATTATGCCTCCCTTAGGTCACTAGTTGCCTCATCCGGCAC

ACTGGAGTTTAACAATGAAAGCTTCGATTGGACTGGAGTCACTCAGAATGGAACAAGCTCTGCTTGCAAA

AGGAGATCTAATAAAAGTTTCTTTAGTAGATTGAATTGGTTGACCCACTTAAAATACAAATACCCAGCAT

TGAACGTGACTATGCCAAACAATGAAAAATTTGACAAATTGTACATTTGGGGGGTTCACCACCCGGGTAC

GGACAGTGACCAAATCAGCCTATATGCTCAAGCATCAGGAAGAATCACAGTCTCTACCAAAAGAAGCCAA

CAAACTGTAATCCCGAATATCGGATCTAGACCCAGGGTAAGGGATGTCTCCAGCCGAATAAGCATCTATT

GGACAATAGTAAAACCGGGAGACATACTTTTGATTAACAGCACAGGGAATCTAATTGCTCCTCGGGGTTA

CTTCAAAATACGAAGTGGGAAAAGCTCAATAATGAGATCAGATGCACCCATTGGCAAATGCAATTCCGAA

TGCATCACTCCAAATGGAAGCATTCCCAATGACAAACCATTTCAAAATGTAAACAGGATCACATATGGGG

CCTGTCCCAGATATGTTAAGCAAAACACTCTGAAATTGGCAACAGGGATGCGAAATGTACCAGAGAAACA

AACTAGAGGCATATTTGGCGCAATCGCGGGTTTCATAGAAAATGGTTGGGAGGGAATGGTGGACGGTTGG

TACGGTTTCAGGCATCAAAATTCTGAGGGCACAGGA

Figure 10

SEQ ID NO. 4.
subtype H4

>BHB1050162|gb:DQ021859|Symbol:HA|Name:hemagglutinin|Organism:Influenza A Virus A/mallard/MN/33/00|Segment:4|Subtype:H4|Host:Avian

```
ATGCTATCAATCACGATTCTGTTTCTGCTCATAGCAGAGGGTTCCTCTCAGAATTACACAGGGAATCCCG
TGATATGCCTGGGACATCATGCCGTATCCAATGGGACAATGGTGAAAACCCTGACTGATGACCAAGTAGA
AGTTGTCACTGCCCAAGAATTAGTGGAATCGCAACATCTACCGGAGTTGTGTCCTAGCCCTTTAAGATTA
GTAGATGGACAAACTGTGACATCGTCAATGGTGCCTTGGGAGTCCCAGGCTGTGATCACTTGAATGGTG
CAGAATGGGATGTCTTCATAGAACGACCCACTGCTGTGGACACTTGTTATCCATTTGATGTGCCGGATTA
CCAGAGCCTACGGAGTATCCTAGCAACAATGGGAAATTTGAGTTCATTGCTGAGGAATTCCAATGGAAC
ACAGTCAAACAAAATCCGGAGCATGCAAAAGAGCAAAATGTGAATGACTTTTTCAACAGATTGA
ACTGGCTGACCAAATCTGATGGGAGTCATACCCACTTCAACTGACAAAGGTTAACAACGGGGACTA
TGCAAGACTTTACATATGGGAGAGTTCATCATCCTTCAACTGACACAGAACAAACCAACTTGTATAAGAAC
AACCCTGGGAGAGTAACTGTTTCCACCAAAACCAGTCAAACAAGTGTGGTACCAAACATTGGCAGTAGAC
CATGGGTAAGAGGCCAAAGCGGCAGGATTAGCTTCTATTGGACAATTGTGGAGCCAGGAGACCTCATAGT
CTTCAACACCATAGAGGGAATTTAATTGCTCCGAGAGGTCATTACAAGCTTAACAGTCAAAAGAAGAGCACA
ATTCTGAATACTGCAATTCCCATAGGATCTTTGTGTTAGTAAATGTCACACAGATAGGGGTTCAATCTCTA
CAACCAAAACCCTTTCAGAACATCTCAAGAATATCAATTGGGGACTGTCCCAAGTATGTCAAACAGGATC
CTTGAAACTAGCTACAGGAATGAGGAATATCCCTGAGAAAGCAACCAGAGGCCTGTTTGGTGCAATTG
```

Figure 11

SEQ ID NO. 5.
subtype H5

>BHB950029|gb:AF501235|Symbol:HA|Name:hemagglutinin|Organism:Influenza A Virus
A/duck/Shanghai/1/2000|Segment:4|Subtype:H5|Host:Avian ATGGAGAAAATAGTGCTTCTTCTTGCAATAGTCAGTCTTGTTAAAAGTGATCAGATTTGCATTGGTTACC
ATGCAAACAACTCGACAGAGCAGGTTGACACAATAATGGAAAAGAACGTTACTGTTACACATGCCCAAGA
CATACTGGAAAAGACACACAACGGGAAACTCTGCGATCTAGATGGAGTGAAGCCTCTAATTTTGAGAGAT
TGTAGTGTAGCTGGATGGCTCCTCGGAAACCCTATGTGTGACGAATTCATCAATGTGCCGGAATGGTCTT
ACATAGTGGAGAAGGCCAGTCCAGCCAATGACCTCTGTTACCCAGGGGATTTCAACGACTATGAAGAACT
GAAACACCTATTGAGCAGAATAAACCACTTTGAGAAAATTCAGATCATCCCCAAAAGTTCTTGGTCCAAT
CATGAAGCCTCATCAGGGGTGAGCGCAGCATGTCCATACCATGGGAAGCCCTCCTTTTTCAGAAATGTGG
TATGGCTTATCAAAAGAACAGTGCATACCCAACAATAAGAGGAGCTACAATAATACCAACCAAGAAGA
TCTTTTGGTACTGTGGGGGATTCACCATCCTAATGATGCGGCAGAGCAGACAAAGCTCTATCAAAACCCA
ACCACCTATATTTCCGTTGGAACATCAACACTAAACCAGAGATTGGTCCCAAAAATAGCTACTAGATCCA
AAGTAAACGGGCAAAGTGGAAGAATGGAGTTCTTCTGGACAATTTTAAAGCCGAATGATGCCATAAATTT
CGAGAGTAATGGAAATTTCATTGCTCCAGAATATGCATACAAAATTGTCAAGAAAGGGGACTCAGCAATT
ATGAAAAGTGAATTGGAATATGGTAACTGCAACACCAAGTGTCAAACTCCAATGGGGGCGATAAACTCTA
GTATGCCATTCCACAACATACACCCTCTCACAATCGGGGAATGCCCCAAATATGTGAAATCAAACAGATT
AGTCCTTGCGACTGGACTCAGAAATACCCCTCAAAGAGATAGAAGAAGAAAAAGAGAGGACTATTTGGA
GCTATAGCAGGTTTTATAGAGGGAGGATGGCAAGGAATGGTAGATGGTTGCTATGGGTACCACCATAGCA
ATGAGCAGGGGAGTGGATACGCTGCAGACAAAGAATCCACTCAAAAGGCAATAGATGGAGTCACCAATAA
GGTCAACTCGATCATTGACAAAATGAACACTCAGTTTGAGGCCGTTGGAAGGGAATTTAATAACTTAGAA
AGGAGGATAGAAAATTTAAACAAGAAGATGGAAGACGGATTCCTAGATGTCTGGACTTATAATGCTGAAC
TTCTGGTTCTCATGGAAAATGAGAGAACTCTAGACTTTCATGATTCAAATGTCAAGAACCTTTACAACAA
GGTCCGACTACAGCTTAGGGATAATGCAAAGGAGCTGGGTAATGGTTGTTTCGAGTTCTATCACAAATGT
GATAATGAATGTATGGAAAGTGTAAAAAACGGGACGTATGACTACCCGCAGTATTCAGAAGAAGCAAGAC
TAAACAGAGAGGAAATAAGTGGAGTAAAATTGGAATCAATGGGAACTTACCAAATACTGTCAATTTATTC
AACAGTGGCGAGTTCCCTAGCACTGGCAATCATGGTAGCTGGTCTATCTTTATGGATGTGCTCCAATGGG
TCGTTACAATGCAGAATTTGCATTTAA

Figure 12

SEQ ID NO. 6.
subtype H6

>BHB1049778|gb:DQ021667|Symbol:HA|Name:hemagglutinin|Organism:Influenza A Virus A/northern pintail/TX/828189/02|Segment:4|Subtype:H6|Host:Avian

```
ATGATTGCAATCATTGTAATAGCCGATGGCAGCAGCCGGAAAGTCAGACAAGATCTGCATTGGGTATC
ATGCCAACAATTCAACACACAGGTGGATACGATACTTGAGAAGAATGTAACCGTCACACACTCAGTTGA
ATTGCTGGAGAATCAGAAGGAAGAAAGATTCTGCAAGATCTTGAACAAGGCCCCCTCTCGACCTAAAGGGA
TGCACCATAGAGGGTTGGATCTTGGGAATCCCCAAAATGCGATCTGTTGCTTGGTGACCAAAGCTGGTCAT
ATATAGTGGAAAGACCTACTGCCAAAATGGGATATGCTACCCAGGAGCTTTGAATGAGGTAGAGAACT
GAAAGCATTATCGGATCAGGAGAAAAGGGTAGAGAGATTTGAGATGTTTCCCAAAAGCACATGGGCAGG
GTAGACACCAGCAGTGGGGTAACAAAAGCTTGTCCTTATAATAGTGGTTCATCTTTCTACAGAAACCTCC
TATGGATAATAAAGACCAGTCAGCAGCGTATCCAGTCAGTAATTAAGGGAACTTACAGCAACACTGGAAACCA
GCCAATCCTCTATTTCTCGGGTGTGCACCATCCCTGACACCAATGAGCAAATACTCTGTATGGCTCT
GGCGATCGGTATGTTAGGATGGGAACTCGAATTGATTATTACTGGTCTGTTTTAAAACCAGGAGAAACCTTGAA
CCGCTGTGAATGGCCAAAGAGGTCTAATCGCTCCTCCTTGGTATGCATACAAATTGTCAACACAAATAAGGGA
TGTGGAATCTAATGGAAATCTAATCGCTCCTCCTTGGTATGCATACAAATTGTCAACACAAATAAGGGA
GCCGTCTTCAAGTCAATTTACCAATCGAGAATTGCGATGCCACATGCCAGACTATTGCAGGAGTCCTAA
GGACCAATAAACATTTCAGAAATGTGAGCCCTCTGTGGATAGGAGAATGCCCCAAGTATGTGAAAAGTGA
AAGTCTAAGGCTTGCTACTGGACTAAGAAATGTTCCACAGATTGAAACCCAGAGGGCTTTTCGGAGCTATC
```

Figure 13

SEQ ID NO. 7.
subtype H7

>BHB940420|gb:AF071776|Symbol:HA|Name:hemagglutinin precursor|Organism:Influenza A Virus A/chicken/New York/1995|Chromosome:4|Subtype:H7|Host:Avian GACAAAATATGTCTTGGGCACCATGCTGTGGCAAATGGAACAAAAGTGAACACATTAACAGAGAGGGGA
TTGAAGTAGTGAACGCCACAGAGACGGTGGAAACTGCGAATATCAAGAAAATATGTATTCAAGGGAAAG
GCCAACAGATCTGGGACATGTGGACTTCTAGGAACCCTAATAGGACCTCCCCAATGTGATCAATTCCTG
GAGTTTTACTCTGATTTGATAATTGAGCGAAGAGAAGAACCGATGTGTGCTATCCCGGTAAATTCACAA
ATGAAGAATCACTGAGGCAGATCCTTCGAGGGTCAGGAGGAATTGATAAGGAGTCAATGGTTTCACCTA
TAGTGAATAAGAACCAATGGAGCGACAAGTGCCTGCAATTCCCTCAAATGACAAAGTCGTATAGAAATCCCAGAA
AAGTGGTTGCTGTCGAATTCAGACAGTTCATCATCTGGGAGTTCATCATCTGGGATCGGTTAGCGAGCAGAGCAAACTCTATGG
ACAAACCAGCTCTGATAATTGATAACACAAGTCCGGGAGCA
CGGCCACAAGTGAATGGACAATCAGGAGAAATCGATTTTCACTGGCTACTCCTGATCCAATGACACAG
TGACCTTCACTTTCAATGGGCATTCATAGCCCCTGACAGGGCAAGTTTCTTTAGAGGAGAATCACTAGG
AGTCCAGAGTGATGTTCCTCTGAATTCTAGTTGTGTGACAAACATCAACCCTAGAACATGTGGGGAATGCCCTCGGTAGTCAAACAGACAA
AGTTCCCTGCCATTCCAAAACATCAACCCTAGAACATGTGGGGATGCCCCTCGGTATGTCAAACAGACAA
GCCTCCTTTTGGCTACTAGAGAATGAGAAATGTTCCAGAGAATCCAAAGCCCAGAGGCCTTTTTGGAGCAAT
TGCTGGATTCATAGAGAATGGATGGAGGTCTCATCGATGGATGGTTTCAGACATCAAAATGCA
CAAGGGAAGGAACTGCAGCTGACTACAAAAGCACCCAATCTGCAATAGATCAGATCAGGCAAATTGA
ATCGTCTGATTGACAAAAACAAATCAGCAGTTTGAGCTGATAGACAATGAGTTCAATGAGATAGAACAACA
AATAGGAAATGTCATTAATTGGACACATAGATCTTGCGGACTCAGAAATGAACAAACTTATGAGCGTGTTG
GTGGCAATGGAAAATCAGCATACAATAGATCTTGCGGACTCAGAAATGAACAAACTTATGAGCGTGTCA
GAAAACTAAGGAGAGCATAAGGAGAATGCTGAAGAAGATCAACAACACTTATGACCATACCAATACAGAACAGAGTCATTGCAGAT
TCAGTGCATGGAGAGCATAAGGAGAACAACACTTATGACCATACCAATACAGAACAGAGTCATTGCAGAT
AGAATACAGATAGACCCAGTGAAATTGAGTAGTGGATACAAAGACATAATCTTATGTTTAGCTTCGGG
CATCATGTTTCTTCTCTAGCCGTTGTAATGGGATTGGTTTTCATTTGCATAAAGAATGGAAACATGCG
GTGCACCATTTGTATATAA

Figure 14

SEQ ID NO. 8.
subtype H8

>gi|221317|dbj|D90304.1|FLAHAH8N4 Influenza A virus
(A/Turkey/Ontario/6118/68(H8N4)) gene for hemagglutinin precursor, complete
cds ATGGAAAAATTCATCGCAATAGCAACCTTGGCGAGCACAAATGCATACGATAGGATATGCATTGGGTACC
AATCAAACAACTCCACAGACACAGTGAACACTCTCATAGAACAGAATGTACCAGTCACCCAAACAATGGA
GCTCGTGGAAACAGAGAAACATCCCGCTTATTGTAACACTGATTTAGGTGCCCCATTGGAACTGCGAGAC
TGCAAGATTGAGGCAGTAATCTATGGGAACCCCAAGTGTGACATCCATCTGAAGGATCAAGGTTGGTCAT
ACATAGTGGAGAGGCCCAGCGCACCAGAAGGGATGTGTTACCCTGGATCTGTGGAAAATCTAGAAGAACT
GAGGTTTGTCTTCTCCAGTGCTGCATCTTACAAGAGAATAAGACTATTTGACTATTCCAGGTGGAATGTG
ACTAGATCTGGAACGAGTAAAGCATGCAATGCATCAACAGGTGGCCAATCCTTCTATAGGAGCATCAATT
GGTTGACCAAAAAGGAACCAGACACTTATGACTTCAATGAAGGAGCTTATGTTAATAATGAAGATGGAGA
CATCATTTTCTTATGGGGGATCCATCATCCGCCGGACACAAAGAGCAGACAACACTATATAAAAATGCA
AACACTTTGAGTAGTGTTACTACTAACACTATAAACAGAAGCTTTCAACCAAATATTGGTCCCAGACCAT
TAGTAAGAGGACAGCAAGGGAGGATGGATTACTATTGGGGCATTCTGAAAAGAGGGGAGACTCTGAAGAT
CAGGACCAACGGAAATTTAATCGCACCTGAATTTGGCTATCTGCTCAAAGGTGAAAGCTACGGCAGAATA
ATTCAAAATGAGGATATACCCATCGGGAACTGTAACACAAAATGTCAAACATATGCGGGAGCAATCAATA
GCAGCAAACCCTTTCAGAATGCAAGTAGGCATTACATGGGAGAATGTCCCAAATATGTGAAGAAGGCAAG
CTTGCGACTTGCAGTTGGGCTTAGGAATACGCCTTCTGTTGAACCCAGAGGACTGTTTGGAGCCATTGCT
GGTTTCATTGAAGGAGGATGGTCTGGAATGATTGATGGGTGGTATGGATTTCATCACAGCAATTCAGAGG
GAACAGGAATGGCAGCTGACCAGAAATCAACACAAGAAGCCATCGATAAGATCACCAATAAAGTCAACAA
TATAGTTGACAAGATGAACAGGGAGTTTGAAGTTGTGAATCATGAGTTCTCTGAAGTTGAAAAAAGAATA
AACATGATAAACGATAAAATAGATGACCAAATTGAAGATCTTTGGGCTTACAATGCAGAGCTCCTTGTGC
TCTTAGAGAACCAGAAAACGCTAGACGAACATGATTCCAATGTCAAAAACCTTTTTGATGAAGTGAAAAG
GAGACTGTCAGCCAATGCAATAGATGCTGGGAACGGTTGCTTTGACATACTTCACAAATGCGACAATGAG
TGTATGGAAACTATAAAGAACGGAACTTACGATCATAAGGAATATGAAGAGGAGGCTAAACTAGAAAGGA
GCAAGATAAATGGAGTAAAACTAGAAGAGAACACCACTTACAAAATTCTTAGCATTTACAGTACAGTGGC
GGCCAGTCTTTGCTTGGCAATCCTGATTGCTGGAGGTTTAATCCTGGGCATGCAAAATGGATCTTGTAGA
TGCATGTTCTGTATTTGA

Figure 15

SEQ ID NO. 9.
subtype H9
>BHB954830|gb:AM087218|Symbol:HA|Name:hemagglutinin|Organism:Influenza A Virus
A/shoveler/Iran/G54/03|Segment:4|Subtype:H9|Host:Avian ATGGAAACAGTATCACTAATGACTATACTACTAGTAGCAACAGCAAGCAATGCAGACAAAATCTGCATCG
GCCACCAGTCAACAAACTCCACAGAAACTGTGGACACGCTAACAGAAACCAATGTTCCTGTGACACATGC
CAAAGAATTGCTCCACACAGAGCACAATGGAATGCTGTGTGCAACAAATCTGGGACATCCCCTAATCTTA
GACACGTGCACTATTGAAGGACTGATCTATGGTAACCCTTCTTGTGACTTGCTGTTGGGAGGAAGAGAAT
GGTCCTACATCGTCGAAAGGTCATCAGCTGTAAATGGAACGTGTTACCCTGGGAATGTAGAGAACCTAGA
GGAACTCAGGACACTTTTTAGTTCCGCTAGTTCCTACCGAAGAATCCAAATCTTCCCAGACACAATCTGG
AATGTGACTTACACTGGAACAAGCAAAGCATGTTCAGATTCATTCTACAGGAGTATGAGATGGCTGACTC
AAAAAAGCGGGTCTTACCCTGTTCAAGACGCTCAATACACAAATAATATGGGAAAGAGCATTCTTTTCGT
GTGGGGCATACATCACCCACCCACTGAAGCTGCACAGACAAATTTGTACACAAGAACCGACACAACAACA
AGCGTGACAACAGAAGACTTAAATAGGATCTTCAAACCGATGGTAGGGCCAAGGCCCCTTGTCAATGGTC
TGCAGGGAAGAATTAATTATTATTGGTCGGTACTAAAACCAGGCCAGACACTGCGAGTAAGATCCAATGG
GAATCTAATTGCTCCATGGTATGGACACATTCTTTCGGGAGGGAGCCATGGAAGAATCCTGAAGACTGAT
TTAAAAAGTAGTAATTGCGTAGTGCAATGTCAGACTGAAAAAGGCGGCTTAAACAGTACATTGCCGTTCC
ACAATATCAGTAAATATGCATTTGGAAACTGTCCCAAATATGTTAGAGTTAAAAGTCTCAAACTGGCAGT
AGGGTTGAGGAACGTGCCTGCTAGATCAAGTAGAGGACTATTCGGAGCCATAGCTGGATTCATAGAAGGA
GGTTGGCCAGGACTAGTCGCTGGTTGGTATGGTTTCCAGCATTCAAATGATCAAGGGGTTGGTATTGCGG
CAGATAGGGATTCAACTCAAAAGGCAATTGATAGAATAACAACCAAGGTGAATAATATAGTCGACAAAAT
GAACAAACAATATGAAATAATTGATCATGAATTCAGTGAGGTTGAAACTAGGCTCAACATGATCAATAAT
AAGATTGATGACCAAATACAAGACATATGGGCATATAATGCAGAGTTGCTAGTACTACTTGAAAACCAGA
AAACACTCGATGAGCATGACGCAAATGTGAAGA

Figure 16

SEQ ID NO. 10.
subtype H10

>gi|324365|gb|M21647.1|FLAMS84HA Influenza A virus (A/chicken/Germany/N/1949(H10N7)) hemagglutinin precursor, gene, complete cds AGCAAAAGCAGGGGTCACAATGTACAAAGTAGTAGTAATAATTGGCTCCTTGGAGCAGTGAAAGGTCTT
GACAGAATCTGCCTAGGACACCATGGCGGTTGCCAATGAACCATTGTGAAGACCCTTACAAATGAACAAG
AGGAAGTGACCAATGCTACTGAGACGGTAGAGAGCACAATTGAATAAATTGTGTAGAAAGGAAGAAG
CTACAAGGACTTGGGCAATTGTCACCCGTAGGAATGTTGATAGGAACACCTGTTGTGATCCGCACTTG
ACCGGGACCTGGGACACTCTCATTGAGCGAGGAGAATAATGGAAAGTGGAGAATCAGCAAGATGAGCACTGGCTTCACTTA
ATGAAGAGCATTGAGGCAGAAAATAATGGACCACTCAGCTGGGACCATGAAGGCATGCAAAATTTCCCTCAGACAACAAAACACCTATGGAATA
TGGGTCTTCCATCAATGCTAGTGTCAAAGACAGAACAAAGGGACAATTCATCACCCTTCCAGCAGATCAGAACAACTTTGTTCCAGTTGTT
CGGACACAGTCAGTCAGAACATCTCACTATCTATATGGGGAATTCAGTTGAGAGTTGGGCGAATTGACTTTCACTGGACACTAGTACAGCCGGGTG
ATACGGAACTCAGTCAGTCCAGGTCAATGGACAAAGTGGGCGAATTGACTTTCACTGGACACTAGTACAGCCGGGTG
GGGGCAAGACCTCAGGTCAGGTTCATGAGAAGTGGACAAAGTGGGCGAATTGACTTTCACTGGACACTAGTACAGCCGGGTG
ACAACATAACCTTCTCAGACAATCAGAAGCGTTGATAGACAACAGTTGTGACAAATGCTTTTGGAGAGGGGTTCT
TTTGGGAATCAATCAGAAGCTCCCTTTCAACAGAAAATCTGTCAACAGAGAATGTGCCAGAAGTGGTGCAGGGAAGGGGTCTGTTTGG
TGCAATAGCAGGGTTCATAGAAAACGGATGGGAAGGAATGGTACTCAAGCAGCTATTGACCAAATCACAGGGA
AATGCCCAGGGCACAGGTTGATTGGTAACGTTCATTATTGGTAACGTCCAAGCAGCTATTGACCAAATCACAGGGA
AACTGACAGGTTGGTAACGTCATTATTGGTAACGTCGCACACACTGGACCAAAGATTCAATAACCGACATTGGACTTACAACGCAGAG
GCATCAAATTGGTCAATGGACAGAATCAGCACACAGAATGCAGAAGACATCAGAGATGCTAAATCTGTATGAAA
CTATTAGTGCAATGGAGAATCAGACAGAATGCAGAAGACATCAGAGATGCTAAATCTGTATGAAA
GGGTAAGAAAGCAACTCAGACAGAATCAACCCAGTGAAACATATAAGGAACATATCTATGCCCGGGTACAAAGACATCATACTTTGGTTTAGCT
TGATGATTCGTGCATGGAGAGTATAAGGAACATATCTATGCCCGGGTACAAAGACATCATACTTTGGTTTAGCT
CTGAATAGACTGAACATCATGTTGTTCTTCTAGCCGTTCTCTTATGGGTCTTGTTTCTCTGCCTGAAAATGGAAA
TCGGGGAATCATGTTGTTCTTCTAGCCGTTCTCTTATGGGTCTTGTTTCTCTGCCTGAAAATGGAAA
CATGCCGATGCACAATCTGTATTAGTTAAAACACCCTTGTTTCTACT

Figure 17

SEQ ID NO. 11.
subtype H11

>gi|221307|dbj|D90306.1|FLAHAH11N Influenza A virus (A/duck/England/56(H11N6)) gene for hemagglutinin precursor, complete cds ATGGAGAAAACACTGCTATTTGCAGCTATTTTCCTTTGTGTGAAAGCAGATGAGATCTGTATCGGGTATT
TAAGCAACAACTCGACAGACAAAGTTGACACAATAATTGAGAACAATGTCACGGTCACTAGCTCAGTGGA
ACTGGTTGAGACAGAACACACTGGATCATTCTGTTCAATCAATGGAAAACAACCAATAAGCCTTGGAGAT
TGTTCATTGCTGGATGGATATATTAGGAAACCTATGTGTGATGAACTAATTGGAAAGACTTCATGGTCTT
ACATTGTGGAAAAACCCAATCCAACAAATGGAATCTGTTACCCAGGAACTTTAGAGAGTGAAGAAGAACT
AAGACTGAAATTCAGTGGAGTAGGAGTAACCGCTGAGTTTTAGAATTAACAAATTGAAGTATTCACATCAAATGGATGGGTGCT
GTAAATTCAGGATACACCAATCAGGAACATATCCTGTACTGTGCTACACTGAGAAGAGAACCTTTAACACACCAAAGGGAGAGA
TATGGCTGATACTGATTGTTTGGGGACAGTGGTTCAGAGACGGAATTCATCATCTGAGAGATATGTCAAGATCTGTATAAAAGGAC
AGCTCCTATGTGTAGACAGGCCGGACGGATGACATTCTCTAGATATGCTTTGAGATTGTCTCGTTGTGAAATGGGAAACTG
GAGTCAATGCTAATGGGGCGTTCCTAGCTCGAACATTGAATCATGCTCTACCAAATGTCAAACATGTCCTGAAGAAATAACATT
CGAATCTAATGGGGCGTTCCTAGCTCGAACATTGAATCATGCTCTACCAAATGTCAAACATGCTCCAAGATAATAGGGAAACTG
TTCAGGAGCGAACTGAACATTGTTCACAGAAAATGTCCCAGCAATAGCATCGAGAGGCTTGTTGGAGCAATAGCTGGA
ACAAGCTTCCACATGGCAACAGGACCTAGAAATGTCCCAGCAATAGCATCGAGAGGCTTGTTTGGAGCAATAGCTGGA
AAAGCTTGCAACAGGGGATGGCCTGACTGAACAAGGAGTCAACTCAAAAGCAATAGAACATCCAAGGTAAATAACAT
TTCATAGAAGGGGATGGCCTGACTGAACAAGGAGTCAACTCAAAAGCAATAGAACATCCAAGGTAAATAACAT
CAGGCATTGCAGCAGGATGAATACAAACTTTGAGTCTGTGGTTGAACATCTGGTCATATATGCACAGCTTCTCGTTTTAC
CGTTGACAGGATGAATACAAACTTTGAGTCTGTGGTTGAACATCTGGTCATATATGCACAGCTTCTCGTTTTAC
CAATTATCAAAACACGTAGATACACTGGACCTCAAATGTCAGGAACCTCCATGGAACCTCCATGGAAAGTCAGAAGAAT
TTGAAAATGAGAAGACACACTGGACCTCCATGACTCAAATGTCAGGAACCTCCATGGAAAGTCAGAAGAAT
GCTAAGGACAATGCCAAAGATGAGGGGGAACGGATGCTTCACCTTTACCATAAGTGTGACAATAAATGC
ATTGAACGAGTTAGAAACGGAACATAGTGATCATGGGAATTCTAGTGTATAAAATGTCAATTACAGCTGCATTGC
AGATTGAAGGGGTGAAACTTAGATTCTAGTGGGAATGTGTATAAAATGTCAATTACAGCTGCATTGC
AAGCAGTCTTGTATTGGCAGCACTAGATTCTAGTGGGAATGTGTATAAAATGTCAATTACAGCTGCATTGC
AAGCAGTCTTGTATTGGCAGCACTAGATTCTAGTGGGAATGTGTATAAAATGTCAATTACAGCTGCATTGC
AAGCAGTCTTGTATTGGCAGCACTAGATTCTAGTGGGAATGTGTATAAAATGTCAATTACAGCTGCATTGC
AAGCAGTCTTGTATTGGCAGCACTAGATTCTAGTGGGAATGTGTATAAAATGTCAATTACAGCTGCATTGC
TGTACCATTTGCATTTAG

Figure 18

SEQ ID NO. 12.
subtype H12
>gi|221309|dbj|D90307.1|FLAHAH12N Influenza A virus (A/duck/Alberta/60/76(H12N5)) gene for hemagglutinin precursor, complete cds

```
ATGGAAAAATTCATCATTTTGAGTACTGTCTTGGCAGCAAGCTTTGCATATGACAAAATTTGCATTGGAT
ACCAAACAAACAACTCGACTGAAACGGTAAACACACTAAGTGAACAAAACGTTCCGGTGACGCAGGTGGA
AGAACTTGTACATCGTGGGATTGATCCGATCCTGTGTGGAACGGAACTAGGATCACCACTAGTGCTTGAT
GACTGTTCATTAGAGGGTCTAATCCTAGGCAATCCCAAATGTGATCTTTATTTGAATGGCAGGGAATGGT
CATACATAGTAGAGAGGCCCAAAGAGATGGAAGGAGTTTGCTATCCAGGGTCAATTGAAAACCAGGAAGA
GCTAAGATCTCTGTTTTCTTCCATCAAAAAATATGAAAGAGTGAAGATGTTTGATTTCACCAAATGGAAT
GTCACATACACTGGGACCAGCAAGGCCTGCAATAATACATCAAACCAAGGCTCATTCTATAGGAGCATGA
GATGGTTGACCTTAAAATCAGGACAATTTCCAGTCCAAACAGATGAGTACAAGAACACCAGAGATTCAGA
CATTGTATTCACCTGGGCCATTCACCACCCACCAACATCTGATGAACAAGTAAAATTATACAAAAATCCT
GATACTCTCTCTTCAGTCACCACCGTAGAAATCAATAGGAGCTTCAAGCCTAATATAGGGCCAAGACCAC
TCGTGAGAGGACAACAAGGGAGAATGGATTACTACTGGGCTGTTCTTAAACCTGGACAAACAGTCAAAAT
ACAAACCAATGGTAATCTTATTGCACCTGAATATGGTCACTTAATCACAGGGAAATCACATGGCAGGATA
CTCAAGAATAATTTGCCCATGGACAGTGTGTGACTGAATGTCAATTGAACGAGGGTGTAATGAACACAA
GCAAACCTTTCCAGAACACTAGTAAGCACTATATTGGGAAATGCCCCAAATACATACCATCAGGGAGTTT
AAAATTGGCAATAGGGCTCAGGAATGTCCCACAAGTTCAAGATCGGGGGCTCTTTGGAGCAATTGCAGGT
TTCATAGAAGGCGGATGGCCAGGGCTAGTGGCTGGTTGGTACGGATTTCAGCATCAAAATGCGGAGGGGA
CAGGCATAGCTGCAGACAGAGACAGCACCCAAAGGGCAATAGACAATATGCAAAACAAACTCAACAATGT
CATCGACAAAATGAATAAACAATTTGAAGTGGTGAATCATGAGTTTTCAGAAGTGGAAAGCAGAATAAAC
ATGATTAATTCCAAAATTGATGATCAGATAACTGACATATGGGCATACAATGCTGAATTGCTTGTCCTAT
TGGAAAATCAGAAGACATTAGATGAGCATGACGCTAATGTAAGGAATCTACATGATCGGGTCAGAAGAGT
CCTGAGGGAAAATGCAATTGACACAGGAGACGGCTGCTTTGAGATTTTACATAAATGTGACAACAATTGT
ATGGACACGATTAGAAACGGGACATACAATCACAAAGAGTATGAGGAAGAAAGCAAAATCGAACGACAGA
AAGTCAATGGTGTGAAACTTGAGGAGAATTCTACATATAAAATTCTGAGCATCTACAGCAGTGTTGCCTC
AAGCTTAGTTCTACTGCTCATGATTATTGGGGGTTTCATTTTCGGGTGTCAAAATGGAAATGTTCGTTGT
ACTTTCTGTATTTAA
```

Figure 19

SEQ ID NO. 13.
subtype H13
>gi|221311|dbj|D90308.1|FLAHAH13N Influenza A virus
(A/Gull/Maryland/704/77(H13N6)) gene for hemagglutinin precursor, complete cds
ATGGCTCTAAATGTCATTGCAACTTTGACACTTATAAGTGTATGTGTACATGCAGACAGAATATGCGTGG
GGTATCTGAGCACCAATTCATCAGAAAGGGTCGACACGCTCCTTGAAAATGGGGTCCCAGTCACCAGCTC
CATTGATCTGATTGAGACAAACCACACAGGAACATACTGTTCTCTAAATGGAGTCAGTCCAGTGCATTTG
GGAGATTGCAGCTTTGAAGGATGGATTGTAGGAAACCCAGCCTGCACCAGCAACTTTGGGATCAGAGAGT
GGTCATACCTGATTGAGGACCCCGCGGCCCCTCATGGGCTTGCTACCCTGGAGAATTAAACAACAATGG
TGAACTCAGACACTTGTTCAGTGGAATCAGGTCATTCAGTAGAACGGAATTGATCCCACCTACCTCCTGG
GGGGAAGTACTTGACGGTACAACATCTGCTTGCAGAGATAACACGGGAACCAACAGCTTCTATCGAAATT
TAGTTTGGTTTATAAAGAAGAATACTAGATATCCAGTTATCAGTAAGACCTACAACAATACAACGGGAAG
GGATGTTTTAGTTTATGGGGAATACATCACCCAGTGTCTGTGGATGAGACAAAGACTCTGTATGTCAAT
AGTGATCCATACACACTGGTTTCCACCAAGTCTTGGAGCGAGAAATATAAACTAGAAACGGGAGTCCGAC
CTGGCTATAATGGACAGAGGAGCTGGATGAAAATTTATTGGTCTTTGATACATCCAGGGGAGATGATTAC
TTTCGAGAGTAATGGTGGATTTTTAGCCCCAAGATATGGGTACATAATTGAAGAATATGGAAAAGGAAGG
ATTTTCCAGAGTCGCATCAGAATGTCTAGGTGCAACACCAAGTGCCAGACTTCGGTTGGAGGGATAAACA
CAAACAGAACGTTCCAAAACATCGATAAGAATGCTCTTGGTGACTGTCCCAAATACATAAAGTCTGGCCA
ACTCAAGCTAGCCACTGGACTCAGAAATGTGCCAGCTATATCGAATAGAGGATTGTTCGGAGCAATTGCA
GGGTTCATAGAAGGAGGCTGGCCAGGTTTAATCAATGGTTGGTACGGTTTTCAGCATCAAAATGAACAGG
GAACAGGAATAGCTGCAGACAAAGAATCAACACAGAAAGCTATAGACCAGATAACAACCAAAATAAATAA
CATTATTGATAAAATGAATGGGAACTATGATTCAATTAGGGGTGAATTCAATCAAGTTGAGAAGCGTATA
AACATGCTTGCAGACAGAATAGATGATGCCGTGACGGACATTTGGTCATACAATGCCAAACTTCTTGTAT
TGCTGGAAAATGATAAAACTTTAGATATGCATGATGCTAATGTAAAGAATTTACATGAGCAAGTACGAAG
AGAATTGAAGGACAATGCAATTGACGAAGGAAATGGCTGTTTTGAACTCCTTCATAAATGCAATGACTCC
TGCATGGAAACTATAAGAAATGGAACGTATGACCACACTGAGTATGCAGAGGAGTCAAAGTTAAAGAGGC
AAGAAATCGATGGGATCAAACTCAAATCAGAAGACAACGTTTACAAAGCATTATCAATATACAGTTGCAT
TGCAAGTAGTGTTGTACTAGTAGGACTCATACTCTCTTTCATCATGTGGGCCTGTAGTAGTGGGAATTGC
CGATTCAATGTTTGTATATAA

Figure 20

SEQ ID NO. 14.
subtype H14

>gi|324045|gb|M35997.1|FLAH1424 Influenza A/Mallard/Gurjev/263/82
hemagglutinin subtype H14 gene AGCAAAAGCAGGGGAAAATGATTGCACTCATATTGGTTGCACTGGCTCTGAGCCACACTGCTTATTCTCA
GATCACAAATGGGACAACAGGAAACCCCATTATATGCTTGGGGCATCATGCAGTGGAAAACGGCACATCT
GTTAAAACACTAACAGACAATCACGTAGAAGTTGTGTCAGCTAAAGAATTAGTTGAGACGAACCACACTG
ATGAACTGTGCCCAAGCCCCTTGAAGCTTGTCGACGGGCAAGACTGCCACCTCATCAATGGTGCATTGGG
GAGTCCAGGCTGTGACCGTTGCAGGACACCACTTGGGATGTCTTCATTGAAAGGCCCACTGCAGTAGAC
ACATGTATCCATTCGACGTCCCAGATTACCAGAGTCTCAGAAGCATCCTAGCAAGCAGTGGGAGTTTGG
AGTTCATCGCCGAACAATTCACCTGGAATGGTGTCAAAGTTGACGGATCAAGCAGTGCTTGTTTGAGGGG
CGGTCGCAACAGCTTCTTCTCCCGACTAAACTGGCTAACCAAAGCAACAAATGGAAACTATGGACCTATT
AACGTCACTAAAGAAATACGGGCTCTTATGTCAGGCTCTATCTCTGGGAGTGCATCACCCATCAAGCG
ATAATGAGCAAACGGATCTCTACAAGGTGGCAACAGGGAGAGTAACAGTATCTACCCGCTCGGACCAAAT
CAGTATTGTTCCCAATATAGGAAGTAGACCGAGGGTAAGGAATCAGAGCGGCAGGATAAGCATCTACTGG
ACCCTAGTAAACCCAGGGGACTCCATCATTTTCAACAGTATTGGGAATTTGATTGCACCAAGAGGCCACT
ACAAAATAAGCAAATCTACTAAGAGCACAGTGCTTAAAAGTGACAAAAGGATTGGGTCATGCACAAGCCC
TTGCTTAACTGATAAAGGTTCGATCCAAAGTGACAAACCTTTTCAGAATGTATCAAGGATTGCTATAGGA
AACTGCCCGAAATATGTAAAGCAAGGGTCCCTGATGTTAGCAACTGGAATGCGCAACATCCCTGGCAAAC
AGGCAAAGGGCTTATTTGGGGCAATTGCTGGATTCATTGAAAATGGTTGGCAAGGCCTGATTGATGGGTG
GTATGGATTCAGGCACCAAAATGCTGAAGGAACAGGAACTGCTGCAGACCTGAAGTCAACTCAGGCAGCC
ATTGATCAGATAAATGGCAAGCTGAACAGATTGATAGAGAAGACAAATGAAAAATATCACCAAATAGAAA
AGGAATTCGAACAGGTGGAAGGAAGAATACAAGACCTTGAGAAGTACGTTGAGGACACTAAGATTGATTT
GTGGTCATACAATGCTGAATTGCTAGTAGCACTAGAGAATCAGCACACAATAGATGTCACAGACTCCGAA
ATGAACAAGCTTTTTGAAAGAGTAAGAAGGCAATTAAGAGAGAATGCAGAAGATCAAGGCAACGGTTGTT
TCGAGATATTCCATCAGTGTGACAACAATTGTATAGAAAGCATTAGAAACGGAACTTATGACCACAACAT
CTACAGGGATGAAGCCATCAACAATCGAATCAAAATAAATCCTGTCACTTTGACGATGGGGTACAAGGAC
ATAATCCTGTGGATTTCTTTCTCCATGTCATGCTTTGTCTTCGTGGCACTGATTCTGGGATTTGTTCTAT
GGGCTTGTCAAACGGGAATATCCGATGCCAAATCTGTATATAAAGAAAAACACCCTTGTTTCTACTC

Figure 21

SEQ ID NO. 15.
subtype H15

\>gi|1226068|gb|L43916.1|FLAHEMAC Influenza A/duck/Australia/341/83 (H15N8) hemagglutinin mRNA, complete cds

```
AGCAAAAGCAGGGGATACAAAATGAACACTCAAATCATCGTCATTCTAGTCCTCGGACTGTCGATGGTCA
GATCTGACAAGATTTGTCTCGGGCACCATGCCGTAGCAAATGGGACAAAAGTCAACACACTAACTGAGAA
AGGAGTGGAAGTGGTCAATGCCACGGAGACAGTGGAGATTACAGGAATAAATAAAGTGTGCACAAAAGGG
AAGAAAGCGGTGGACTTGGGATCTTGTGGAATACTGGGAACTATCATTGGGCCTCCACAATGTGACTCTC
ATCTTAAATTCAAAGCTGATCTGATAATAGAAAGAAGAAATTCAAGTGACATCTGTTACCCAGGGAAATT
CACTAATGAGGAAGCACTGAGACAAATAATCAGAGAATCTGGTGGAATTGACAAAGAGCCAATGGGATTT
AGATATTCAGGAATAAAAACAGACGGGGCAACCAGTGCGTGTAAGAGAACAGTGTCCTCTTTCTACTCAG
AAATGAAATGGCTTTTATCCAGCAAGGCTAACCAGGTGTTCCCACAACTGAATCAGACATACAGGAACAA
CAGAAAAGAACCAGCCCTAATTGTTTGGGGAGTACATCATTCAAGTTCCTTGGATGAGCAAAATAAGCTA
TATGGAGCTGGGAACAAGCTGATAACAGTAGGAAGCTCAAAATACCAACAATCGTTTTCACCAAGTCCAG
GGGACAGGCCCAAAGTGAATGGTCAGGCCGGGAGGATCGACTTTCATTGGATGCTATTGGACCCAGGGGA
TACAGTCACTTTTACCTTCAATGGTGCATTCATAGCCCCAGATAGAGCCACCTTTCTCCGCTCTAATGCC
CCATCGGGAGTTGAGTACAATGGGAAGTCACTGGGAATACAGAGTGATGCACAAATTGATGAATCATGTG
AAGGGGAATGCTTCTACAGTGGAGGGACAATAAACAGCCCTTTGCCATTTCAAAACATCGATAGTTGGGC
TGTCGGAAGGTGCCCCAGATATGTAAAGCAATCAAGCCTGCCGCTGGCCTTAGGAATGAAAAATGTACCA
GAGAAATACATACTAGGGGACTGTTCGGTGCAATTGCAGGATTCATCGAGAATGGATGGGAAGGACTCA
TTGATGGATGGTATGGATTTAGGCATCAAAATGCACAGGGGCAGGGAACAGCTGCTGACTACAAGAGTAC
TCAGGCTGCAATTGACCAGATAACAGGGAAACTTAATAGATTAATTGAAAAAACCAACACACAGTTTGAA
CTCATAGACAATGAGTTCACTGAAGTGGAGCAGCAGATAGGCAATGTAATAAACTGGACAAGGGACTCCT
TGACTGAGATCTGGTCATACAATGCTGAACTTCTAGTAGCAATGGAAAATCAGCATACAATTGACCTTGC
AGATTCTGAAATGAACAAACTCTATGAGAGTGAGAAGACAGCTAAGGGAGAATGCCGAGGAGGATGGA
ACTGGATGTTTTGAGATTTTCCACCGATGTGACGATCAATGTATGGAGAGCATACGAAATAATACTTACA
ATCACACTGAATATCGACAGGAAGCCTTACAGAATAGGATAATGATCAATCCGGTAAAGCTTAGTGGTGG
GTACAAAGATGTGATACTATGGTTTAGCTTCGGGGCATCATGTGTAATGCTTCTAGCCATTGCTATGGGT
CTTATTTTCATGTGTGTGAAAAACGGGAATCTGCGGTGCACTATCTGTATATAATTATTTGAAAAACACC
CTTGTTTCTACT
```

Figure 22

SEQ ID NO. 16.
subtype H16

\>gi|56425020|gb|AY684891.1| Influenza A virus (A/black-headed gull/Sweden/5/99(H16N3)) hemagglutinin (HA) gene, complete cds

```
AGCAAAAGCAGGGGATATTGTCAAAACAACAGAATGGTGATCAAAGTGCTCTACTTTCTCATCGTATTGT
TAAGTAGGTATTCGAAAGCAGACAAAATATGCATAGGATATCTAAGCAACAACGCCACAGACACAGTAGA
CACACTGACAGAGAACGGAGTTCCAGTGACCAGCTCAGTTGATCTCGTTGAAACAAACCACACAGGAACA
TACTGCTCACTGAATGGAATCAGCCCAATTCATCTTGGTGACTGCAGCTTTGAGGGATGGATCGTAGGAA
ACCCTTCCTGTGCCACCAACATCAACATCAGAGAGTGGTCGTATCTAATTGAGGACCCCAATGCCCCCAA
CAAACTCTGCTTCCCAGGAGAGTTAGATAATAATGGAGAATTACGACATCTCTTCAGCGGAGTGAACTCT
TTTAGCAGAACAGAATTAATAAGTCCCAACAAATGGGGAGACATTCTGGATGGAGTCACCGCTTCTTGCC
GCGATAATGGGGCAAGCAGTTTTTACAGAAATTTGGTCTGGATAGTGAAGAATAAAAATGGAAAATACCC
TGTCATAAAGGGGGATTACAATAACACAACAGGCAGAGATGTTCTAGTACTCTGGGGCATTCACCATCCG
GATACAGAAACAACAGCCATAAACTTGTACGCAAGCAAAAACCCCTACACATTAGTATCAACAAAGGAAT
GGAGCAAAAGATATGAACTAGAAATTGGCACCAGAATAGGTGATGGACAGAGAAGTTGGATGAAACTATA
TTGGCACCTCATGCGCCCTGGAGAGAGGATAATGTTTGAAAGCAACGGGGGCCTTATAGCGCCCAGATAC
GGATACATCATTGAGAAGTACGGTACAGGACGAATTTTCCAAAGTGGAGTGAGAATGGCCAAATGCAACA
CAAAGTGTCAAACATCATTAGGTGGGATAAACACCAACAAAACTTTCCAAAACATAGAGAGAAATGCTCT
TGGAGATTGCCCAAAGTACATAAAGTCTGGACAGCTGAAGCTTGCAACTGGGCTGAGAAATGTCCCATCC
GTTGGTGAAAGAGGTTTGTTTGGTGCAATTGCAGGCTTCATAGAAGGAGGGTGGCCTGGGCTAATTAATG
GATGGTATGGTTTCCAGCATCAGAATGAACAGGGGACTGGCATTGCTGCAGACAAAGCCTCCACTCAGAA
AGCGATAGATGAAATAACAACAAAAATTAACAATATAATAGAGAAGATGAACGGAAACTATGATTCAATA
AGAGGGGAATTCAATCAAGTAGAAAAGAGGATCAACATGCTCGCTGATCGAGTTGATGATGCAGTAACTG
ACATATGGTCGTACAATGCTAAACTTCTTGTACTGCTTGAAAATGGGAGAACATTGGACTTACACGACGC
AAATGTCAGGAACTTACACGATCAGGTCAAGAGAATATTGAAAAGTAATGCTATTGATGAAGGAGATGGT
TGCTTCAATCTTCTTCACAAATGTAATGACTCATGCATGGAAACTATTAGAAATGGGACCTACAATCATG
AAGATTACAGGGAAGAATCACAACTGAAAAGGCAGGAATTGAGGGAATAAAATTGAAGTCTGAAGACAA
TGTGTATAAAGTACTGTCGATTTATAGCTGCATTGCAAGCAGTATTGTGCTGGTAGGTCTCATACTTGCG
TTCATAATGTGGGCATGCAGCAATGGAAATTGCCGGTTTAATGTTTGTATATAGTCGGAAAAAATACCCT
TGTTTCTACT
```

Figure 23

SEQ ID NO. 17.
Sequence "wild type"660
GATCAGATTTGCATTGGTTACCATGCAAACAATTCAACAGAGCAGGTTGACACAATCATGGAA
AAGAACGTTACTGTTACACATGCCCAAGACATACTGGAAAAGACACACAACGGGAAGCTCTGC
GATCTAGATGGAGTGAAGCCTCTAATTTTAAGAGATTGTAGTGTAGCTGGATGGCTCCTCGGG
AACCCAATGTGTGACGAATTCATCAATGTACCGGAATGGTCTTACATAGTGGAGAAGGCCAAT
CCAACCAATGACCTCTGTTACCCAGGGAGTTTCAACGACTATGAAGAACTGAAACACCTATTG
AGCAGAATAAACCATTTTGAGAAAATTCAAATCATCCCCAAAAGTTCTTGGTCCGATCATGAA
GCCTCATCAGGAGTTAGCTCAGCATGTCCATACCTGGGAAGTCCCTCCTTTTTTAGAAATGTGG
TATGGCTTATCAAAAAGAACAGTACATACCCAACAATAAAGAAAAGCTACAATAATACCAACC
AAGAGGATCTTTTGGTACTGTGGGGAATTCACCATCCTAATGATGCGGCAGAGCAGACAAGGC
TATATCAAAACCCAACCACCTATATTTCCATTGGGACATCAACACTAAACCAGAGATTGGTAC
CAAAAATAGCTACTAGATCCAAAGTAAACGGGCAAAGTGGAAGGATGGAGTTCTTCTGGACA
ATTTTAAAACCTAATGATGCAATCAACTTCGAGAGTAATGGAAATTTCATTGCTCCAGAATAT
GCATACAAAATTGTCAAGAAGGGGACTCAGCAATTATGAAAGTGAATTGGAATATGGTAA
CTGCAACACCAAGTGTCAAACTCCAATGGGGCGATAAACTCTAGTATGCCATTCCACAACAT
ACACCCTCTCACCATCGGGGAATGCCCCAAATATGTGAAATCAAACAGATTAGTCCTTGCAAC
AGGGCTCAGAAATAGCCCTCAAAGAGAGAGCAGAAGAAAAAGAGAGGACTATTTGGAGCTA
TAGCAGGTTTTATAGAGGGAGGATGGCAGGGAATGGTAGATGGTTGGTATGGGTACCACCAT
AGCAATGAGCAGGGAGTGGGTACGCTGCAGACAAAGAATCCACTCAAAAGGCAATAGATGG
AGTCACCAATAAGGTCAACTCAATCATTGACAAAATGAACACTCAGTTTGAGGCCGTTGGAAG
GGAATTTAATAACTTAGAAAGGAGAATAGAGAATTTAAACAAGAAGATGGAAGACGGGTTTC
TAGATGTCTGGACTTATAATGCCGAACTTCTGGTTCTCATGGAAAATGAGAGAACTCTAGACT
TTCATGACTCAAATGTTAAGAACCTCTACGACAAGGTCCGACTACAGCTTAGGGATAATGCAA
AGGAGCTGGGTAACGGTTGTTTCGAGTTCTATCACAAATGTGATAATGAATGTATGGAAAGTA
TAAGAAACGGAACGTACAACTATCCGCAGTATTCAGAAGAAGCAAGATTAAAAAGAGAGGAA
ATAAGTGGGGTAAAATTGGAATCAATAGGAACTTACCAAATACTGTCAATTTATTCAACAGTG
GCGAGTTCCCTAGCACTGGCAATCATGATGGCTGGTCTATCTTTATGGATGTGCTCCAATGGAT
CGTTACAATGCAGAATTTGCATT

Figure 24

Plast-443c ( 25 mers) SEQ ID NO. 18
5'- GTATTAGTAATTAGAATTTGGTGTC-3'

Figure 25A

HA5-T156A.r (50-mers) SEQ ID NO. 19
5'-TTGTAGCTTTTCTTTATTGTTGGGTATGCACTGTTCTTTTTGATAAGCCA-3'

Figure 25B

HA5-T167A.c (50-mers) SEQ ID NO. 20
5'-ACCCAACAATAAAGAAAAGCTACAATAATGCCAACCAAGAGGATCTTTTG-3'

Figure 25C

HA5-S288A.r (50 mers) SEQ ID NO. 21
5'-GTGAGAGGGTGTATGTTGTGGAATGGCATAGCAGAGTTTATCGCCCCCAT-3'

Figure 25D

HA5-S288A.c (50 mers) SEQ ID NO. 22
5'-ATGGGGGCGATAAACTCTGCTATGCCATTCCACAACATACACCCTCTCAC-3'

Figure 25E

HA(Ind)-SacI.r (38 mers) SEQ ID NO. 23
5'-ACTTTGAGCTCTTAAATGCAAATTCTGCATTGTAACGA-3'

Figure 25F

SEQ ID NO. 24.
5'-AGTTCCCCGGGCTGGTATATTTATATGTTGTC-3'

Figure 25G

SEQ ID NO. 25.
5'-AATAGAGCTCCATTTTCTCTCAAGATGATTAATTAATTAATTAGTC-3

Figure 25H

SEQ ID NO. 26.
5'-AATAGAGCTCGTTAAAATGCTTCTTCGTCTCCTATTTATAATATGG-3'

Figure 25I

SEQ ID NO. 27.
5'-TTACGAATTCTCCTTCCTAATTGGTGTACTATCATTTATCAAAGGGGA-3'

Figure 25J

SEQ ID NO. 28

AAGCTTATGGAGAAAATAGTGCTTCTTCTTGCAATAGTCAGTCTTGTTAAAAGTGATCAGATTTGCATTGG
TTACCATGCAAACAATTCAACAGAGCAGGTTGACACAATCATGGAAAAGAACGTTACTGTTACACATGCC
CAAGACATACTGGAAAGACACACAACGGAAGCTCTGCGATCTAGATGGAGTGAAGCCTCTAATTTA
AGAGATTGTAGTGTGATGGCTCCTCGGGAACCAATGTGTGACGAATTCATCAATGTACCGGAA
TGGTCTTACATAGTGGAGAAGGCCAATCCAACCAATGACCTCTGTTACCCAGGAGTTTCAACGACTAT
GAAGAACTGAAACACCTATTGAGCAGAATAAACCATTTTGAGAAAATTCAAATCATCCCAAAAGTTCTTG
GTCCGATCATGAAGCCTCATCAGGAGTTAGCTCAGCATGTCCATACCTGGGAAGTCCCTCCTTTTAGA
AATGTGGTATGGCTTATCAAAAGAACAGTACTATACCCAACAATAAAGAAAAGCTACAATAATACCAACCA
AGAGGATCTTTTGTACTGTGGGGAATTCCATTGGGACATCAACCTAAACCAGAGATTGGTACCAAAATAGCTATCA
AACCCAACCACCTATATTCCATTGGGACAAGTGGAAGGATGGAGTTCTTCTGGACAATTTAAAACCTAATGATGCAA
AGATCCAAAGTAAACGGGCAAAGTGGAAGGATGGAGTTCTTCTGGACAATTTAAAACCTAATGATGCAA
TCAACTTCGAGAGTAATGGAAATTTCATTGCTCCAGAATATGCAACACCAAGTGTCAAACTCCAATGGGGCGATA
AGCAATTATGAAAAGTGAATTGGAATATGGTAACTGCAACACCAAGTGTCAAACTCCAATGGGGCGATA
AACTCTAGTATGCCATTCCACACAGGGCTCAGAAATAGCCCTCAAAGAGAGCAGAAGAAAAGAGAGGAC
ACAGATTAGAAAAGTGAATTGGAATATGGTAACTGCAACACCAAGTGTCAAACTCCAATGGGGCGATA
TATTTGGAGCTATAGCAGGTTTTATAGAGGGAGGATGGCAGGAGTAGATGGTTGGTATGGGTACC
ACCATAGCAATGAGCAGGGGAGTGGGTACGCTGCAGAAGAATCCACTCAAAAGGCAATAGATGGA
GTCACCAATAAGGTCAACTCAATCATAGAGAATTAACAAGAAGATGAACACTCAGTTTGAGGCCGTTGGAAGGGAATTTA
ATAACTTAGAAAGGAGAACTTTAAACAAGAAGATGGAAGACGGGTTTCTAGATGTCTGACTTA
TAATGCCGAACTTCTGGTTCTCATGGAAAATGAGAGAACTCTAGACTTTCATGACTCAAATGTTAAGAAC
CTCTACGACAAGGTCCGACTACAGCTTAGGAAGTTATGGAAGTATGCAAAGGAAGCTGGGTAACGGTTGTTTCGAGTTC
TATCACAAATGTGATAATGAAGAAAATAAGAAAACGGAACGTACAACTATCCGCAGTATTCAG
AAGAAGCAAGATTAAAAGAGAGGAAATAAGTGGGTAAAATTGGAATCAATAGGAACTTACCAAATACT
GTCAATTTATTCAACAGTGGCGAGTTCCCTAGCACTGCAATCATGATGGCTGGTGCTGTTATCTTTATGGGATG
TGCTCCAATGGATCGTTACAATGCAGAATTGCATTTAAGAGCTC

Figure 26

SEQ ID No.29.
« Triple Mutant" sequence 680 (modifications with respect to sequence 660 appear in bold-underlined)
GATCAGATTTGCATTGGTTACCATGCAAACAATTCAACAGAGCAGGTTGACA
CAATCATGGAAAAGAACGTTACTGTTACACATGCCCAAGACATACTGGAAAA
GACACACAACGGGAAGCTCTGCGATCTAGATGGAGTGAAGCCTCTAATTTTA
AGAGATTGTAGTGTAGCTGGATGGCTCCTCGGGAACCCAATGTGTGACGAAT
TCATCAATGTACCGGAATGGTCTTACATAGTGGAGAAGGCCAATCCAACCAA
TGACCTCTGTTACCCAGGGAGTTTCAACGACTATGAAGAACTGAAACACCTA
TTGAGCAGAATAAACCATTTTGAGAAAATTCAAATCATCCCCAAAAGTTCTT
GGTCCGATCATGAAGCCTCATCAGGAGTTAGCTCAGCATGTCCATACCTGGG
AAGTCCCTCCTTTTTAGAAATGTGGTATGGCTTATCAAAAGAACAGT<u>GCA</u>T
ACCCAACAATAAAGAAAAGCTACAATAAT<u>GCC</u>AACCAAGAGGATCTTTTGGT
ACTGTGGGGAATTCACCATCCTAATGATGCGGCAGAGCAGACAAGGCTATAT
CAAAACCCAACCACCTATATTTCCATTGGGACATCAACACTAAACCAGAGAT
TGGTACCAAAAATAGCTACTAGATCCAAAGTAAACGGGCAAAGTGGAAGGA
TGGAGTTCTTCTGGACAATTTTAAAACCTAATGATGCAATCAACTTCGAGAGT
AATGGAAATTTCATTGCTCCAGAATATGCATACAAAATTGTCAAGAAAGGGG
ACTCAGCAATTATGAAAAGTGAATTGGAATATGGTAACTGCAACACCAAGTG
TCAAACTCCAATGGGGGCGATAAACTCT<u>GCT</u>ATGCCATTCCACAACATACAC
CCTCTCACCATCGGGGAATGCCCCAAATATGTGAAATCAAACAGATTAGTCC
TTGCAACAGGGCTCAGAAATAGCCCTCAAAGAGAGCAGAAGAAAAAGA
GAGGACTATTTGGAGCTATAGCAGGTTTTATAGAGGGAGGATGGCAGGGAAT
GGTAGATGGTTGGTATGGGTACCACCATAGCAATGAGCAGGGGAGTGGGTAC
GCTGCAGACAAAGAATCCACTCAAAAGGCAATAGATGGAGTCACCAATAAG
GTCAACTCAATCATTGACAAAATGAACACTCAGTTTGAGGCCGTTGGAAGGG
AATTTAATAACTTAGAAAGGAGAATAGAGAATTTAAACAAGAAGATGGAAG
ACGGGTTTCTAGATGTCTGGACTTATAATGCCGAACTTCTGGTTCTCATGGAA
AATGAGAGAACTCTAGACTTTCATGACTCAAATGTTAAGAACCTCTACGACA
AGGTCCGACTACAGCTTAGGGATAATGCAAAGGAGCTGGGTAACGGTTGTTT
CGAGTTCTATCACAAATGTGATAATGAATGTATGGAAAGTATAAGAAACGGA
ACGTACAACTATCCGCAGTATTCAGAAGAAGCAAGATTAAAAAGAGAGGAA
ATAAGTGGGGTAAAATTGGAATCAATAGGAACTTACCAAATACTGTCAATTT
ATTCAACAGTGGCGAGTTCCCTAGCACTGGCAATCATGATGGCTGGTCTATCT
TTATGGATGTGCTCCAATGGATCGTTACAATGCAGAATTTGCATT

Figure 27

SEQ ID NO. 30.

5'-GTATTAGTAATTAGAATTTGGTGTC-3'

Figure 28A

SEQ ID NO. 31.

5'-GCAAGAAGAAGCACTATTTTCTCCATTTTCTCTCAAGATGATTA-3'

Figure 28B

SEQ ID NO. 32.

5'-TTAATCATCTTGAGAGAAAATGGAGAAAATAGTGCTTCTTCTTGC-3'

Figure 28C

SEQ ID NO. 33.

5'-ACTTTGAGCTCTTAAATGCAAATTCTGCATTGTAACGA-3'

Figure 28D

SEQ ID NO.34

Amino acid sequence of H5 from A/Vietnam/1194/04

DQICIGYHANNSTEQVDTIMEKNVTVTHAQDILEKTHNGKLCDLDGVKPLILRDC
SVAGWLLGNPMCDEFINVPEWSYIVEKANPVNDLCYPGDFNDYEELKHLLSRIN
HFEKIQIIPKSSWSSHEASLGVSSACPYQGKSSFFRNVVWLIKKNSTYPTIKRSYNN
TNQEDLLVLWGIHHPNDAAEQTKLYQNPTTYISVGTSTLNQRLVPRIATRSKVNG
QSGRMEFFWTILKPNDAINFESNGNFIAPEYAYKIVKKGDSTIMKSELEYGNCNTK
CQTPMGAINSSMPFHNIHPLTIGECPKYVKSNRLVLATGLRNSPQRERRRKKRGLF
GAIAGFIEGGWQGMVDGWYGYHHSNEQGSGYAADKESTQKAIDGVTNKVNSII
DKMNTQFEAVGREFNNLERRIENLNKKMEDGFLDVWTYNAELLVLMENERTLD
FHDSNVKNLYDKVRLQLRDNAKELGNGCFEFYHKCDNECMESVRNGTYDYPQY
SEEARLKREEISGVKLESIGIYQILSIYSTVASSLALAIMVAGLSLWMCSNGSLQCRI
CI

Figure 29

SEQ ID NO.35
Nucleotide sequence of a gene coding for HA from strain B/Florida/4/2006

ATGAAGGCAATAATTGTACTACTCATGGTAGTAACATCCAATGCAGATCGAA
TCTGCACTGGAATAACATCTTCAAACTCACCTCATGTGGTCAAAACAGCCACT
CAAGGGGAGGTCAATGTGACTGGTGTGATACCACTAACAACAACACCAACAA
AATCTTATTTTGCAAATCTCAAAGGAACAAGGACCAGAGGGAAACTATGCCC
AGACTGTCTCAACTGCACAGATCTGGATGTGGCTTTGGGCAGACCAATGTGT
GTGGGGACCACACCTTCGGCGAAGGCTTCAATACTCCACGAAGTCAAACCTG
TTACATCCGGGTGCTTTCCTATAATGCACGACAGAACAAAAATCAGGCAACT
ACCCAATCTTCTCAGAGGATATGAAAATATCAGGCTATCAACCCAAAACGTC
ATCGATGCGGAAAAGGCACCAGGAGGACCCTACAGACTTGGAACCTCAGGA
TCTTGCCCTAACGCTACCAGTAAGAGCGGATTTTTCGCAACAATGGCTTGGGC
TGTCCCAAAGGACAACAACAAAATGCAACGAACCCACTAACAGTAGAAGT
ACCATACATTTGTACAGAAGGGGAAGACCAAATCACTGTTTGGGGGTTCCAT
TCAGATAACAAAACCCAAATGAAGAACCTCTATGGAGACTCAAATCCTCAAA
AGTTCACCTCATCTGCTAATGGAGTAACCACACACTATGTTTCTCAGATTGGC
AGCTTCCCAGATCAAACAGAAGACGGAGGACTACCACAAAGCGGCAGGATT
GTTGTTGATTACATGATGCAAAAACCTGGGAAAACAGGAACAATTGTCTACC
AAAGAGGTGTTTTGTTGCCTCAAAAGGTGTGGTGCGCGAGTGGCAGGAGCAA
AGTAATAAAAGGGTCCTTGCCTTTAATTGGTGAAGCAGATTGCCTTCATGAAA
AATACGGTGGATTAAACAAAAGCAAGCCTTACTACACAGGAGAACATGCAA
AAGCCATAGGAAATTGCCCAATATGGGTGAAAACACCTTTGAAGCTCGCCAA
TGGAACCAAATATAGACCTCCTGCAAAACTATTAAAGGAAAGGGGTTTCTTC
GGAGCTATTGCTGGTTTCCTAGAAGGAGGATGGGAAGGAATGATTGCAGGCT
GGCACGGATACACATCTCACGGAGCACATGGAGTGGCAGTGGCGGCGGACCT
TAAGAGTACGCAAGAAGCTATAAACAAGATAACAAAAAATCTCAATTCTTTG
AGTGAGCTAGAAGTAAAGAATCTTCAAAGACTAAGTGGTGCCATGGATGAAC
TCCACAACGAAATACTCGAGCTGGATGAGAAAGTGGATGATCTCAGAGCTGA
CACTATAAGCTCGCAAATAGAACTTGCAGTCTTGCTTTCCAACGAAGGAATA
ATAAACAGTGAAGATGAGCATCTATTGGCACTTGAGAGAAAACTAAAGAAA
ATGCTGGGTCCCTCTGCTGTAGAGATAGGAAATGGATGCTTCGAAACCAAAC
ACAAGTGCAACCAGACCTGCTTAGACAGGATAGCTGCTGGCACCTTTAATGC
AGGAGAATTTTCTCTCCCCACTTTTGATTCACTGAACATTACTGCTGCATCTTT
AAATGATGATGGATTGGATAACCATACTATACTGCTCTATTACTCAACTGCTG
CTTCTAGTTTGGCTGTAACATTGATGCTAGCTATTTTTATTGTTTATATGGTCT
CCAGAGACAACGTTTCATGCTCCATCTGTCTA

Figure 30A

SEQ ID NO.36
Amino acid sequence of mature HA from strain B/Florida/4/2006

DRICTGITSSNSPHVVKTATQGEVNVTGVIPLTTTPTKSYFANLKGTRTRGKLCPD
CLNCTDLDVALGRPMCVGTTPSAKASILHEVKPVTSGCFPIMHDRTKIRQLPNLL
RGYENIRLSTQNVIDAEKAPGGPYRLGTSGSCPNATSKSGFFATMAWAVPKDNN
KNATNPLTVEVPYICTEGEDQITVWGFHSDNKTQMKNLYGDSNPQKFTSSANGV
TTHYVSQIGSFPDQTEDGGLPQSGRIVVDYMMQKPGKTGTIVYQRGVLLPQKVW
CASGRSKVIKGSLPLIGEADCLHEKYGGLNKSKPYYTGEHAKAIGNCPIWVKTPL
KLANGTKYRPPAKLLKERGFFGAIAGFLEGGWEGMIAGWHGYTSHGAHGVAVA
ADLKSTQEAINKITKNLNSLSELEVKNLQRLSGAMDELHNEILELDEKVDDLRAD
TISSQIELAVLLSNEGIINSEDEHLLALERKLKKMLGPSAVEIGNGCFETKHKCNQT
CLDRIAAGTFNAGEFSLPTFDSLNITAASLNDDGLDNHTILLYYSTAASSLAVTLM
LAIFIVYMVSRDNVSCSICL

Figure 30B

SEQUENCE LISTING

<160> NUMBER OF SEQ ID NOS: 36

<210> SEQ ID NO 1
<211> LENGTH: 1556
<212> TYPE: DNA
<213> ORGANISM: Influenza A virus, subtype H1

<400> SEQUENCE: 1

```
agatcttcgc tgacacaata tgtataggct accatgccaa caactcaacc gacactgttg      60
acacagtact tgagaagaat gtgacagtga cacactctgt caacctactt gaggacagtc     120
acaatggaaa actatgtcta ctaaaaggaa tagccccact acaattgggt aattgcagcg     180
ttgccggatg gatcttagga aacccagaat gcgaattact gatttccaag gaatcatggt     240
cctacattgt agaaacacca aatcctgaga atggaacatg ttacccaggg tatttcgccg     300
actatgagga actgagggag caattgagtt cagtatcttc atttgagaga ttcgaaatat     360
tccccaaaga aagctcatgg cccaaccaca ccgtaaccgg agtatcagca tcatgctccc     420
ataatgggaa aagcagtttt tacagaaatt tgctatggct gacggggaag aatggttttgt     480 acccaaacct gagcaagtcc tatgtaaaca caaagagaga agagtccttt gtactatggg     540
gtgttcatca cccgcctaac atagggaacc aaagggcact ctatcataca gaaaatgctt     600
atgtctctgt agtgtcttca cattatagca gaagattcac cccagaaata gccaaaagac     660
ccaaagtaag agatcaggaa ggaagaatca actactactg gactctgctg gaacctgggg     720
atacaataat atttgaggca aatggaaatc taatagcgcc atggtatgct tttgcactga     780
gtagaggctt tggatcagga atcatcacct caaatgcacc aatggatgaa tgtgatgcga     840
agtgtcaaac acctcaggga gctataaaca gcagtcttcc tttccagaat gtacacccag     900
tcacaatagg agagtgtcca aagtatgtca ggagtgcaaa attaaggatg gttacaggac     960
taaggaacat cccatccatt caatccagag gtttgtttgg agccattgcc ggtttcattg    1020
aaggggggtg gactggaatg gtagatgggt ggtatggtta tcatcatcag aatgagcaag    1080
gatctggcta tgctgcagat caaaaaagta cacaaaatgc cattaacggg attacaaaca    1140
aggtcaattc tgtaattgag aaaatgaaca ctcaattcac agctgtgggc aaagagttca    1200
acaaattgga agaaggatg gaaaacttaa ataaaaagt tgatgatggg tttctagaca    1260
tttggacata taatgcagaa ttgttggttc tactggaaaa tgaaaggact ttggatttcc    1320
atgactccaa tgtgaagaat ctgtatgaga agtaaaaaag ccaattaaag aataatgcca    1380
aagaaatagg aaacgggtgt tttgagttct atcacaagtg taacaatgaa tgcatggaga    1440
gtgtgaaaaa tggtacctat gactatccaa aatattccga agaatcaaag ttaaacaggg    1500
agaaaattga tggagtgaaa ttggaatcaa tgggagtata ctaagagctc aggcct       1556
```

<210> SEQ ID NO 2
<211> LENGTH: 1773
<212> TYPE: DNA
<213> ORGANISM: Influenza A virus, subtype H2

<400> SEQUENCE: 2

```
agcaaaagca ggggttatac catagacaac caaaggcaag acaatggcca tcatttatct      60
aattcttctg ttcacagcag tgagagggga ccaaatatgc attggatacc attccaacaa     120
ttccacagaa aaggttgaca caatcctaga gagaaatgtc actgtgactc acgctgagga     180
cattcttgag aagactcaca atgggaagtt atgcaaacta aatggaatcc ctccacttga     240
attaagggat tgcagcattg ccggatggct ccttgggaat ccagaatgtg atatacttct     300
```

```
aactgtgcca gaatggtcat acataataga aaagaaaat ccaaggaacg gcttgtgcta        360
cccaggcagt ttcaatgatt atgaagaatt gaagcatctt atcagcagcg tgacacattt       420
tgagaaagta aagattctgc ccagaaatga atggacacag catacaacaa ctggaggttc       480
acaggcttgc gcagactatg gtggtccgtc attcttccgg aacatggtct ggttgacaaa       540
gaaagggtcg aattatccaa ttgccaaaag atcttacaac aatacaagtg gggaacaaat       600
gctgatcatt tggggatac atcacccaa tgatgaaagt gaacaagag cattgtatca         660
gaatgtgggg acctatgtgt cagtaggaac atcaacactg aacaaagat catccccaga       720
aatagcaaca agacctaaag tgaatggaca aggaggcaga atggaattct cgtggactat      780
cttagatata tgggacacaa taaattttga gagtactggc aatctaattg caccagaata      840
tggtttcaaa atatccaaac gaggtagttc agggatcatg aaaacagaag gaaaacttga      900
aaactgcgag accaagtgcc aaactccttt gggagcaata atacaacat tacccctttca     960
caatatccac ccactgacca ttggtgagtg ccccaaatat gtaaaatcgg aaagattagt      1020
cttagcaaca ggactaagaa acgtccctca gattgagtca aggggattgt tgggcaat       1080
agctggtttt atagagggtg gatggcaagg aatggttgat ggttggtatg gtatcatca      1140
cagcaatgac cagggatctg gtatgcagc agacaaagaa tccactcaaa aggcaattga      1200
tggaatcacc aacaaggtaa attctgtgat cgaaaagatg aacacccaat cggagctgt      1260
tggaaaagaa ttcagtaact tggagagaag actggagaac ttgaataaaa agatggagga    1320
cggatttcta gatgtgtgga catacaatgc cgagctccta gttctaatgg aaaatgagag     1380
gacacttgac tttcatgatt ctaatgtcaa gaatctatat gataaagtca gaatgcaact     1440
gagagacaat gcaaaagaac tagggaatgg atgttttgaa ttttatcaca atgtgatga     1500
tgaatgcatg aacagtgtga agaatgggac atatgattat tccaagtatg aagaggagtc    1560
taaactaaac aggactgaaa tcaaggggt taaattgagc aatatggggg tttatcaaat    1620
ccttgccatc tatgctacag tagcaggttc cctgtcactg gcaatcatga tagctgggat    1680
ttctatatgg atgtgctcca acgggtctct gcaatgcaga atctgcatat gatcatcagt    1740
cattttgtaa ttaaaaacac ccttgtttct act                                  1773
```

<210> SEQ ID NO 3
<211> LENGTH: 1086
<212> TYPE: DNA
<213> ORGANISM: Influenza A virus, subtype H3

<400> SEQUENCE: 3

```
caaaaacttc ccggaaatga caacagcacg gcaacgctgt gccttgggca ccatgcagta        60
ccaaacggaa cgatagtgaa aacaatcacg aatgaccaaa ttgaagttac taatgctact       120
gagctggtac agagttcctc aacaggtgga atatgcgaca gtcctcatca gatccttgat       180
ggagaaaact gcacactaat agatgctcta ttggagacc ctcagtgtga tggcttccaa        240
aataagaaat gggaccttt tgttgaacgc agcaaagcct acagcaactg ttaccctat         300
gatgtgccgg attatgcctc ccttaggtca ctagttgcct catccggcac actggagttt      360
aacaatgaaa gcttcgattg gactggagtc actcagaatg gaacaagctc tgcttgcaaa      420
aggagatcta ataaaagttt ctttagtaga ttgaattggt tgacccactt aaaatacaaa       480
tacccagcat tgaacgtgac tatgccaaac aatgaaaaat tgacaaaatt gtacatttgg      540
ggggttcacc acccgggtac ggacagtgac caaatcagcc tatatgctca agcatcagga      600
```

| | |
|---|---|
| agaatcacag tctctaccaa aagaagccaa caaactgtaa tcccgaatat cggatctaga | 660 |
| cccagggtaa gggatgtctc cagccgaata agcatctatt ggacaatagt aaaaccggga | 720 |
| gacatacttt tgattaacag cacagggaat ctaattgctc ctcggggtta cttcaaaata | 780 |
| cgaagtggga aaagctcaat aatgagatca gatgcaccca ttggcaaatg caattccgaa | 840 |
| tgcatcactc caaatggaag cattcccaat gacaaaccat tcaaaatgt aaacaggatc | 900 |
| acatatgggg cctgtcccag atatgttaag caaaacactc tgaaattggc aacagggatg | 960 |
| cgaaatgtac cagagaaaca aactagaggc atatttggcg caatcgcggg tttcatagaa | 1020 |
| aatggttggg agggaatggt ggacggttgg tacggtttca ggcatcaaaa ttctgagggc | 1080 |
| acagga | 1086 |

<210> SEQ ID NO 4
<211> LENGTH: 1048
<212> TYPE: DNA
<213> ORGANISM: Influenza A virus, subtype H4

<400> SEQUENCE: 4

| | |
|---|---|
| atgctatcaa tcacgattct gtttctgctc atagcagagg gttcctctca gaattacaca | 60 |
| gggaatcccg tgatatgcct gggacatcat gccgtatcca atgggacaat ggtgaaaacc | 120 |
| ctgactgatg accaagtaga agttgtcact gcccaagaat tagtggaatc gcaacatcta | 180 |
| ccggagttgt gtcctagccc tttaagatta gtagatggac aaacttgtga catcgtcaat | 240 |
| ggtgccttgg ggagtccagg ctgtgatcac ttgaatggtg cagaatggga tgtcttcata | 300 |
| gaacgaccca ctgctgtgga cacttgttat ccatttgatg tgccggatta ccagagccta | 360 |
| cggagtatcc tagcaaacaa tgggaaattt gagttcattg ctgaggaatt ccaatggaac | 420 |
| acagtcaaac aaaatgggaa atccggagca tgcaaaagag caaatgtgaa tgactttttc | 480 |
| aacagattga actggctgac caaatctgat gggaatgcat acccacttca aaacctgaca | 540 |
| aaggttaaca cggggactaa tgcaagactt tacatatggg gagttcatca tccttcaact | 600 |
| gacacagaac aaaccaactt gtataagaac aaccctggga gagtaactgt ttccaccaaa | 660 |
| accagtcaaa caagtgtggt accaaacatt ggcagtagac catgggtaag aggccaaagc | 720 |
| ggcaggatta gcttctattg gacaattgtg gagccaggag acctcatagt cttcaacacc | 780 |
| ataggggaatt taattgctcc gagaggtcat acaagctta cagtcaaaaa gaagagcaca | 840 |
| attctgaata ctgcaattcc cataggatct tgtgttagta aatgtcacac agatagggt | 900 |
| tcaatctcta caaccaaacc cttttcagaac atctcaagaa tatcaattgg ggactgtccc | 960 |
| aagtatgtca acagggatc cttgaaacta gctacaggaa tgaggaatat ccctgagaaa | 1020 |
| gcaaccagag gcctgtttgg tgcaattg | 1048 |

<210> SEQ ID NO 5
<211> LENGTH: 1707
<212> TYPE: DNA
<213> ORGANISM: Influenza A virus, subtype H5

<400> SEQUENCE: 5

| | |
|---|---|
| atggagaaaa tagtgcttct tcttgcaata gtcagtcttg ttaaaagtga tcagatttgc | 60 |
| attggttacc atgcaaacaa ctcgacagag caggttgaca caataatgga aaagaacgtt | 120 |
| actgttacac atgcccaaga catactggaa aagacacaca acgggaaact ctgcgatcta | 180 |
| gatgagtgaa agcctctaat tttgagagat tgtagtgtag ctggatggct cctcggaaac | 240 |
| cctatgtgtg acgaattcat caatgtgccg gaatggtctt acatagtgga aaggccagt | 300 |

```
ccagccaatg acctctgtta cccaggggat ttcaacgact atgaagaact gaaacaccta    360
ttgagcagaa taaccactt tgagaaaatt cagatcatcc ccaaaagttc ttggtccaat    420
catgaagcct catcagggt gagcgcagca tgtccatacc atgggaagcc ctccttttc    480 agaaatgtgg tatggcttat caaaaagaac agtgcatacc aacaataaa gaggagctac    540 aataatacca accaagaaga tcttttggta ctgtggggga ttcaccatcc taatgatgcg    600
gcagagcaga caaagctcta tcaaaaccca accacctata tttccgttgg aacatcaaca    660
ctaaaccaga gattggtccc aaaaatagct actagatcca agtaaacgg caaagtgga    720 agaatggagt tcttctggac aattttaaag ccgaatgatg ccataaattt cgagagtaat    780
ggaaatttca ttgctccaga atatgcatac aaaattgtca agaaggga ctcagcaatt    840 atgaaaagtg aattggaata tggtaactgc aacaccaagt gtcaaactcc aatgggggcg    900
ataaactcta gtatgccatt ccacaacata caccctctca aatcgggga atgccccaaa    960 tatgtgaaat caaacagatt agtccttgcg actggactca gaaataccc tcaaagagat    1020 agaagaagaa aaagagagg actatttgga gctatagcag gttttataga gggaggatgg    1080
caaggaatgg tagatggttg gtatgggtac accatagca atgagcaggg gagtggatac    1140
gctgcagaca aagaatccac tcaaaaggca atagatggag tcaccaataa ggtcaactcg    1200
atcattgaca aaatgaacac tcagtttgag gccgttggaa gggaattta taacttagaa    1260 aggaggatag aaaatttaaa caagaagatg gaagacggat tcctagatgt ctggacttat    1320
aatgctgaac ttctggttct catggaaaat gagagaactc tagactttca tgattcaaat    1380
gtcaagaacc tttacaacaa ggtccgacta cagcttaggg ataatgcaaa ggagctgggt    1440
aatggttgtt tcgagttcta tcacaaatgt gataatgaat gtatggaaag tgtaaaaaac    1500
gggacgtatg actacccgca gtattcagaa gaagcaagac taaacagaga ggaaataagt    1560
ggagtaaaat tggaatcaat gggaacttac caaatactgt caatttattc aacagtggcg    1620
agttccctag cactggcaat catggtagct ggtctatctt tatggatgtg ctccaatggg    1680
tcgttacaat gcagaatttg catttaa                                        1707
```

<210> SEQ ID NO 6
<211> LENGTH: 1050
<212> TYPE: DNA
<213> ORGANISM: Influenza A virus, subtype H6

<400> SEQUENCE: 6

```
atgattgcaa tcattgtaat agcgatactg gcagcagccg aaaagtcaga caagatctgc     60
attgggtatc atgccaacaa ttcaacaaca caggtggata cgatacttga agaatgta     120 accgtcacac actcagttga attgctggag aatcagaagg aagaaagatt ctgcaagatc    180
ttgaacaagg cccctctcga cctaaaggga tgcaccatag agggttggat cttggggaat    240
ccccaatgcg atctgttgct tggtgaccaa agctggcat atatagtgga aagacctact    300
gcccaaaatg ggatatgcta cccaggagct ttgaatgagg tagaagaact gaaagcattt    360
atcggatcag agaaagggt agagagattt gagatgtttc caaaagcac atgggcaggg    420 gtagacacca gcagtgggt aacaaaagct tgtcccttata atagtggttc atctttctac    480
agaaacctcc tatggataat aaagaccaag tcagcagcgt atccagtaat taaggggact    540
tacagcaaca ctgaaaacca gccaatcctc tatttctggg gtgtgcacca tcctcctgac    600
accaatgagc aaaatactct gtatggctct ggcgatcggt atgttaggat gggaactgag    660
```

```
agcatgaatt ttgccaagag cccagaaatt gcggcaagac ccgctgtgaa tggccaaaga      720
ggtcgaattg attattactg gtctgtttta aaaccaggag aaaccttgaa tgtggaatct      780
aatggaaatc taatcgctcc ttggtatgca tacaaatttg tcaacacaaa taataaggga      840
gccgtcttca agtcaaattt accaatcgag aattgcgatg ccacatgcca gactattgca      900
ggagtcctaa ggaccaataa aacatttcag aatgtgagcc ctctgtggat aggagaatgc      960
cccaagtatg tgaaaagtga aagtctaagg cttgctactg gactaagaaa tgttccacag     1020
attgaaacca gagggctttt cggagctatc                                      1050

<210> SEQ ID NO 7
<211> LENGTH: 1629
<212> TYPE: DNA
<213> ORGANISM: Influenza A virus, subtype H7

<400> SEQUENCE: 7
gacaaaatat gtcttgggca ccatgctgtg gcaaatggaa caaaagtgaa cacattaaca       60
gagaggggga ttgaagtagt gaacgccaca gagacggtgg aaactgcgaa tatcaagaaa      120
atatgtattc aagggaaaag gccaacagat ctgggacaat gtggacttct aggaacccta      180
ataggacctc cccaatgtga tcaattcctg gagttttact ctgatttgat aattgagcga      240
agagaaggaa ccgatgtgtg ctatcccggt aaattcacaa atgaagaatc actgaggcag      300
atccttcgag ggtcaggagg aattgataag gagtcaatgg gtttcaccta tagtggaata      360
agaaccaatg gagcgacaag tgcctgcaaa agatcaggtt cttctttcta tgcagagatg      420
aagtggttgc tgtcgaattc agacaatgcg gcattccctc aaatgacaaa gtcgtataga      480
aatcccagaa acaaaccagc tctgataatt ggggagttc atcactctgg atcggttagc      540
gagcagacca aactctatgg aagtggaaac aagttgataa cagtaggaag ctcaaaatac      600
cagcaatcat tcaccccaag tccgggagca cggccacaag tgaatggaca atcagggaga      660
atcgattttc actggctact ccttgatccc aatgacacag tgaccttcac tttcaatggg      720
gcattcatag cccctgacag ggcaagtttc tttagaggag aatcactagg agtccagagt      780
gatgttcctc tggattctag ttgtggaggg gattgctttc acagtggggg tacgatagtc      840
agttccctgc cattccaaaa catcaaccct agaactgtgg ggagatgccc tcggtatgtc      900
aaacagacaa gcctcctttt ggctacagga atgagaaatg ttccagagaa tccaaagccc      960
agaggccttt ttggagcaat gctggattc atagagaatg gatgggaggg tctcatcgat     1020
ggatggtatg gtttcagaca tcaaaatgca caggggaag aactgcagc tgactacaaa     1080 agcacccaat ctgcaataga tcagatcaca ggcaaattga atcgtctgat tgacaaaaca     1140
aatcagcagt ttgagctgat agacaatgag ttcaatgaga tagaacaaca aataggaaat     1200
gtcattaatt ggacacgaga cgcaatgact gaggtatggt cgtataatgc tgagctgttg     1260
gtggcaatgg aaaatcagca tacaatagat cttgcggact cagaaatgaa caaactttat     1320
gagcgtgtca gaaaacaact aagggagaat gctgaagaag atggaactgg atgttttgag     1380
atattccata gtgtgatga tcagtgcatg gagagcataa ggaacaacac ttatgaccat     1440
actcaataca gaacagagtc attgcagaat agaatacaga tagcccagt gaaattgagt     1500 agtggataca aagacataat cttatggttt agcttcgggg catcatgttt tcttcttcta     1560
gccgttgtaa tgggattggt tttcatttgc ataaagaatg gaaacatgcg gtgcaccatt     1620
tgtatataa                                                           1629
```

<210> SEQ ID NO 8
<211> LENGTH: 1698
<212> TYPE: DNA
<213> ORGANISM: Influenza A virus, subtype H8

<400> SEQUENCE: 8
atggaaaaat tcatcgcaat agcaaccttg gcgagcacaa atgcatacga taggatatgc 60
attgggtacc aatcaaacaa ctccacagac acagtgaaca ctctcataga acagaatgta 120
ccagtcaccc aaacaatgga gctcgtggaa acagagaaac atcccgctta ttgtaacact 180
gatttaggtg ccccattgga actgcgagac tgcaagattg aggcagtaat ctatgggaac 240
cccaagtgtg acatccatct gaaggatcaa ggttggtcat acatagtgga gaggcccagc 300
gcaccagaag ggatgtgtta ccctggatct gtggaaaatc tagaagaact gaggtttgtc 360
ttctccagtg ctgcatctta caagagaata agactatttg actattccag gtggaatgtg 420
actagatctg gaacgagtaa agcatgcaat gcatcaacag gtggccaatc cttctatagg 480
agcatcaatt ggttgaccaa aaaggaacca gacacttatg acttcaatga aggagcttat 540
gttaataatg aagatggaga catcattttc ttatggggga tccatcatcc gccggacaca 600
aaagagcaga caacactata taaaaatgca aacactttga gtagtgttac tactaacact 660
ataaacagaa gctttcaacc aaatattggt cccagaccat tagtaagagg acagcaaggg 720
aggatggatt actattgggg cattctgaaa agaggggaga ctctgaagat caggaccaac 780
ggaaatttaa tcgcacctga atttggctat ctgctcaaag gtgaaagcta cggcagaata 840
attcaaaatg aggatatacc catcgggaac tgtaacacaa aatgtcaaac atatgcggga 900
gcaatcaata gcagcaaacc ctttcagaat gcaagtaggc attacatggg agaatgtccc 960
aaatatgtga agaaggcaag cttgcgactt gcagttgggc ttaggaatac gccttctgtt 1020
gaacccagag gactgtttgg agccattgct ggtttcattg aaggaggatg gtctggaatg 1080
attgatgggt ggtatggatt tcatcacagc aattcagagg gaacaggaat ggcagctgac 1140
cagaaatcaa cacaagaagc catcgataag atcaccaata aagtcaacaa tatagttgac 1200
aagatgaaca gggagtttga agttgtgaat catgagttct ctgaagttga aaaaagaata 1260
aacatgataa acgataaaat agatgaccaa attgaagatc tttgggctta caatgcagag 1320
ctccttgtgc tcttagagaa ccagaaaacg ctagacgaac atgattccaa tgtcaaaaac 1380
ctttttgatg aagtgaaaag gagactgtca gccaatgcaa tagatgctgg gaacggttgc 1440
tttgacatac ttcacaaatg cgacaatgag tgtatggaaa ctataaagaa cggaacttac 1500
gatcataagg aatatgaaga ggaggctaaa ctagaaagga gcaagataaa tggagtaaaa 1560
ctagaagaga acaccactta caaaattctt agcatttaca gtacagtggc ggccagtctt 1620
tgcttggcaa tcctgattgc tggaggttta atcctgggca tgcaaaatgg atcttgtaga 1680
tgcatgttct gtatttga 1698

<210> SEQ ID NO 9
<211> LENGTH: 1363
<212> TYPE: DNA
<213> ORGANISM: Influenza A virus, subtype H9

<400> SEQUENCE: 9
atggaaacag tatcactaat gactatacta ctagtagcaa cagcaagcaa tgcagacaaa 60
atctgcatcg gccaccagtc aacaaactcc acagaaactg tggacacgct aacagaaacc 120
aatgttcctg tgacacatgc caaagaattg ctccacacag agcacaatgg aatgctgtgt 180

-continued

| | | |
|---|---|---|
| gcaacaaatc tgggacatcc cctaatctta gacacgtgca ctattgaagg actgatctat | 240 | |
| ggtaacccct cttgtgactt gctgttggga ggaagagaat ggtcctacat cgtcgaaagg | 300 | |
| tcatcagctg taaatggaac gtgttaccct gggaatgtag agaacctaga ggaactcagg | 360 | |
| acactttta gttccgctag ttcctaccga agaatcccaaa tcttcccaga cacaatctgg | 420 | |
| aatgtgactt acactggaac aagcaaagca tgttcagatt cattctacag gagtatgaga | 480 | |
| tggctgactc aaaaaagcgg gtcttaccct gttcaagacg ctcaatacac aaataatatg | 540 | |
| ggaaagagca ttcttttcgt gtgggcata catcacccac ccactgaagc tgcacagaca | 600 | |
| aatttgtaca caagaaccga cacaacaaca agcgtgacaa cagaagactt aaataggatc | 660 | |
| ttcaaaccga tggtagggcc aaggcccctt gtcaatggtc tgcagggaag aattaattat | 720 | |
| tattggtcgg tactaaaacc aggccagaca ctgcgagtaa gatccaatgg gaatctaatt | 780 | |
| gctccatggt atggacacat tctttcggga gggagccatg gaagaatcct gaagactgat | 840 | |
| ttaaaaagta gtaattgcgt agtgcaatgt cagactgaaa aaggcggctt aaacagtaca | 900 | |
| ttgccgttcc acaatatcag taaatatgca tttggaaact gtcccaaata tgttagagtt | 960 | |
| aaaagtctca aactggcagt agggttgagg aacgtgcctg ctagatcaag tagaggacta | 1020 | |
| ttcggagcca tagctggatt catagaagga ggttggccag gactagtcgc tggttggtat | 1080 | |
| ggtttccagc attcaaatga tcaaggggtt ggtattgcgg cagataggga ttcaactcaa | 1140 | |
| aaggcaattg atagaataac aaccaaggtg aataatatag tcgacaaaat gaacaaacaa | 1200 | |
| tatgaaataa ttgatcatga attcagtgag gttgaaacta ggctcaacat gatcaataat | 1260 | |
| aagattgatg accaaataca agacatatgg gcatataatg cagagttgct agtactactt | 1320 | |
| gaaaaccaga aaacactcga tgagcatgac gcaaatgtga aga | 1363 | |

<210> SEQ ID NO 10
<211> LENGTH: 1727
<212> TYPE: DNA
<213> ORGANISM: Influenza A virus, subtype H10

<400> SEQUENCE: 10

| | | |
|---|---|---|
| agcaaaagca gggtcacaa tgtacaaagt agtagtaata attgcgctcc ttggagcagt | 60 | |
| gaaaggtctt gacagaatct gcctaggaca ccatgcggtt gccaatggaa ccattgtgaa | 120 | |
| gacccttaca aatgaacaag aggaagtgac caatgctact gagacggtag agagcacaaa | 180 | |
| tttgaataaa ttgtgtatga aggaagaag ctacaaggac ttgggcaatt gtcacccggt | 240 | |
| aggaatgttg ataggaacac ctgtttgtga tccgcacttg accgggacct gggacactct | 300 | |
| cattgagcga gagaatgcca ttgcccactg ttatccaggg gcaaccataa atgaagaagc | 360 | |
| attgaggcag aaaataatgg aaagtggagg aatcagcaag atgagcactg gcttcactta | 420 | |
| tgggtcttcc atcacctcag ctgggaccac taaggcatgc atgagaaatg gaggagatag | 480 | |
| tttctatgca gagctcaaat ggctagtgtc aaagacaaag gacaaaatt cctctcagac | 540 | |
| aacaaacacc tatcggaata cggacacagc agaacatctc ataatatggg gaattcatca | 600 | |
| cccttccagc acacaggaaa agaatgactt atacggaact cagtcactat ctatatcagt | 660 | |
| tgagagttct acatatcaga caactttgt tccagttgtt gggcaagac ctcaggtcaa | 720 | |
| tggacaaagt gggcgaattg actttcactg gacactagta cagccgggtg acaacataac | 780 | |
| cttctcagac aatggaggtc taatagcacc aagtcgagtt agcaaattaa ctggaagggga | 840 | |
| tttgggaatc caatcagaag cgttgataga caacagttgt gaatccaaat gcttttggag | 900 | |
| agggggttct ataaatacaa agctccttt tcaaaatctg tcacccagaa cagtaggtca | 960 | |

-continued

| | |
|---|---|
| atgccccaaa tacgtaaatc agaggagttt actgcttgca acagggatga ggaatgtgcc | 1020 |
| agaagtggtg cagggaaggg gtctgtttgg tgcaatagca gggttcatag aaaacggatg | 1080 |
| ggaaggaatg gtagacggct ggtatggttt cagacaccaa atgcccagg gcacaggcca | 1140 |
| agctgctgat tacaagagta ctcaagcagc tattgaccaa atcacaggga aactgaacag | 1200 |
| gttgattgag aagaccaaca ctgagtttga gtcaatagaa tctgaattca gtgagactga | 1260 |
| gcatcaaatt ggtaacgtca ttaattggac caaagattca ataaccgaca tttggactta | 1320 |
| caacgcagag ctattagtgg caatggagaa tcagcacaca attgacatgg ctgattcaga | 1380 |
| gatgctaaat ctgtatgaaa gggtaagaaa gcaactcaga cagaatgcag aagaagacgg | 1440 |
| aaagggatgt tttgagatat atcatacttg tgatgattcg tgcatggaga gtataaggaa | 1500 |
| caatacttat gaccattcac aatacagaga ggaggctctt ctgaatagac tgaacatcaa | 1560 |
| cccagtgaaa ctttcttcgg ggtacaaaga catcatactt tggtttagct cggggaatc | 1620 |
| atgctttgtt cttctagccg ttgttatggg tcttgttttc ttctgcctga aaaatggaaa | 1680 |
| catgcgatgc acaatctgta tttagttaaa aacaccttgt ttctact | 1727 |

<210> SEQ ID NO 11
<211> LENGTH: 1698
<212> TYPE: DNA
<213> ORGANISM: Influenza A virus, subtype H11

<400> SEQUENCE: 11

| | |
|---|---|
| atggagaaaa cactgctatt tgcagctatt ttcctttgtg tgaaagcaga tgagatctgt | 60 |
| atcgggtatt taagcaacaa ctcgacagac aaagttgaca caataattga gaacaatgtc | 120 |
| acggtcacta gctcagtgga actggttgag acagaacaca ctggatcatt ctgttcaatc | 180 |
| aatggaaaac aaccaataag ccttggagat tgttcatttg ctggatggat attaggaaac | 240 |
| cctatgtgtg atgaactaat tggaaagact tcatggtctt acattgtgga aaaacccaat | 300 |
| ccaacaaatg gaatctgtta cccaggaact ttagagagtg aagaagaact aagactgaaa | 360 |
| ttcagtggag ttttagaatt taacaaattc gaagtattca catcaaatgg atggggtgct | 420 |
| gtaaattcag gagtaggagt aaccgctgca tgcaaattcg ggggttctaa ttctttcttt | 480 |
| cgaaacatgg tatggctgat acaccaatca ggaacatatc ctgtaataaa agaaaccttt | 540 |
| aacaacacca aagggagaga tgtactgatt gtttggggaa ttcatcatcc tgctacactg | 600 |
| acagaacatc aagatctgta taaaaaggac agctcctatg tagcagtggg ttcagagacc | 660 |
| tacaacagaa gattcactcc agaaatcaac actaggccca gagtcaatgg acaggccgga | 720 |
| cggatgacat tctactggaa gatagtcaaa ccaggagaat caataacatt cgaatctaat | 780 |
| ggggcgttcc tagctcctag atatgctttt gagattgtct ctgttggaaa tgggaaactg | 840 |
| ttcaggagcg aactgaacat tgaatcatgc tctaccaaat gtcaaacaga aataggagga | 900 |
| attaatacga caaaaagctt ccacaatgtt cacagaaaca ctatcgggga ttgccccaag | 960 |
| tatgtgaatg tcaaatcctt aaagcttgca acaggaccta gaaatgtccc agcaatagca | 1020 |
| tcgagaggct gtttggagc aatagctgga ttcatagaag ggggatggcc tggactgatc | 1080 |
| aatggatggt atgggttcca acacaggga gaagaaggaa caggcattgc agcagacaag | 1140 |
| gagtcaactc aaaaggcaat agaccagata acatccaagg taaataacat cgttgacagg | 1200 |
| atgaatacaa actttgagtc tgtgcaacac gaattcagtg aaatagagga agaataaat | 1260 |
| caattatcaa aacacgtaga tgattctgtg gttgacatct ggtcatataa tgcacagctt | 1320 |

```
ctcgttttac ttgaaaatga aagacactg gacctccatg actcaaatgt caggaacctc    1380
catgagaaag tcagaagaat gctaaaggac aatgccaaag atgaggggaa cggatgcttc    1440 acctttacc ataagtgtga caataaatgc attgaacgag ttagaaacgg aacatatgat    1500
cataaagaat tcgaggagga atcaaaaatc aatcgccagg agattgaagg ggtgaaacta    1560
gattctagtg ggaatgtgta taaaatactg tcaatttaca gctgcattgc aagcagtctt    1620
gtattggcag cactcatcat ggggttcatg ttttgggcat gcagtaatgg atcatgtaga    1680
tgtaccattt gcatttag                                                  1698

<210> SEQ ID NO 12
<211> LENGTH: 1695
<212> TYPE: DNA
<213> ORGANISM: Influenza A virus, subtype H12

<400> SEQUENCE: 12
atggaaaaat tcatcatttt gagtactgtc ttggcagcaa gctttgcata tgacaaaatt     60
tgcattggat accaaacaaa caactcgact gaaacggtaa acacactaag tgaacaaaac    120
gttccggtga cgcaggtgga agaacttgta catcgtggga ttgatccgat cctgtgtgga    180
acggaactag gatcaccact agtgcttgat gactgttcat tagagggtct aatcctaggc    240
aatcccaaat gtgatcttta tttgaatggc agggaatggt catacatagt agagaggccc    300
aaagagatgg aaggagtttg ctatccaggg tcaattgaaa accaggaaga gctaagatct    360
ctgttttctt ccatcaaaaa atatgaaaga gtgaagatgt ttgatttcac caaatggaat    420
gtcacataca ctgggaccag caaggcctgc aataatacat caaaccaagg ctcattctat    480
aggagcatga gatggttgac cttaaaatca ggacaatttc cagtccaaac agatgagtac    540
aagaacacca gagattcaga cattgtattc acctgggcca ttcaccaccc accaacatct    600
gatgaacaag taaaattata caaaaatcct gatactctct cttcagtcac caccgtagaa    660
atcaatagga gcttcaagcc taatataggg ccaagaccac tcgtgagagg acaacaaggg    720
agaatggatt actactgggc tgttcttaaa cctggacaaa cagtcaaaat acaaaccaat    780
ggtaatctta ttgcacctga atatggtcac ttaatcacag gaaatcaca tggcaggata    840 ctcaagaata atttgcccat gggacagtgt gtgactgaat gtcaattgaa cgagggtgta    900
atgaacacaa gcaaaccttt ccagaacact agtaagcact atattgggaa tgccccaaa    960 tacataccat cagggagttt aaaattggca ataggctca ggaatgtccc acaagttcaa    1020 gatcggggc tctttggagc aattgcaggt ttcatagaag gcggatggcc agggctagtg    1080
gctggttggt acggatttca gcatcaaaat gcggaggga caggcatagc tgcagacaga    1140
gacagcaccc aaagggcaat agacaatatg caaaacaaac tcaacaatgt catcgacaaa    1200
atgaataaac aatttgaagt ggtgaatcat gagtttcag aagtggaaag cagaataaac    1260
atgattaatt ccaaaattga tgatcagata actgacatat gggcatacaa tgctgaattg    1320
cttgtcctat tggaaaatca gaagacatta gatgagcatg acgctaatgt aaggaatcta    1380
catgatcggg tcagaagagt cctgagggaa aatgcaattg acacaggaga cggctgcttt    1440
gagattttac ataatgtga caacaattgt atggacacga ttagaaacgg gacatacaat    1500
cacaaagagt atgaggaaga agcaaaatc gaacgacaga aagtcaatgg tgtgaaactt    1560
gaggagaatt ctacatataa aattctgagc atctacagca gtgttgcctc aagcttagtt    1620
ctactgctca tgattattgg gggtttcatt ttcgggtgtc aaaatggaaa tgttcgttgt    1680
actttctgta tttaa                                                    1695
```

<210> SEQ ID NO 13
<211> LENGTH: 1701
<212> TYPE: DNA
<213> ORGANISM: Influenza A virus, subtype H13

<400> SEQUENCE: 13

| | | | | | |
|---|---|---|---|---|---|
| atggctctaa | atgtcattgc | aactttgaca | cttataagtg | tatgtgtaca | tgcagacaga | 60 |
| atatgcgtgg | ggtatctgag | caccaattca | tcagaaaggg | tcgacacgct | ccttgaaaat | 120 |
| ggggtcccag | tcaccagctc | cattgatctg | attgagacaa | accacacagg | aacatactgt | 180 |
| tctctaaatg | gagtcagtcc | agtgcatttg | ggagattgca | gctttgaagg | atggattgta | 240 |
| ggaaacccag | cctgcaccag | caactttggg | atcagagagt | ggtcatacct | gattgaggac | 300 |
| cccgcggccc | ctcatgggct | tgctaccct | ggagaattaa | caacaatgg | tgaactcaga | 360 |
| cacttgttca | gtggaatcag | gtcattcagt | agaacggaat | tgatcccacc | tacctcctgg | 420 |
| ggggaagtac | ttgacggtac | aacatctgct | tgcagagata | cacgggaac | caacagcttc | 480 |
| tatcgaaatt | tagtttggtt | tataaagaag | aatactagat | atccagttat | cagtaagacc | 540 |
| tacaacaata | caacgggaag | ggatgtttta | gttttatggg | aatacatca | cccagtgtct | 600 |
| gtggatgaga | caaagactct | gtatgtcaat | agtgatccat | acacactggt | ttccaccaag | 660 |
| tcttggagcg | agaaatataa | actagaaacg | ggagtccgac | ctggctataa | tggacagagg | 720 |
| agctggatga | aatttattg | gtctttgata | catccagggg | agatgattac | tttcgagagt | 780 |
| aatggtggat | ttttagcccc | aagatatggg | tacataattg | aagaatatgg | aaaaggaagg | 840 |
| attttccaga | gtcgcatcag | aatgtctagg | tgcaacacca | agtgccagac | ttcggttgga | 900 |
| gggataaaca | caaacagaac | gttccaaaac | atcgataaga | atgctcttgg | tgactgtccc | 960 |
| aaatacataa | agtctggcca | actcaagcta | gccactggac | tcagaaatgt | gccagctata | 1020 |
| tcgaatagag | gattgttcgg | agcaattgca | gggttcatag | aaggaggctg | gccaggttta | 1080 |
| atcaatggtt | ggtacggttt | tcagcatcaa | aatgaacagg | gaacaggaat | agctgcagac | 1140 |
| aaagaatcaa | cacagaaagc | tatagaccag | ataacaacca | aataaataa | cattattgat | 1200 |
| aaaatgaatg | ggaactatga | ttcaattagg | ggtgaattca | atcaagttga | aagcgtata | 1260 |
| aacatgcttg | cagacagaat | agatgatgcc | gtgacggaca | tttggtcata | caatgccaaa | 1320 |
| cttcttgtat | tgctggaaaa | tgataaaact | ttagatatgc | atgatgctaa | tgtaaagaat | 1380 |
| ttacatgagc | aagtacgaag | agaattgaag | gacaatgcaa | ttgacgaagg | aaatggctgt | 1440 |
| tttgaactcc | ttcataaatg | caatgactcc | tgcatgaaa | ctataagaaa | tggaacgtat | 1500 |
| gaccacactg | agtatgcaga | ggagtcaaag | ttaaagaggc | aagaaatcga | tgggatcaaa | 1560 |
| ctcaaatcag | aagacaacgt | ttacaaagca | ttatcaatat | acagttgcat | tgcaagtagt | 1620 |
| gttgtactag | taggactcat | actctctttc | atcatgtggg | cctgtagtag | tgggaattgc | 1680 |
| cgattcaatg | tttgtatata | a | | | | 1701 |

<210> SEQ ID NO 14
<211> LENGTH: 1749
<212> TYPE: DNA
<213> ORGANISM: Influenza A virus, subtype H14

<400> SEQUENCE: 14

| | | | | | |
|---|---|---|---|---|---|
| agcaaaagca | gggaaaatg | attgcactca | tattggttgc | actggctctg | agccacactg | 60 |
| cttattctca | gatcacaaat | gggacaacag | gaaaccccat | tatatgcttg | gggcatcatg | 120 |

-continued

| | |
|---|---|
| cagtggaaaa cggcacatct gttaaaacac taacagacaa tcacgtagaa gttgtgtcag | 180 |
| ctaaagaatt agttgagacg aaccacactg atgaactgtg cccaagcccc ttgaagcttg | 240 |
| tcgacgggca agactgccac ctcatcaatg gtgcattggg gagtccaggc tgtgaccgtt | 300 |
| tgcaggacac cacttgggat gtcttcattg aaaggcccac tgcagtagac acatgttatc | 360 |
| cattcgacgt cccagattac cagagtctca gaagcatcct agcaagcagt gggagtttgg | 420 |
| agttcatcgc cgaacaattc acctggaatg tgtcaaagt tgacggatca agcagtgctt | 480 |
| gtttgagggg cggtcgcaac agcttcttct cccgactaaa ctggctaacc aaagcaacaa | 540 |
| atggaaacta tggacctatt aacgtcacta agaaaatac gggctcttat gtcaggctct | 600 |
| atctctgggg agtgcatcac ccatcaagcg ataatgagca aacggatctc tacaaggtgg | 660 |
| caacagggag agtaacagta tctacccgct cggaccaaat cagtattgtt cccaatatag | 720 |
| gaagtagacc gagggtaagg aatcagagcg gcaggataag catctactgg accctagtaa | 780 |
| acccagggga ctccatcatt ttcaacagta ttgggaattt gattgcacca agaggccact | 840 |
| acaaaataag caaatctact aagagcacag tgcttaaaag tgacaaaagg attgggtcat | 900 |
| gcacaagccc ttgcttaact gataaaggtt cgatccaaag tgacaaacct tttcagaatg | 960 |
| tatcaaggat tgctatagga aactgcccga atatgtaaaa gcaagggtcc ctgatgttag | 1020 |
| caactggaat gcgcaacatc cctggcaaac aggcaaaggg cttatttggg gcaattgctg | 1080 |
| gattcattga aaatggttgg caaggcctga ttgatgggtg gtatggattc aggcaccaaa | 1140 |
| atgctgaagg aacaggaact gctgcagacc tgaagtcaac tcaggcagcc attgatcaga | 1200 |
| taaatggcaa gctgaacaga ttgatagaga agacaaatga aaatatcac caaatagaaa | 1260 |
| aggaattcga acaggtggaa ggaagaatac aagaccttga gaagtacgtt gaggacacta | 1320 |
| agattgattt gtggtcatac aatgctgaat tgctagtagc actagagaat cagcacacaa | 1380 |
| tagatgtcac agactccgaa atgaacaagc tttttgaaag agtaagaagg caattaagag | 1440 |
| agaatgcaga agatcaaggc aacggttgtt tcgagatatt ccatcagtgt gacaacaatt | 1500 |
| gtatagaaag cattagaaac ggaacttatg accacaacat ctacagggat gaagccatca | 1560 |
| acaatcgaat caaataaat cctgtcactt tgacgatggg gtacaaggac ataatcctgt | 1620 |
| ggatttcttt ctccatgtca tgctttgtct tcgtggcact gattctggga tttgttctat | 1680 |
| gggcttgtca aaacgggaat atccgatgcc aaatctgtat ataagaaaaa acacccttg | 1740 |
| tttctactc | 1749 |

<210> SEQ ID NO 15
<211> LENGTH: 1762
<212> TYPE: DNA
<213> ORGANISM: Influenza A virus, subtype H15

<400> SEQUENCE: 15

| | |
|---|---|
| agcaaaagca gggatacaa aatgaacact caaatcatcg tcattctagt cctcggactg | 60 |
| tcgatggtga gatctgacaa gatttgtctc gggcaccatg ccgtagcaaa tgggacaaaa | 120 |
| gtcaacacac taactgagaa aggagtggaa gtggtcaatg ccacggagac agtggagatt | 180 |
| acaggaataa ataagtgtg cacaaaaggg aagaaagcgg tggacttggg atcttgtgga | 240 |
| atactgggaa ctatcattgg gcctccacaa tgtgactctc atcttaaatt caaagctgat | 300 |
| ctgataatag aaagaagaaa ttcaagtgac atctgttacc cagggaaatt cactaatgag | 360 |
| gaagcactga gacaaataat cagagaatct ggtggaattg acaaagagcc aatgggattt | 420 |
| agatattcag gaataaaaac agacgggca accagtgcgt gtaagagaac agtgtcctct | 480 |

-continued ttctactcag aaatgaaatg gcttttatcc agcaaggcta accaggtgtt cccacaactg 540
aatcagacat acaggaacaa cagaaaagaa ccagccctaa ttgtttgggg agtacatcat 600
tcaagttcct tggatgagca aaataagcta tatggagctg ggaacaagct gataacagta 660
ggaagctcaa aataccaaca atcgttttca ccaagtccag ggacaggccc caaagtgaat 720
ggtcaggccg ggaggatcga ctttcattgg atgctattgg acccagggga tacagtcact 780
tttaccttca atggtgcatt catagcccca gatagagcca cctttctccg ctctaatgcc 840
ccatcgggag ttgagtacaa tgggaagtca ctgggaatac agagtgatgc acaaattgat 900
gaatcatgtg aaggggaatg cttctacagt ggagggacaa taaacagccc tttgccattt 960
caaaacatcg atagttgggc tgtcggaagg tgccccagat atgtaaagca atcaagcctg 1020
ccgctggcct taggaatgaa aaatgtacca gagaaaatac atactagggg actgttcggt 1080
gcaattgcag gattcatcga gaatggatgg gaaggactca ttgatggatg gtatggattt 1140
aggcatcaaa atgcacaggg gcagggaaca gctgctgact acaagagtac tcaggctgca 1200
attgaccaga taacagggaa acttaataga ttaattgaaa aaaccaacac acagtttgaa 1260
ctcatagaca atgagttcac tgaagtggag cagcagatag gcaatgtaat aaactggaca 1320
agggactcct tgactgagat ctggtcatac aatgctgaac ttctagtagc aatggaaaat 1380
cagcatacaa ttgaccttgc agattctgaa atgaacaaac tctatgagag agtgagaaga 1440
cagctaaggg agaatgccga ggaggatgga actggatgtt ttgagatttt ccaccgatgt 1500
gacgatcaat gtatggagag catacgaaat aatacttaca atcacactga atatcgacag 1560
gaagccttac agaataggat aatgatcaat ccggtaaagc ttagtggtgg gtacaaagat 1620
gtgatactat ggtttagctt cggggcatca tgtgtaatgc ttctagccat tgctatgggt 1680
cttattttca tgtgtgtgaa aaacgggaat ctgcggtgca ctatctgtat ataattattt 1740
gaaaaacacc cttgtttcta ct 1762

<210> SEQ ID NO 16
<211> LENGTH: 1760
<212> TYPE: DNA
<213> ORGANISM: Influenza A virus, subtype H16

<400> SEQUENCE: 16
agcaaaagca ggggatattg tcaaaacaac agaatggtga tcaaagtgct ctactttctc 60
atcgtattgt taagtaggta ttcgaaagca gacaaaatat gcataggata tctaagcaac 120
aacgccacag acacagtaga cacactgaca gagaacggag ttccagtgac cagctcagtt 180
gatctcgttg aaacaaacca cacaggaaca tactgctcac tgaatggaat cagcccaatt 240
catcttggtg actgcagctt tgagggatgg atcgtaggaa acccttcctg tgccaccaac 300
atcaacatca gagagtggtc gtatctaatt gaggacccca atgcccccaa caaactctgc 360
ttcccaggag agttagataa taatggagaa ttacgacatc tcttcagcgg agtgaactct 420
tttagcagaa cagaattaat aagtcccaac aaatggggag acattctgga tggagtcacc 480
gcttcttgcc gcgataatgg ggcaagcagt ttttacagaa atttggtctg gatagtgaag 540
aataaaaatg gaaaataccc tgtcataaag gggattacaa ataacacaac aggcagagat 600
gttctagtac tctggggcat tcaccatccg gatacagaaa caacagccat aaacttgtac 660
gcaagcaaaa acccctacac attagtatca acaaaggaat ggagcaaaag atatgaacta 720
gaaattggca ccagaatagg tgatggacag agaagttgga tgaaactata ttggcacctc 780

```
atgcgccctg gagagaggat aatgtttgaa agcaacgggg gccttatagc gcccagatac    840
ggatacatca ttgagaagta cggtacagga cgaattttcc aaagtggagt gagaatggcc    900
aaatgcaaca caaagtgtca acatcatta ggtgggataa acaccaacaa aactttccaa     960
aacatagaga gaaatgctct tggagattgc ccaaagtaca taaagtctgg acagctgaag   1020
cttgcaactg ggctgagaaa tgtcccatcc gttggtgaaa gaggtttgtt tggtgcaatt   1080
gcaggcttca tagaaggagg gtggcctggg ctaattaatg gatggtatgg tttccagcat   1140
cagaatgaac aggggactgg cattgctgca gacaaagcct ccactcagaa agcgatagat   1200
gaaataacaa caaaaattaa caatataata gagaagatga acggaaacta tgattcaata   1260 agagggggaat tcaatcaagt agaaaagagg atcaacatgc tcgctgatcg agttgatgat   1320
gcagtaactg acatatggtc gtacaatgct aaacttcttg tactgcttga aaatgggaga   1380
acattggact tacacgacgc aaatgtcagg aacttacacg atcaggtcaa gagaatattg   1440
aaaagtaatg ctattgatga aggagatggt tgcttcaatc ttcttcacaa atgtaatgac   1500
tcatgcatgg aaactattag aaatgggacc tacaatcatg aagattacag gaagaatca    1560 caactgaaaa ggcaggaaat tgagggaata aaattgaagt ctgaagacaa tgtgtataaa   1620
gtactgtcga tttatagctg cattgcaagc agtattgtgc tggtaggtct catacttgcg   1680
ttcataatgt gggcatgcag caatggaaat tgccggttta tgtttgtat atagtcggaa   1740 aaaatacct tgttctact                                                 1760
```

<210> SEQ ID NO 17
<211> LENGTH: 1656
<212> TYPE: DNA
<213> ORGANISM: Artificial Sequence
<220> FEATURE:
<223> OTHER INFORMATION: pCambia expression vector 660 including sequence from Influenza A virus, subtype H5

<400> SEQUENCE: 17

```
gatcagattt gcattggtta ccatgcaaac aattcaacag agcaggttga cacaatcatg     60
gaaaagaacg ttactgttac acatgcccaa gacatactgg aaaagacaca caacgggaag   120
ctctgcgatc tagatggagt gaagcctcta atttttaagag attgtagtgt agctggatgg   180
ctcctcggga acccaatgtg tgacgaattc atcaatgtac cggaatggtc ttacatagtg    240
gagaaggcca atccaaccaa tgacctctgt tacccaggga tttcaacga ctatgaagaa    300 ctgaaacacc tattgagcag aataaaccat tttgagaaaa ttcaaatcat cccaaaagt    360 tcttggtccg atcatgaagc ctcatcagga gttagctcag catgtccata cctgggaagt    420
ccctcctttt ttagaaatgt ggtatggctt atcaaaaaga acagtacata cccaacaata    480
aagaaaagct acaataatac caaccaagag gatcttttgg tactgtgggg aattcaccat    540
cctaatgatg cggcagagca gacaaggcta tcaaaacc caaccaccta tatttccatt    600
gggacatcaa cactaaacca gagattggta ccaaaaatag ctactagatc caaagtaaac    660
gggcaaagtg aaggatgga gttcttctgg acaattttaa aacctaatga tgcaatcaac    720
ttcgagagta tgaaatttt cattgctcca gaatatgcat acaaaattgt caagaaaggg    780
gactcagcaa ttatgaaaag tgaattggaa tatggtaact gcaacaccaa gtgtcaaact    840
ccaatggggg cgataaactc tagtatgcca ttccacaaca tacccctct caccatcggg    900 gaatgcccca aatatgtgaa atcaaacaga ttagtccttg caacgggct cagaaatagc    960 cctcaaagag agagcagaag aaaaaagaga ggactatttg gagctatagc aggttttata   1020
```

```
gagggaggat ggcagggaat ggtagatggt tggtatgggt accaccatag caatgagcag    1080
gggagtgggt acgctgcaga caaagaatcc actcaaaagg caatagatgg agtcaccaat    1140
aaggtcaact caatcattga caaaatgaac actcagtttg aggccgttgg aagggaattt    1200
aataacttag aaaggagaat agagaattta acaagaaga tggaagacgg gtttctagat     1260
gtctggactt ataatgccga acttctggtt ctcatggaaa atgagagaac tctagacttt    1320
catgactcaa atgttaagaa cctctacgac aaggtccgac tacagcttag ggataatgca    1380
aaggagctgg gtaacggttg tttcgagttc tatcacaaat gtgataatga atgtatggaa    1440
agtataagaa acggaacgta caactatccg cagtattcag aagaagcaag attaaaaaga    1500
gaggaaataa gtggggtaaa attggaatca ataggaactt accaaatact gtcaatttat    1560
tcaacagtgg cgagttccct agcactggca atcatgatgg ctggtctatc tttatggatg    1620
tgctccaatg gatcgttaca atgcagaatt tgcatt                              1656
```

```
<210> SEQ ID NO 18
<211> LENGTH: 25
<212> TYPE: DNA
<213> ORGANISM: Artificial Sequence
<220> FEATURE:
<223> OTHER INFORMATION: PCR primer

<400> SEQUENCE: 18
gtattagtaa ttagaatttg gtgtc                                          25

<210> SEQ ID NO 19
<211> LENGTH: 50
<212> TYPE: DNA
<213> ORGANISM: Artificial Sequence
<220> FEATURE:
<223> OTHER INFORMATION: PCR primer

<400> SEQUENCE: 19
ttgtagcttt tctttattgt tgggtatgca ctgttctttt tgataagcca                50

<210> SEQ ID NO 20
<211> LENGTH: 50
<212> TYPE: DNA
<213> ORGANISM: Artificial Sequence
<220> FEATURE:
<223> OTHER INFORMATION: PCR primer

<400> SEQUENCE: 20
acccaacaat aaagaaaagc tacaataatg ccaaccaaga ggatcttttg                50

<210> SEQ ID NO 21
<211> LENGTH: 50
<212> TYPE: DNA
<213> ORGANISM: Artificial Sequence
<220> FEATURE:
<223> OTHER INFORMATION: PCR primer

<400> SEQUENCE: 21
gtgagagggt gtatgttgtg aatggcata gcagagttta tcgcccccat                 50

<210> SEQ ID NO 22
<211> LENGTH: 50
<212> TYPE: DNA
<213> ORGANISM: Artificial Sequence
<220> FEATURE:
<223> OTHER INFORMATION: PCR primer

<400> SEQUENCE: 22
```

```
atgggggcga taaactctgc tatgccattc cacaacatac accctctcac            50
```

<210> SEQ ID NO 23
<211> LENGTH: 38
<212> TYPE: DNA
<213> ORGANISM: Artificial Sequence
<220> FEATURE:
<223> OTHER INFORMATION: PCR primer

<400> SEQUENCE: 23

```
actttgagct cttaaatgca aattctgcat tgtaacga                         38
```

<210> SEQ ID NO 24
<211> LENGTH: 32
<212> TYPE: DNA
<213> ORGANISM: Artificial Sequence
<220> FEATURE:
<223> OTHER INFORMATION: PCR primer

<400> SEQUENCE: 24

```
agttccccgg gctggtatat ttatatgttg tc                               32
```

<210> SEQ ID NO 25
<211> LENGTH: 46
<212> TYPE: DNA
<213> ORGANISM: Artificial Sequence
<220> FEATURE:
<223> OTHER INFORMATION: PCR primer

<400> SEQUENCE: 25

```
aatagagctc cattttctct caagatgatt aattaattaa ttagtc                46
```

<210> SEQ ID NO 26
<211> LENGTH: 46
<212> TYPE: DNA
<213> ORGANISM: Artificial Sequence
<220> FEATURE:
<223> OTHER INFORMATION: PCR primer

<400> SEQUENCE: 26

```
aatagagctc gttaaaatgc ttcttcgtct cctatttata atatgg                46
```

<210> SEQ ID NO 27
<211> LENGTH: 48
<212> TYPE: DNA
<213> ORGANISM: Artificial Sequence
<220> FEATURE:
<223> OTHER INFORMATION: PCR primer

<400> SEQUENCE: 27

```
ttacgaattc tccttcctaa ttggtgtact atcatttatc aaagggga              48
```

<210> SEQ ID NO 28
<211> LENGTH: 1719
<212> TYPE: DNA
<213> ORGANISM: Influenza A virus, subtype H5 from Indonesia/5/05 (H5N1)

<400> SEQUENCE: 28

```
aagcttatgg agaaaatagt gcttcttctt gcaatagtca gtcttgttaa aagtgatcag   60
atttgcattg gttaccatgc aaacaattca acagagcagg ttgacacaat catggaaaag  120
aacgttactg ttacacatgc ccaagacata ctggaaaaga cacacaacgg aagctctgc   180 gatctagatg gagtgaagcc tctaatttta agagattgta gtgtagctgg atggctcctc  240
```

```
gggaacccaa tgtgtgacga attcatcaat gtaccggaat ggtcttacat agtggagaag    300
gccaatccaa ccaatgacct ctgttaccca gggagtttca acgactatga agaactgaaa    360
cacctattga gcagaataaa ccatttgag aaaattcaaa tcatccccaa aagttcttgg     420
tccgatcatg aagcctcatc aggagttagc tcagcatgtc catacctggg aagtccctcc    480 tttttagaa atgtggtatg gcttatcaaa agaacagta catacccaac aataaagaaa      540
agctacaata ataccaacca agaggatctt ttggtactgt ggggaattca ccatcctaat    600
gatgcggcag agcagacaag gctatatcaa aacccaacca cctatatttc cattgggaca   660
tcaacactaa accagagatt ggtaccaaaa atagctacta gatccaaagt aaacgggcaa    720
agtggaagga tggagttctt ctggacaatt ttaaaaccta atgatgcaat caacttcgag   780
agtaatggaa atttcattgc tccagaatat gcatacaaaa ttgtcaagaa aggggactca    840
gcaattatga aaagtgaatt ggaatatggt aactgcaaca ccaagtgtca aactccaatg    900
ggggcgataa actctagtat gccattccac aacatacacc ctctcaccat cggggaatgc    960
cccaaatatg tgaaatcaaa cagattagtc cttgcaacag ggctcagaaa tagccctcaa   1020
agagagagca aagaaaaaaa gagaggacta tttggagcta tagcaggttt tatagaggga   1080
ggatggcagg gaatggtaga tggttggtat gggtaccacc atagcaatga gcaggggagt   1140
gggtacgctg cagacaaaga atccactcaa aaggcaatag atggagtcac caataaggtc   1200
aactcaatca ttgacaaaat gaacactcag tttgaggccg ttggaaggga atttaataac   1260
ttagaaagga gaatagagaa tttaaacaag aagatggaag acgggtttct agatgtctgg   1320
acttataatg ccgaacttct ggttctcatg gaaaatgaga gaactctaga ctttcatgac   1380
tcaaatgtta agaacctcta cgacaaggtc cgactacagc ttagggataa tgcaaaggag   1440
ctgggtaacg gttgtttcga gttctatcac aaatgtgata tgaatgtat ggaaagtata    1500 agaaacggaa cgtacaacta tccgcagtat tcagaagaag caagattaaa agagaggaa    1560 ataagtgggg taaaattgga atcaatagga acttaccaaa tactgtcaat ttattcaaca   1620
gtggcgagtt ccctagcact ggcaatcatg atggctggtc tatctttatg gatgtgctcc   1680
aatggatcgt acaatgcag aatttgcatt taagagctc                           1719
```

<210> SEQ ID NO 29
<211> LENGTH: 1656
<212> TYPE: DNA
<213> ORGANISM: Artificial Sequence
<220> FEATURE:
<223> OTHER INFORMATION: pCambia expression vector 680 including
      sequence from Influenza A virus, subtype H5

<400> SEQUENCE: 29

```
gatcagattt gcattggtta ccatgcaaac aattcaacag agcaggttga cacaatcatg     60
gaaaagaacg ttactgttac acatgcccaa gacatactgg aaaagacaca caacgggaag   120
ctctgcgatc tagatggagt gaagcctcta attttaagag attgtagtgt agctggatgg   180
ctcctcggga acccaatgtg tgacgaattc atcaatgtac cggaatggtc ttacatagtg   240
gagaaggcca atccaaccaa tgacctctgt tacccaggga gtttcaacga ctatgaagaa   300
ctgaaacacc tattgagcag aataaaccat tttgagaaaa ttcaaatcat ccccaaaagt   360
tcttggtccg atcatgaagc ctcatcagga gttagctcag catgtccata cctgggaagt   420
ccctcctttt ttagaaatgt ggtatggctt atcaaaagaa acagtgcata cccaacaata   480
aagaaaagct acaataatgc caaccaagag gatcttttgg tactgtgggg aattcaccat   540
```

```
cctaatgatg cggcagagca gacaaggcta tatcaaaacc caaccaccta tatttccatt    600
gggacatcaa cactaaacca gagattggta ccaaaaatag ctactagatc caaagtaaac    660
gggcaaagtg gaaggatgga gttcttctgg acaatttaa aacctaatga tgcaatcaac    720
ttcgagagta atgaaatttt cattgctcca gaatatgcat acaaaattgt caagaaaggg    780
gactcagcaa ttatgaaaag tgaattggaa tatggtaact gcaacaccaa gtgtcaaact    840
ccaatggggg cgataaactc tgctatgcca ttccacaaca tacaccctct caccatcggg    900
gaatgcccca aatatgtgaa atcaaacaga ttagtccttg caacagggct cagaaatagc    960
cctcaaagag agagcagaag aaaaaagaga ggactatttg gagctatagc aggttttata   1020
gagggaggat ggcagggaat ggtagatggt tggtatgggt accaccatag caatgagcag   1080
gggagtgggt acgctgcaga caaagaatcc actcaaaagg caatagatgg agtcaccaat   1140
aaggtcaact caatcattga caaaatgaac actcagtttg aggccgttgg aagggaattt   1200
aataacttag aaaggagaat agagaattta acaagaaga tggaagacgg gtttctagat   1260
gtctggactt ataatgccga acttctggtt ctcatggaaa atgagagaac tctagacttt   1320
catgactcaa atgttaagaa cctctacgac aaggtccgac tacagcttag ggataatgca   1380
aaggagctgg gtaacggttg tttcgagttc tatcacaaat gtgataatga atgtatggaa   1440
agtataagaa acggaacgta caactatccg cagtattcag aagaagcaag attaaaaaga   1500
gaggaaataa gtggggtaaa attggaatca ataggaactt accaaatact gtcaatttat   1560
tcaacagtgg cgagttccct agcactggca atcatgatgg ctggtctatc tttatggatg   1620
tgctccaatg gatcgttaca atgcagaatt tgcatt                             1656

<210> SEQ ID NO 30
<211> LENGTH: 25
<212> TYPE: DNA
<213> ORGANISM: Artificial Sequence
<220> FEATURE:
<223> OTHER INFORMATION: PCR primer

<400> SEQUENCE: 30
gtattagtaa ttagaatttg gtgtc                                           25

<210> SEQ ID NO 31
<211> LENGTH: 44
<212> TYPE: DNA
<213> ORGANISM: Artificial Sequence
<220> FEATURE:
<223> OTHER INFORMATION: PCR primer

<400> SEQUENCE: 31
gcaagaagaa gcactatttt ctccattttc tctcaagatg atta                      44

<210> SEQ ID NO 32
<211> LENGTH: 45
<212> TYPE: DNA
<213> ORGANISM: Artificial Sequence
<220> FEATURE:
<223> OTHER INFORMATION: PCR primer

<400> SEQUENCE: 32
ttaatcatct tgagagaaaa tggagaaaat agtgcttctt cttgc                     45

<210> SEQ ID NO 33
<211> LENGTH: 38
<212> TYPE: DNA
<213> ORGANISM: Artificial Sequence
```

<220> FEATURE:
<223> OTHER INFORMATION: PCR primer

<400> SEQUENCE: 33
actttgagct cttaaatgca aattctgcat tgtaacga                    38

<210> SEQ ID NO 34
<211> LENGTH: 552
<212> TYPE: PRT
<213> ORGANISM: Influenza A virus, subtype H5, strain A/Vietnam/1194/04

<400> SEQUENCE: 34

```
Asp Gln Ile Cys Ile Gly Tyr His Ala Asn Asn Ser Thr Glu Gln Val
1               5                  10                  15

Asp Thr Ile Met Glu Lys Asn Val Thr Val Thr His Ala Gln Asp Ile
            20                  25                  30

Leu Glu Lys Thr His Asn Gly Lys Leu Cys Asp Leu Asp Gly Val Lys
        35                  40                  45

Pro Leu Ile Leu Arg Asp Cys Ser Val Ala Gly Trp Leu Leu Gly Asn
    50                  55                  60

Pro Met Cys Asp Glu Phe Ile Asn Val Pro Glu Trp Ser Tyr Ile Val
65                  70                  75                  80

Glu Lys Ala Asn Pro Val Asn Asp Leu Cys Tyr Pro Gly Asp Phe Asn
                85                  90                  95

Asp Tyr Glu Glu Leu Lys His Leu Leu Ser Arg Ile Asn His Phe Glu
            100                 105                 110

Lys Ile Gln Ile Ile Pro Lys Ser Ser Trp Ser Ser His Glu Ala Ser
        115                 120                 125

Leu Gly Val Ser Ser Ala Cys Pro Tyr Gln Gly Lys Ser Ser Phe Phe
    130                 135                 140

Arg Asn Val Val Trp Leu Ile Lys Lys Asn Ser Thr Tyr Pro Thr Ile
145                 150                 155                 160

Lys Arg Ser Tyr Asn Asn Thr Asn Gln Glu Asp Leu Leu Val Leu Trp
                165                 170                 175

Gly Ile His His Pro Asn Asp Ala Ala Glu Gln Thr Lys Leu Tyr Gln
            180                 185                 190

Asn Pro Thr Thr Tyr Ile Ser Val Gly Thr Ser Thr Leu Asn Gln Arg
        195                 200                 205

Leu Val Pro Arg Ile Ala Thr Arg Ser Lys Val Asn Gly Gln Ser Gly
    210                 215                 220

Arg Met Glu Phe Phe Trp Thr Ile Leu Lys Pro Asn Asp Ala Ile Asn
225                 230                 235                 240

Phe Glu Ser Asn Gly Asn Phe Ile Ala Pro Glu Tyr Ala Tyr Lys Ile
                245                 250                 255

Val Lys Lys Gly Asp Ser Thr Ile Met Lys Ser Glu Leu Glu Tyr Gly
            260                 265                 270

Asn Cys Asn Thr Lys Cys Gln Thr Pro Met Gly Ala Ile Asn Ser Ser
        275                 280                 285

Met Pro Phe His Asn Ile His Pro Leu Thr Ile Gly Glu Cys Pro Lys
    290                 295                 300

Tyr Val Lys Ser Asn Arg Leu Val Leu Ala Thr Gly Leu Arg Asn Ser
305                 310                 315                 320

Pro Gln Arg Glu Arg Arg Arg Lys Lys Arg Gly Leu Phe Gly Ala Ile
                325                 330                 335

Ala Gly Phe Ile Glu Gly Gly Trp Gln Gly Met Val Asp Gly Trp Tyr
```

```
                340               345                350
Gly Tyr His His Ser Asn Glu Gln Gly Ser Gly Tyr Ala Ala Asp Lys
            355                 360                 365

Glu Ser Thr Gln Lys Ala Ile Asp Gly Val Thr Asn Lys Val Asn Ser
        370                 375                 380

Ile Ile Asp Lys Met Asn Thr Gln Phe Glu Ala Val Gly Arg Glu Phe
385                 390                 395                 400

Asn Asn Leu Glu Arg Arg Ile Glu Asn Leu Asn Lys Lys Met Glu Asp
                405                 410                 415

Gly Phe Leu Asp Val Trp Thr Tyr Asn Ala Glu Leu Leu Val Leu Met
            420                 425                 430

Glu Asn Glu Arg Thr Leu Asp Phe His Asp Ser Asn Val Lys Asn Leu
        435                 440                 445

Tyr Asp Lys Val Arg Leu Gln Leu Arg Asp Asn Ala Lys Glu Leu Gly
    450                 455                 460

Asn Gly Cys Phe Glu Phe Tyr His Lys Cys Asp Asn Glu Cys Met Glu
465                 470                 475                 480

Ser Val Arg Asn Gly Thr Tyr Asp Tyr Pro Gln Tyr Ser Glu Glu Ala
                485                 490                 495

Arg Leu Lys Arg Glu Glu Ile Ser Gly Val Lys Leu Glu Ser Ile Gly
            500                 505                 510

Ile Tyr Gln Ile Leu Ser Ile Tyr Ser Thr Val Ala Ser Ser Leu Ala
        515                 520                 525

Leu Ala Ile Met Val Ala Gly Leu Ser Leu Trp Met Cys Ser Asn Gly
    530                 535                 540

Ser Leu Gln Cys Arg Ile Cys Ile
545                 550

<210> SEQ ID NO 35
<211> LENGTH: 1752
<212> TYPE: DNA
<213> ORGANISM: Influenza B virus, strain B/Florida/4/2006

<400> SEQUENCE: 35
atgaaggcaa taattgtact actcatggta gtaacatcca atgcagatcg aatctgcact      60
ggaataacat cttcaaactc acctcatgtg tcaaaacag ccactcaagg ggaggtcaat     120
gtgactggtg tgataccact aacaacaaca ccaacaaaat cttattttgc aaatctcaaa    180
ggaacaagga ccagagggaa actatgccca gactgtctca actgcacaga tctggatgtg    240
gctttgggca gaccaatgtg tgtggggacc acaccttcgg cgaaggcttc aatactccac    300
gaagtcaaac ctgttacatc cgggtgcttt cctataatgc acgacagaac aaaaatcagg    360
caactaccca tcttctcag aggatatgaa aatatcaggc tatcaaccca aaacgtcatc    420
gatgcggaaa aggcaccagg aggaccctac agacttggaa cctcaggatc ttgccctaac    480
gctaccagta gagcggatt tttcgcaaca atggcttggg ctgtcccaaa ggacaacaac    540
aaaaatgcaa cgaacccact aacagtagaa gtaccataca tttgtacaga aggggaagac    600
caaatcactg tttgggggtt ccattcagat aacaaaaccc aaatgaagaa cctctatgga    660
gactcaaatc tcaaaagtt cacctcatct gctaatggag taaccacaca ctatgtttct    720
cagattggca gcttcccaga tcaaacagaa gacggaggac taccacaaag cggcaggatt    780
gttgttgatt acatgatgca aaaacctggg aaaacaggaa caattgtcta ccaaagaggt    840
gttttgttgc ctcaaaaggt gtggtgcgcg agtggcagga gcaaagtaat aaaagggtcc    900
```

-continued

```
ttgcctttaa ttggtgaagc agattgcctt catgaaaaat acggtggatt aaacaaaagc   960
aagccttact acacaggaga acatgcaaaa gccataggaa attgcccaat atgggtgaaa  1020
acacctttga agctcgccaa tggaaccaaa tatagacctc ctgcaaaact attaaaggaa  1080
aggggtttct tcggagctat tgctggtttc ctagaaggag gatgggaagg aatgattgca  1140
ggctggcacg atacacatc tcacggagca catggagtgg cagtggcggc ggaccttaag  1200
agtacgcaag aagctataaa caagataaca aaaaatctca attctttgag tgagctagaa  1260
gtaaagaatc ttcaaagact aagtggtgcc atggatgaac tccacaacga atactcgag   1320 ctggatgaga agtggatga tctcagagct gacactataa gctcgcaaat gaacttgca   1380 gtcttgcttt ccaacgaagg aataataaac agtgaagatg agcatctatt ggcacttgag  1440
agaaaactaa agaaaatgct gggtccctct gctgtagaga taggaaatgg atgcttcgaa  1500
accaaacaca gtgcaacca gacctgctta gacaggatag ctgctggcac ctttaatgca  1560 ggagaattt ctctccccac ttttgattca ctgaacatta ctgctgcatc tttaaatgat  1620
gatggattgg ataaccatac tatactgctc tattactcaa ctgctgcttc tagtttggct  1680
gtaacattga tgctagctat ttttattgtt tatatggtct ccagagacaa cgtttcatgc  1740
tccatctgtc ta                                                     1752
```

<210> SEQ ID NO 36
<211> LENGTH: 569
<212> TYPE: PRT
<213> ORGANISM: Influenza B virus, strain B/Florida/4/2006

<400> SEQUENCE: 36

```
Asp Arg Ile Cys Thr Gly Ile Thr Ser Ser Asn Ser Pro His Val Val
1               5                   10                  15

Lys Thr Ala Thr Gln Gly Glu Val Asn Val Thr Gly Val Ile Pro Leu
            20                  25                  30

Thr Thr Thr Pro Thr Lys Ser Tyr Phe Ala Asn Leu Lys Gly Thr Arg
        35                  40                  45

Thr Arg Gly Lys Leu Cys Pro Asp Cys Leu Asn Cys Thr Asp Leu Asp
    50                  55                  60

Val Ala Leu Gly Arg Pro Met Cys Val Gly Thr Thr Pro Ser Ala Lys
65                  70                  75                  80

Ala Ser Ile Leu His Glu Val Lys Pro Val Thr Ser Gly Cys Phe Pro
                85                  90                  95

Ile Met His Asp Arg Thr Lys Ile Arg Gln Leu Pro Asn Leu Leu Arg
            100                 105                 110

Gly Tyr Glu Asn Ile Arg Leu Ser Thr Gln Asn Val Ile Asp Ala Glu
        115                 120                 125

Lys Ala Pro Gly Gly Pro Tyr Arg Leu Gly Thr Ser Gly Ser Cys Pro
    130                 135                 140

Asn Ala Thr Ser Lys Ser Gly Phe Phe Ala Thr Met Ala Trp Ala Val
145                 150                 155                 160

Pro Lys Asp Asn Asn Lys Asn Ala Thr Asn Pro Leu Thr Val Glu Val
                165                 170                 175

Pro Tyr Ile Cys Thr Glu Gly Glu Asp Gln Ile Thr Val Trp Gly Phe
            180                 185                 190

His Ser Asp Asn Lys Thr Gln Met Lys Asn Leu Tyr Gly Asp Ser Asn
        195                 200                 205

Pro Gln Lys Phe Thr Ser Ser Ala Asn Gly Val Thr Thr His Tyr Val
    210                 215                 220
```

```
Ser Gln Ile Gly Ser Phe Pro Asp Gln Thr Glu Asp Gly Gly Leu Pro
225                 230                 235                 240

Gln Ser Gly Arg Ile Val Val Asp Tyr Met Met Gln Lys Pro Gly Lys
            245                 250                 255

Thr Gly Thr Ile Val Tyr Gln Arg Gly Val Leu Leu Pro Gln Lys Val
                260                 265                 270

Trp Cys Ala Ser Gly Arg Ser Lys Val Ile Lys Gly Ser Leu Pro Leu
        275                 280                 285

Ile Gly Glu Ala Asp Cys Leu His Glu Lys Tyr Gly Gly Leu Asn Lys
    290                 295                 300

Ser Lys Pro Tyr Tyr Thr Gly Glu His Ala Lys Ala Ile Gly Asn Cys
305                 310                 315                 320

Pro Ile Trp Val Lys Thr Pro Leu Lys Leu Ala Asn Gly Thr Lys Tyr
                325                 330                 335

Arg Pro Pro Ala Lys Leu Leu Lys Glu Arg Gly Phe Phe Gly Ala Ile
                340                 345                 350

Ala Gly Phe Leu Glu Gly Gly Trp Glu Gly Met Ile Ala Gly Trp His
            355                 360                 365

Gly Tyr Thr Ser His Gly Ala His Gly Val Ala Val Ala Ala Asp Leu
        370                 375                 380

Lys Ser Thr Gln Glu Ala Ile Asn Lys Ile Thr Lys Asn Leu Asn Ser
385                 390                 395                 400

Leu Ser Glu Leu Glu Val Lys Asn Leu Gln Arg Leu Ser Gly Ala Met
                405                 410                 415

Asp Glu Leu His Asn Glu Ile Leu Glu Leu Asp Glu Lys Val Asp Asp
                420                 425                 430

Leu Arg Ala Asp Thr Ile Ser Ser Gln Ile Glu Leu Ala Val Leu Leu
            435                 440                 445

Ser Asn Glu Gly Ile Ile Asn Ser Glu Asp Glu His Leu Leu Ala Leu
450                 455                 460

Glu Arg Lys Leu Lys Lys Met Leu Gly Pro Ser Ala Val Glu Ile Gly
465                 470                 475                 480

Asn Gly Cys Phe Glu Thr Lys His Lys Cys Asn Gln Thr Cys Leu Asp
                485                 490                 495

Arg Ile Ala Ala Gly Thr Phe Asn Ala Gly Glu Phe Ser Leu Pro Thr
            500                 505                 510

Phe Asp Ser Leu Asn Ile Thr Ala Ala Ser Leu Asn Asp Asp Gly Leu
        515                 520                 525

Asp Asn His Thr Ile Leu Leu Tyr Tyr Ser Thr Ala Ala Ser Ser Leu
    530                 535                 540

Ala Val Thr Leu Met Leu Ala Ile Phe Ile Val Tyr Met Val Ser Arg
545                 550                 555                 560

Asp Asn Val Ser Cys Ser Ile Cys Leu
                565
```

INFLUENZA VIRUS IMMUNIZING EPITOPE

CROSS REFERENCE TO RELATED APPLICATIONS

This application represents the national stage application of International Application No. PCT/CA2009/001040 filed 15 Jul. 2009, which claims the benefit of U.S. Provisional Patent Application No. 61/081,811 filed 18 Jul. 2008, both of which are incorporated herein by reference in their entirety for all purposes.

FIELD OF INVENTION

The present invention relates to the production of virus-like particles. More specifically, the present invention is directed to the production of virus-like particles comprising influenza antigens, most particularly modified influenza antigens that have broad cross-reactivity with other influenza strains.

BACKGROUND OF THE INVENTION

Influenza is the leading cause of death in humans due to a respiratory virus. Common symptoms include fever, sore throat, shortness of breath, and muscle soreness, among others. During flu season, influenza viruses infect 10-20% of the population worldwide, leading to 250-500,000 deaths annually Influenza viruses are enveloped viruses that bud from the plasma membrane of infected mammalian cells. They are classified into types A, B, or C, based on the nucleoproteins and matrix protein antigens present. Influenza type A viruses may be further divided into subtypes according to the combination of hemagglutinin (HA) and neuraminidase (NA) surface glycoproteins presented. HA governs the ability of the virus to bind to and penetrate the host cell. NA removes terminal sialic acid residues from glycan chains on host cell and viral surface proteins, which prevents viral aggregation and facilitates virus mobility. Currently, 16 HA (H1-H16) and 9 NA (N1-N9) subtypes are recognized. Each type A influenza virus presents one type of HA and one type of NA glycoprotein. Generally, each subtype exhibits species specificity; for example, all HA and NA subtypes are known to infect birds, while only subtypes H1, H2, H3, H5, H7, H9, H10, N1, N2, N3 and N7 have been shown to infect humans (Horimoto 2006; Suzuki 2005). Influenza viruses comprising H5, H7 and H9 are considered the most highly pathogenic forms of influenza A viruses, and are most likely to cause future pandemics.

Influenza pandemics are usually caused by highly transmissible and virulent influenza viruses, and can lead to elevated levels of illness and death globally. The emergence of new influenza A subtypes resulted in 4 major pandemics in the 20th century. The Spanish flu, caused by an H1N1 virus, in 1918-1919 led to the deaths of over 50 million people worldwide between 1917 and 1920. Presently, the risk of the emergence of a new subtype, or of the transmission to humans of a subtype endemic in animals, is always present. Of particular concern is a highly virulent form of avian influenza (also called "bird flu"), outbreaks of which have been reported in several countries around the world. In many cases, this bird flu can result in mortality rates approaching 100% within 48 hours. The spread of the avian influenza virus (H5N1), first identified in Hong Kong in 1997, to other Asian countries and Europe has been postulated to be linked to the migratory patterns of wild birds.

The current method of combating influenza in humans is by annual vaccination. The vaccine is usually a combination of several strains that are predicted to be the dominant strains for the coming "flu-season". The prediction is coordinated by the World Health Organization. Generally, the number of vaccine doses produced each year is not sufficient to vaccinate the world's population. For example, Canada and the United-States obtain enough vaccines doses to immunize about one third of their population, while only 17% of the population of the European Union can be vaccinated. It is evident that current worldwide production of influenza vaccine would be insufficient in the face of a worldwide flu pandemic. Even if the necessary annual production could somehow be met in a given year, the dominant strains change from year to year, thus stockpiling at low-need times in the year is not practical. Economical, large scale production of an effective influenza vaccine is of significant interest to government and private industry alike.

Currently, the most important source viral stocks for use in vaccines are produced in fertilized eggs. The virus particles are harvested, and for an inactivated viral vaccine, disrupted by detergent to inactivate it. Live attenuated vaccines are made of influenza viruses that were adapted for growth at low temperature which means that at normal body temperature, the vaccine is attenuated. Such a vaccine is licensed in USA for use in individuals from 5 to 49 years of age. Inactivated whole virus vaccines are rendered harmless by inactivation with chemical agents and they have been produced in embryonic eggs or mammalian cell culture. All these types of vaccine show some specific advantages and disadvantages. One advantage of vaccines derived from whole viruses is the type of immunity induced by such vaccines. In general, split vaccines induce a strong antibody response while vaccines made of whole viruses induce both an antibody (humoral) and cellular response. Even though a functional antibody response is a criterion for licensure that correlates with protection induced by a vaccine, there is increasing evidence that a T-cell response is also important in influenza immunity—this may also provide better protection in the elderly.

In order to induce a cellular immune response, vaccines made of whole viruses were developed. Due to the high pathogenicity of the influenza strain (e.g. H5N1), these vaccines are produced in BL3+ facility. For highly pathogenic influenza strains such as H5N1, some manufacturers have modified the hemagglutinin gene sequence in order to reduce the pathogenicity of the influenza strain and to make it avirulent and more easily produced in embryonic eggs or mammalian cell culture. Others also use reassortant influenza strains in which the genetic sequences for the hemagglutinin and neuraminidase proteins are cloned in a high-yielding low pathogenic influenza donor strain (A/PR/8/34; Quan F-S et al, 2007). While these methods may produce useful vaccines, they do not provide a solution to the need for high-volume, low cost and fast production of vaccines in the scale necessary to meet the global need in a normal year, and would almost certainly be insufficient in the face of a pandemic.

Using this reverse genetic technology, one might also need to mutate the genetic sequence of the HA protein to make it avirulent. For highly pathogenic influenza strains, the production of whole virus vaccines either requires confinement procedures or the resulting vaccines do not exactly match the genetic sequence of the circulating virus. In the case of live-attenuated vaccines, there is still a risk that the administered vaccine can recombine with an influenza virus from the host, leading to a new influenza virus.

While this method maintains the antigenic epitope and post-translational modifications, there are a number of drawbacks including the risk of contamination due to the use of whole virus and variable yields depending on virus strain. Sub-optimal levels of protection may result from genetic heterogeneity in the virus due to its introduction into eggs. Other disadvantages include extensive planning for obtaining eggs, contamination risks due to chemicals used in purification, and long production times. Also, persons hypersensitive to egg proteins may not be eligible candidates for receiving the vaccine.

In the case of a pandemic, split vaccine production is slowed by the need to adapt the strain for growth in eggs and the variable production yields achieved. Although this technology has been used for years for the production of seasonal vaccines, it can hardly respond in a reasonable timeframe to a pandemic since worldwide manufacturing capacity is limited.

The recent outbreak in Mexico of Influenza type A H1N1 also highlights the urgent medical need to develop rapid methodology for vaccine production of newly emerging strains.

To avoid the use of eggs, influenza viruses have also been produced in mammalian cell culture, for example in MDCK or PERC.6 cells, or the like. Another approach is reverse genetics, in which viruses are produced by cell transformation with viral genes. These methods, however, also require the use of whole virus as well as elaborate methods and specific culture environments.

Several recombinant products have been developed as recombinant influenza vaccine candidates. These approaches have focused on the expression, production, and purification of influenza type A HA and NA proteins, including expression of these proteins using baculovirus-infected insect cells (Crawford et al, 1999; Johansson, 1999), viral vectors, and DNA vaccine constructs (Olsen et al., 1997).

Specifics of an influenza virus infection are well known. Briefly, the infectious cycle is initiated by the attachment of the virion surface HA protein to a sialic acid-containing cellular receptor (glycoproteins and glycolipids). The NA protein mediates processing of the sialic acid receptor, and virus penetration into the cell depends on HA-dependent receptor-mediated endocytosis. In the acidic confines of internalized endosomes containing an influenza virion, the HA protein undergoes conformational changes that lead to fusion of viral and cell membranes and virus uncoating and M2-mediated release of M1 proteins from nucleocapsid-associated ribonucleoproteins (RNPs), which migrate into the cell nucleus for viral RNA synthesis. Antibodies to HA proteins prevent virus infection by neutralizing virus infectivity, whereas antibodies to NA proteins mediate their effect on the early steps of viral replication.

Crawford et al. (1999) disclose expression of influenza HA in baculovirus-infected insect cells. The expressed proteins are described as being capable of preventing lethal influenza disease caused by avian H5 and H7 influenza subtypes. Johansson et al. (1999) teach that baculovirus-expressed influenza HA and NA proteins induce immune responses in animal superior to those induced by a conventional vaccine. Immunogenicity and efficacy of baculovirus-expressed hemagglutinin of equine influenza virus was compared to a homologous DNA vaccine candidate (Olsen et al., 1997). Collectively, these data demonstrate that a high degree of protection against influenza virus challenge can be induced with recombinant HA or NA proteins, using various experimental approaches and in different animal models.

Since previous research has shown that the surface influenza glycoproteins, HA and NA, are the primary targets for eliciting protective immunity against influenza virus and that M1 provides a conserved target for cellular immunity to influenza, a new vaccine candidate may include these viral antigens as a protein macromolecular particle, such as virus-like particles (VLPs). As vaccine products, VLPs offer the advantage of being more immunogenic than subunit or recombinant antigens and are able to stimulate both humoral and cellular immune response (Grgacic and Anderson, 2006). Further, the particle with these influenza antigens may display conformational epitopes that elicit neutralizing antibodies to multiple strains of influenza viruses.

Production of a non-infectious influenza virus strain for vaccine purposes is one way to avoid inadvertent infection. Alternatively, virus-like particles (VLPs) as substitutes for the cultured virus have been investigated. VLPs mimic the structure of the viral capsid, but lack a genome, and thus cannot replicate or provide a means for a secondary infection.

Several studies have demonstrated that recombinant influenza proteins self-assemble into VLPs in cell culture using mammalian expression plasmids or baculovirus vectors (Gomez-Puertas et al., 1999; Neumann et al., 2000; Latham and Galarza, 2001). Gomez-Puertas et al. (1999) discloses that efficient formation of influenza VLP depends on the expression levels of several viral proteins. Neumann et al. (2000) established a mammalian expression plasmid-based system for generating infectious influenza virus-like particles entirely from cloned cDNAs. Latham and Galarza (2001) reported the formation of influenza VLPs in insect cells infected with recombinant baculovirus co-expressing HA, NA, M1, and M2 genes. These studies demonstrated that influenza virion proteins may self-assemble upon co-expression in eukaryotic cells.

Gomez-Puertas et al. (2000) teach that, in addition to the hemagglutinin (HA), the matrix protein (M1) of the influenza virus is essential for VLP budding from insect cells. However, Chen et al. (2007) teach that M1 might not be required for VLP formation, and observed that efficient release of M1 and VLPs required the presence of HA and sialidase activity provided by NA. The NA cleaves the sialic acids of the glycoproteins at the surface of the cells producing the VLPs, and releasing the VLPs in the medium.

Quan et al (2007) teach that a VLP vaccine produced in a baculovirus expression system (insect cell) induces a protective immunity against some strains of influenza virus (A/PR8/34 (H1N1)). The VLPs studied by Quan were observed to bud from the plasma membrane, and were considered to be of the correct size and morphology, similar to those obtained in a mammalian system (MDCK cells).

Enveloped viruses may obtain their lipid envelope when 'budding' out of the infected cell and obtain the membrane from the plasma membrane, or from that of an internal organelle. Influenza virus particles and VLPs bud from the plasma membrane of the host cell. In mammalian or baculovirus cell systems, for example, influenza buds from the plasma membrane (Quan et al 2007).

Only a few enveloped viruses are known to infect plants (for example, members of the Topoviruses and Rhabdoviruses). Of the known plant enveloped viruses, they are characterized by budding from internal membranes of the host cell, and not from the plasma membrane. Although a small number of recombinant VLPs have been produced in plant hosts, none were derived from the plasma membrane. Current influenza VLP production technologies rely on the co-expression of multiple viral proteins, and this dependence represents a drawback of these technologies since in case of a pandemic and of yearly epidemics, response time is crucial for vaccination. A simpler VLP production system, relying on the expression of only one viral protein is desirable to accelerate the development of vaccine.

The production of influenza HA VLP in plant based system has been described in WO 2009/009876 that essentially showed that the influenza HA is able to self-assemble in plant host cells and bud from plasma membranes in virus-like particles.

In order to protect the world population from influenza and to stave off future pandemics, vaccine manufacturers will need to develop effective, rapid methods producing vaccine doses. The current use of fertilized eggs to produce vaccines is insufficient and involves a lengthy process. HA proteins used are specific for each strain and do not cross-react with other strains to provide broader spectrum vaccines thus necessitating constant production or short reaction time once a new strain is identified.

Certain modifications and/or mutations may be brought to the HA native protein used for producing VLP, such modifications bringing about a hemagglutinin protein that has broader spectrum to induce antibody neutralizing to more than one, or several strains of flu, even after only a single administration.

SUMMARY OF THE INVENTION

It is an aspect of the invention to provide an improved influenza vaccine.

It is a further aspect of the invention to provide novel influenza virus-like particles.

It is a further aspect of the invention to provide an hemagglutinin protein which has been modified to provide a broader spectrum antibody reaction.

The present invention contemplates a polypeptide having an amino acid residue sequence substantially identical to that of a viral envelope N-linked glycoprotein but that is partially or totally free of N-linked carbohydrates (i.e. has one or more glycosylation site that is abolished when compared to an original native HA sequence), as well as methods of producing and utilizing the polypeptide.

It is a further aspect of the invention to provide a HA protein wherein one or more of the N-linked glycosylation sites from HA1 domain has been modified/deleted/mutated/removed/abolished to produce influenza VLPs for the preparation of a broad spectrum influenza vaccine.

Particularly, the HA1 domain comprises amino acids located at positions 1 to 331 as numbered in accordance with strain A/Vietnam/1194/04; SEQ ID NO.34). More particularly, the HA1 domain comprises the globular head portion and the F'2 domain of the protein, corresponding to amino acids between positions 39 to 331 of the protein as numbered in accordance with strain A/Vietnam/1194/04; SEQ ID NO.34). Particularly, the glycosylation site that is abolished is originally present on the globular head portion of the protein, particularly corresponding to amino acids located between positions 39 to 273 of SEQ ID No.34. More particularly, the abolished glycosylation site is originally located in the F'2 domain of the protein, particularly corresponding to amino acids located between positions 274-331 of SEQ ID NO.34.

The present invention provides for amino acid substitutions in the hemagglutinin (NA) molecule of influenza A that can alter the antigenicity and immunogenicity of the HA. These substitutions may alter antigenic sites by altering receptor specificity and/or antibody-antigen binding. In variety of embodiments, the increased antigenicity resulting from the substitution may be useful for the production of vaccines with broader cross-reactivity for influenza. Particularly, the amino acid substitution results in molecules with the immunogenicity characteristics of the amino acid substitution of non-asparagine residue of the HA protein at the location corresponding to the receptor binding-site and particularly corresponding to location 154 and/or 165 and/or 286 (wherein numbering is in accordance with strain A/Vietnam/1194/04; SEQ ID NO.34). In particular embodiments, the amino acid substitution removes/deletes/abolishes a glycosylation site.

The influenza virus increased antigenicity HA molecule may include one or more non-glycosylated amino acid corresponding to positions 154 and/or 165 and/or 286 in H5 HA, where removal of any one of these glycosylation sites results in an increase reactivity with antisera derived from an animal exposed to an influenza virus with a wildtype HA molecule.

In order to destroy a glycosylation site, the triad signal N-X-S/T (where N is a Asn, X can be any amino acid except Pro, and S/T can be both Ser or Thr) may be modified by protein engineering. The first approach used can be to replace the Asn by another amino acid. The second approach is to replace the S/T amino acid at position n+2 relative to the asparagine to be glycosylated, by any other amino acid residue. An appropriate amino acid used to replace the asparagine, serine or threonine is alanine, but other amino acid can also be used. For example, Asn can be replaced by Leu, Ile, Val, Thr, Ser or Ala. Also, Ser or Thr can be replaced by Ala, Val, Ile or Leu.

Particularly, the influenza virus increased antigenicity HA molecule may include a non-asparagine amino acid at positions 154 and/or 165 and/or 286 in H5 HA.

The influenza virus increased antigenicity HA molecule may include HA protein wherein head portion is devoid of N-linked glycosylation sites i.e. all three glycosylation sites have been abolished.

The influenza virus increased antigenicity HA molecule may include one or more than one glycosylation site that is removed, selected from the group consisting of: N-154, N-165 and N-286 (wherein the numbering is in accordance with strain A/Vietnam/1194/04).

The present invention provides a modified hemagglutinin (HA) from different influenza strains.

The present invention also provides a method of producing influenza virus like particles (VLPs) in a non-sialylating host organism comprising:

a) introducing a nucleic acid encoding an influenza hemagglutinin (HA) antigen as defined above, operatively linked to a regulatory region active in a non-sialylating host organism or a portion thereof, and b) incubating the host or a portion thereof under conditions that permit the expression of the nucleic acid, thereby producing the VLPs.

The present invention includes the above method wherein, in the step of introducing (step a), the nucleic acid may be either transiently expressed in the host, or stably expressed in the host. Furthermore, the VLPs may be purified using, for example, size exclusion chromatography.

Additionally the present invention relates to a non-sialylating host organism used for the production of virus like particle (VLP) comprising an influenza virus HA protein. Particularly, suitable host capable of producing a VLP, is for example, a plant or a portion thereof, a plant cell, an insect or a portion thereof, or an insect cell, or a yeast or portion thereof or a yeast cell.

According to the present invention there is provided a nucleic acid comprising a nucleotide sequence encoding a modified influenza HA as defined above operatively linked to a regulatory region active in a non-sialylating host organism. The antigen may be an influenza hemagglutinin (HA) devoid of one or more the N-linked glycosylation sites from the head portion of the molecule (antigenic sites that are normally present in the native sequence).

The present invention also provides a virus like particle (VLP) comprising an influenza virus HA protein as defined herein and one or more than one host lipid. If the host is insect, then the virus like particle (VLP) may comprise an influenza virus HA protein and one or more than one insect lipid, or if the host is a yeast, then the virus like particle (VLP) may comprise an influenza virus HA protein and one or more than one yeast lipid, if the host is a plant, then the virus like particle (VLP) may comprise an influenza virus HA protein and one or more than one plant lipid.

The invention further provides VLPs that are produced in a plant thereby containing one or more than one lipid of plant origin (generally referred to as "plant lipids").

The invention further provides VLPs produced in insect cells comprising lipids from the plasma membrane of insect cells (generally referred to as "insect lipids").

The invention further provides VLPs produced in yeast comprising lipids from the plasma membrane of yeast cells (generally referred to as "yeast lipids").

Also included in the present invention is a composition comprising an effective dose of a VLP comprising an influenza virus HA protein, one or more than one lipid derived from a non-sialylating host production cell, in admixture with a pharmaceutically acceptable carrier. The pharmaceutically acceptable carrier may be suitable for oral, intradermal, intranasal, intramuscular, intraperitoneal, intravenous, or subcutaneous administration.

Further included in the present invention is a vaccine composition comprising an immunologically effective dose of a VLP as defined herein in admixture with a pharmaceutically acceptable carrier with or without the presence of an adjuvant. The vaccine may be administered orally, intradermally, intranasally, intramuscularly, intraperitoneally, intravenously, or subcutaneously. Particularly, the vaccine is administered without the use of an adjuvant.

The present invention also provides for a method of inducing immunity to an influenza virus infection in a subject, the method comprising administering to the subject the virus like particles comprising an influenza virus HA protein, one or more than one host lipid, and a pharmaceutically acceptable carrier. The virus-like particle may be administered to a subject orally, intradermally, intranasally, intramuscularly, intraperitoneally, intravenously, or subcutaneously.

The present invention pertains to a method for inducing immunity to influenza virus infection in a subject comprising administering to the subject an effective dose of a vaccine comprising one or more than one VLP as defined herein.

The subject being treated by the methods as defined above may be selected from the group comprising humans, primates, horses, pigs, birds (avian), water fowl, migratory birds, quail, duck, geese, poultry, chicken, camel, canine, dogs, feline, cats, tiger, leopard, civet, mink, stone marten, ferrets, house pets, livestock, mice, rats, seal, whales and the like. Particularly, the subject may be a human patient or birds in general (including water fowl, migratory birds, poultry such as quail, duck, geese, turkey, chicken), particularly migratory birds or poultry for human consumption (quail, duck, geese, turkey, chicken).

The present invention also provides for a container such as a syringe as well as kits comprising such a container, all of which comprising the vaccine composition as defined herein.

This summary of the invention does not necessarily describe all aspects of the invention.

DETAILED DESCRIPTION OF THE INVENTION

Brief Description of the Drawings

These and other features of the invention will become more apparent from the following description in which reference is made to the appended drawings wherein:

FIG. 1A represents the localisation of glycosylation sites on the influenza virus HA H5 A/Indonesia/5/05. The amino acids identity, position, and location are indicated by analogy on the structure of the A/Vietnam/1194/04; SEQ ID NO. 34 (PDB file: 2IBX). The triple mutant has been made by the destruction of the glycosylation sites N154, N165, and N286 located on the globular head. The study from Bright et al. (2003) has been used to locate the potential antigenic sites. Glycosylation type has been determined based on what is written in the literature about HAs H1, H3 and H7 (Abe Y. et al. (2004); Vigerust D J et al. (2007); and Kuroda et al. (1990);

FIG. 3 shows a sequence of an alfalfa plastocyanin-based expression cassette used for the expression of H1 in accordance with an embodiment of the present invention (SEQ ID NO:8). Protein disulfide isomerase (PDI) signal peptide is underlined. BglII (AGATCT) and SacI (GAGCTC) restriction sites used for cloning are shown in bold;

Figure 1B:
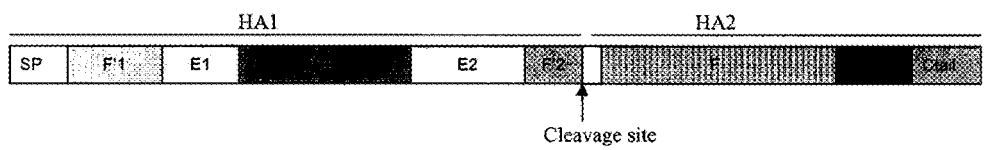
FIG. 1B is an illustration of the subdomains of the HA monomer: The F'1 (1-38 as numbered according to A/Vietnam/1194/04; SEQ ID NO.34), F'2 (274-331) and F subdomains are represented. The receptor binding site and esterase sub-domains that together form the globular head (39-273). The fusion peptide is represented as a white box. The TmD and cytotail cannot be seen on any HA structures since only the soluble bromelain products of HAs have been crystallized and structure elucidated.

or the second (Day 35) immunization. Immunoreactivity was assessed against several H5N1 viruses and one H1N1 virus;

FIG. 8 represents the sequence listing for an Influenza HA0;

FIG. 9 represents the sequence listing for an Influenza HA protein subtype H2;

FIG. 10 represents the sequence listing for an Influenza HA protein subtype H3;

FIG. 11 represents the sequence listing for an Influenza HA protein subtype H4;

FIG. 12 represents the sequence listing for an Influenza HA protein subtype H5;

FIG. 13 represents the sequence listing for an Influenza HA protein subtype H6;

FIG. 14 represents the sequence listing for an Influenza HA protein subtype H7;

FIG. 15 represents the sequence listing for an Influenza HA protein subtype H8;

FIG. 16 represents the sequence listing for an Influenza HA protein subtype H9;

FIG. 17 represents the sequence listing for an Influenza HA protein subtype H10;

FIG. 18 represents the sequence listing for an Influenza HA protein subtype H11;

FIG. 19 represents the sequence listing for an Influenza HA protein subtype H12;

FIG. 20 represents the sequence listing for an Influenza HA protein subtype H13;

FIG. 21 represents the sequence listing for an Influenza HA protein subtype H14;

FIG. 22 represents the sequence listing for an Influenza HA protein subtype H15;

FIG. 23 represents the sequence listing for an Influenza HA protein subtype H16;

FIG. 24 represents the sequence listing for the 660 pCAMBIA expression vector containing the complete wild type H5 sequence;

FIG. 25A-J represent the sequence listings of primers used for PCR amplification;

FIG. 26 represents the sequence listing for the fragment produced, containing the complete H5 coding region including the native signal peptide flanked by a HindIII site immediately upstream of the initial ATG, and a SacI site immediately downstream of the stop (TAA) codon;

FIG. 27 represents the sequence listing for the fragment produced, containing the complete H5 coding region modified to remove all three glycosylation sites, including the native signal peptide flanked by a HindIII site immediately upstream of the initial ATG, and a SacI site immediately downstream of the stop (TAA) codon;

FIG. 28A-D represent the sequence listings for primers for PCR amplification.

FIG. 29 represent amino acid sequence of mature H5 from strain A/Vietnam/1194/04; and FIG. 30A-B represent the nucleic acid and amino acid sequences respectively of mature HA from strain B/Florida/4/2006.

DETAILED DESCRIPTION OF PARTICULAR EMBODIMENTS

The present invention relates to the production of virus-like particles (VLP). More particularly, the present invention is directed to the production of virus-like particles comprising influenza antigens.

The following description is of a particular embodiment.

1—HA Protein

As used herein, a "protein" refers generally to a string of amino acids connected by a peptide bond, which may be folded into secondary, tertiary or quaternary structure to achieve a particular morphology. Alternatively, the terms polypeptide, peptide or peptide fragments may be used in a similar context.

The term "hemagglutinin domain" refers to a peptide comprising either the HA0 precursor polypeptide, or the HA1 and HA2 domains. The hemagglutinin domain does not include the signal peptide, transmembrane domain, or the cytoplasmic tail found in the naturally occurring protein.

With reference to influenza virus, the term "hemagglutinin" or "HA" as used herein refers to a glycoprotein found on the outside of influenza viral particles. HA is a homotrimeric membrane type I glycoprotein, generally comprising a signal peptide, an HA1 domain, and an HA2 domain comprising a membrane-spanning anchor site at the C-terminus and a small cytoplasic tail (FIG. 1B). Nucleotide sequences encoding HA are well known and are available—see, for example, the BioDefence Public Health base (Influenza Virus) or National Center for Biotechnology Information, both of which are incorporated herein by reference.

Structural Information on the Influenza HAs

Figure 2:
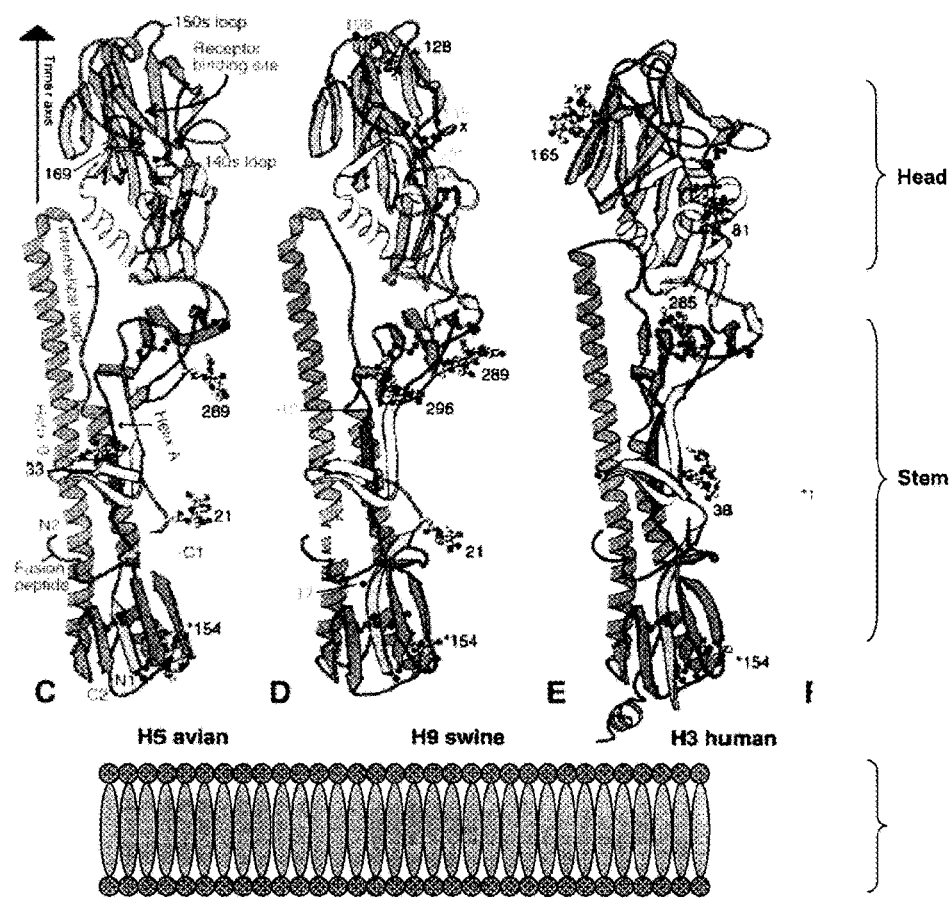
FIG. 2 represents the structures of a monomer of HA from different A subtypes. The lipid bilayer, with its aliphatic counterpart and its polar head is presented as well. Structures taken from Ha et al (Ha Y, Stevens D J, Skehel J J, Wiley D C (2002) H5 avian.

The HA monomer can be subdivided in 2 distinct functional domains, the globular head domain and the stem domain. The correspondence of these domains between the primary sequence and the structure of HA is illustrated at FIGS. 1B and 2. The stem domain is involved in infectivity and pathogenicity of the virus via the extraordinary conformational change it can perform at acidic pH. It is further described as 4 subdomains, the fusion peptide (hydrophobic stretch of 26 amino acids responsible for fusion with the host membrane in the low-pH conformational state); the stem domain itself (that can accommodate 2 extremely different conformations), the transmembrane domain (TmD) (determine the affinity of HA for lipid rafts) the cytoplasmic tail (Ctail) (is involved in secretion of HA). The globular head is divided in 2 subdomains, the receptor binding (RB) domain and the vestigial esterase domain (E). The esterase subdomain is rather buried from the surface of the protein and therefore the majority of antibodies raised against HA binds to the receptor binding domain (represented by the uppermost part of the head in FIG. 2).

The term "homotrimer" or "homotrimeric" indicates that an oligomer is formed by three HA protein molecules. HA protein is synthesized as a 75 kDa monomeric precursor protein (HA0), which assembles at the surface into an elongated trimeric protein. For highly pathogenic avian strains, the precursor protein is cleaved intracellularly at a conserved activation cleavage site (also referred to as fusion peptide) into 2 polypeptide chains, HA1 (328 amino acids) and HA2 (221 amino acids; comprising the transmembrane region), linked by a disulfide bond before trimerization occurs. Although this step is central for virus infectivity, it is not essential for the trimerization of the protein. For mammalian and apathogenic avian influenza virus strains, the precursor HA0 is cleaved extracellularly by proteases secreted by cells of the respiratory tract of the host, or by co-infecting bacteria or mycoplasma. Insertion of HA within the endoplasmic reticulum (ER) membrane of the host cell, signal peptide cleavage and protein glycosylation are co-translational events. Correct refolding of HA requires glycosylation of the protein and formation of 6 intra-chain disulfide bonds. The HA trimer assembles within the cis- and trans-Golgi complex, the transmembrane domain playing a role in the trimerization process. The crystal structures of bromelain-treated HA proteins, which lack the transmembrane domain, have shown a highly conserved structure amongst influenza strains. It has also been established that HA undergoes major conformational changes during the infection process, which requires the precursor HA0 to be cleaved into the 2 polypeptide chains HA1 and HA2. The HA protein may be processed (i.e., comprise HA1 and HA2 domains), or may be unprocessed (i.e. comprise the HA0 domain).

The present invention pertains to the use of an HA protein comprising the transmembrane domain and includes HA1 and HA2 domains, for example the HA protein may be HA0, or processed HA comprising HA1 and HA2.

The HA of the present invention may be obtained from any subtype. For example, the HA may be of subtype H1, H2, H3, H4, H5, H6, H7, H8, H9, H10, H11, H12, H13, H14, H15, or H16.

The present invention includes VLP's comprising HA having modified N-glycans. The recombinant HA of the present invention may also comprise an amino acid sequence based on the sequence any hemagglutinin known in the art—see, for example, the BioDefence Public Health base (Influenza Virus) or National Center for Biotechnology Information wherein the native N-linked glycosylation sites have been removed/mutated/deleted/modified to remove the sugar residues that mask the peptidic antigenic sites.

Furthermore, the HA may be based on the sequence of a hemagglutinin that is isolated from one or more emerging or newly-identified influenza viruses.

Furthermore, VLPs may be produced that comprise a combination of HA subtypes. For example, VLPs may comprise one or more than one HA from the subtype H1, H2, H3, H4, H5, H6, H7, H8, H9, H10, H11, H12, H13, H14, H15, H16, or a combination thereof. Selection of the combination of HAs may be determined by the intended use of the vaccine prepared from the VLP. For example, a vaccine for use in inoculating birds may comprise any combination of HA subtypes, while VLPs useful for inoculating humans may comprise subtypes from one or more than one of subtypes H1, H2, H3 or H5. However, other HA subtype combinations may be prepared depending upon the use of the VLP. In order to produce VLPs comprising combinations of HA subtypes, the desired HA subtype may be co-expressed within the same cell, for example a plant cell.

Particularly, VLPs produced as described herein do not comprise neuraminidase (NA). However, NA may be co-expressed with HA should VLPs comprising HA and NA be desired.

2—Flu Subtypes

The invention includes all types of human influenza virus, including for example, but not limited to the very prevalent A sub-types, and the less common B type, and C type, and to HAs obtained from other influenza subtypes.

The present invention also includes VLPs that comprise HAs obtained from one or more than one influenza subtype. For example, VLPs may comprise one or more than one HA from the subtype H1 (encoded by SEQ ID NO:1), H2 (encoded by SEQ ID NO:2), H3 (encoded by SEQ ID NO:3), H4 (encoded by SEQ ID NO:4), H5 (encoded by SEQ ID NO:5), H6 (encoded by SEQ ID NO:6), H7 (encoded by SEQ ID NO:7), H8 (encoded by SEQ ID NO:8), H9 (encoded by SEQ ID NO:9), H10 (encoded by SEQ ID NO:10), H11 (encoded by SEQ ID NO:11), H12 (encoded by SEQ ID NO:12), H13 (encoded by SEQ ID NO:13), H14 (encoded by SEQ ID NO:14), H15 (encoded by SEQ ID NO:15), H16 (encoded by SEQ ID NO:16), or a combination thereof. One or more that one HA from the one or more than one influenza subtypes may be co-expressed within a plant or insect cell to ensure that the synthesis of the one or more than one HA results in the formation of VLPs comprising a combination of HAs obtained from one or more than one influenza subtype. Selection of the combination of HAs may be determined by the intended use of the vaccine prepared from the VLP. For example a vaccine for use in inoculating humans may comprise any combination of HA subtypes, particularly, one or more than one of subtypes H1, H2, H3, H5, H7, H9, H10, N1, N2, N3 and N7. Particularly, H1, H2, H3, H5.

However, other HA subtype combinations may be prepared depending upon the use of the inoculum.

3—Method of Production

Furthermore, the present invention provides a method of producing virus like particles (VLPs) in a host. Therefore, the invention provides for VLPs, and a method for producing viral VLPs in a host expression system, from the expression of a single envelope protein. The method involves introducing a nucleic acid encoding an antigen operatively linked to a regulatory region active in the host or a portion thereof, and incubating the host or a portion of the host under conditions that permit the expression of the nucleic acid, thereby producing the VLPs.

The regulatory elements of the present invention may also be combined with coding region of interest for expression within a range of host organisms that are amenable to transformation, or transient expression, such as particularly plant, insect or yeast.

Particularly, such organism are plants, both monocots and dicots, for example but not limited to corn, cereal plants, wheat, barley, oat, *Nicotiana* spp, *Brassica* spp, soybean, bean, pea, alfalfa, potato, tomato, ginseng, and *Arabidopsis*.

Methods for stable transformation, and regeneration of these organisms are established in the art and known to one of skill in the art. The methods of obtaining transformed and regenerated plants are also well known in the art.

By "transformation" it is meant the stable interspecific transfer of genetic information (nucleotide sequence) that is manifested genotypically, phenotypically or both. The interspecific transfer of genetic information from a chimeric construct to a host may be heritable and the transfer of genetic information considered stable, or the transfer may be transient and the transfer of genetic information is not inheritable.

Transient expression methods may be used to express the constructs of the present invention (see Liu and Lomonossoff, 2002, Journal of Virological Methods, 105:343-348; which is incorporated herein by reference). Alternatively, a vacuum-based transient expression method, as described by Kapila et al. 1997 (incorporated herein by reference) may be used. These methods may include, for example, but are not limited to, a method of Agro-inoculation or Agro-infiltration, however, other transient methods may also be used as noted above. With either Agro-inoculation or Agro-infiltration, a mixture of *Agrobacteria* comprising the desired nucleic acid enter the intercellular spaces of a tissue, for example the leaves, aerial portion of the plant (including stem, leaves and flower), other portion of the plant (stem, root, flower), or the whole plant. After crossing the epidermis, the *Agrobacterium* infect and transfer t-DNA copies into the cells. The t-DNA is episomally transcribed and the mRNA translated, leading to the production of the protein of interest in infected cells, however, the passage oft-DNA inside the nucleus is transient.

4—Host Organism

The VLPs of the present invention may be produced in a host cell that is characterized by lacking the ability to sialylate proteins, for example lacking sialidase, such as a plant cell, an insect cell, fungi, and other organisms including sponge, coelenterara, annelida, arthoropoda, mollusca, nemathelminthea, trochelmintes, plathelminthes, chaetognatha, tentaculate, *chlamydia*, spirochetes, gram-positive bacteria, cyanobacteria, archaebacteria, as identified in glycoforum.

The VLPs produced as described herein do not typically comprise neuraminidase (NA). However, NA may be co-expressed with HA should VLPs comprising HA and NA be desired.

Particularly, the VLPs of the present invention may be produced in plant cells, a whole plant or portions thereof such as leaf, seeds, or any other plant matter.

By the term "plant matter", it is meant any material derived from a plant. Plant matter may comprise an entire plant, tissue, cells, or any fraction thereof. Further, plant matter may comprise intracellular plant components, extracellular plant components, liquid or solid extracts of plants, or a combination thereof. Further, plant matter may comprise plants, plant cells, tissue, a liquid extract, or a combination thereof, from plant leaves, stems, flowers, fruit, roots or a combination thereof. Plant matter may comprise a plant or portion thereof which has not been subjected to any processing steps. However, it is also contemplated that the plant material may be subjected to minimal processing steps as defined below, or more rigorous processing, including partial or substantial protein purification using techniques commonly known within the art including, but not limited to chromatography, electrophoresis and the like.

By the term "minimal processing" it is meant plant matter, for example, a plant or portion thereof comprising a protein of interest which is partially purified to yield a plant extract, homogenate, fraction of plant homogenate or the like (i.e. minimally processed). Partial purification may comprise, but is not limited to disrupting plant cellular structures thereby creating a composition comprising soluble plant components, and insoluble plant components which may be separated for example, but not limited to, by centrifugation, filtration or a combination thereof. In this regard, proteins secreted within the extracellular space of leaf or other tissues could be readily obtained using vacuum or centrifugal extraction, or tissues could be extracted under pressure by passage through rollers or grinding or the like to squeeze or liberate the protein free from within the extracellular space. Minimal processing could also involve preparation of crude extracts of soluble proteins, since these preparations would have negligible contamination from secondary plant products. Further, minimal processing may involve aqueous extraction of soluble protein from leaves, followed by precipitation with any suitable salt. Other methods may include large scale maceration and juice extraction in order to permit the direct use of the extract.

The plant matter, in the form of plant material or tissue may be orally delivered to a subject. The plant matter may be administered as part of a dietary supplement, along with other foods, or encapsulated. The plant matter or tissue may also be concentrated to improve or increase palatability, or provided along with other materials, ingredients, or pharmaceutical excipients, as required.

Also considered part of this invention are transgenic plants, plant cells or seeds containing the chimeric gene construct of the present invention. Methods of regenerating whole plants from plant cells are also known in the art. In general, transformed plant cells are cultured in an appropriate medium, which may contain selective agents such as antibiotics, where selectable markers are used to facilitate identification of transformed plant cells. Once callus forms, shoot formation can be encouraged by employing the appropriate plant hormones in accordance with known methods and the shoots transferred to rooting medium for regeneration of plants. The plants may then be used to establish repetitive generations, either from seeds or using vegetative propagation techniques. Transgenic plants can also be generated without using tissue cultures.

Also considered part of this invention are transgenic plants, trees, yeast, bacteria, fungi, insect and animal cells containing the chimeric gene construct comprising a nucleic acid encoding recombinant HA0 for VLP production, in accordance with the present invention.

It is contemplated that a plant comprising the protein of interest, or expressing the VLP comprising the protein of interest may be administered to a subject or target organism, in a variety of ways depending upon the need and the situation. For example, the protein of interest obtained from the plant may be extracted prior to its use in either a crude, partially purified, or purified form. If the protein is to be purified, then it may be produced in either edible or non-edible plants. Furthermore, if the protein is orally administered, the plant tissue may be harvested and directly feed to the subject, or the harvested tissue may be dried prior to feeding, or an animal may be permitted to graze on the plant with no prior harvest taking place. It is also considered within the scope of this invention for the harvested plant tissues to be provided as a food supplement within animal feed. If the plant tissue is being feed to an animal with little or not further processing it is preferred that the plant tissue being administered is edible.

Post-transcriptional gene silencing (PTGS) may be involved in limiting expression of transgenes in plants, and co-expression of a suppressor of silencing from the potato virus Y (HcPro) may be used to counteract the specific degradation of transgene mRNAs (Brigneti et al., 1998). Alternate suppressors of silencing are well known in the art and may be used as described herein (Chiba et al., 2006, Virology 346:7-14; which is incorporated herein by reference), for example but not limited to, TEV-p1/HC-Pro (Tobacco etch virus-p1/HC-Pro), BYV-p21, p19 of Tomato bushy stunt virus (TBSV p19), capsid protein of Tomato crinkle virus (TCV-CP), 2b of Cucumber mosaic virus; CMV-2b), p25 of Potato virus X (PVX-p25), p11 of Potato virus M (PVM-p11), p11 of Potato virus S (PVS-p11), p16 of Blueberry scorch virus, (BScV-p16), p23 of Citrus tristexa virus (CTV-p23), p24 of Grapevine leafroll-associated virus-2, (GLRaV-2 p24), p10 of Grapevine virus A, (GVA-p10), p14 of Grapevine virus B (GVB-p14), p10 of Heracleum latent virus (HLV-p10), or p16 of Garlic common latent virus (GCLV-p16). Therefore, a suppressor of silencing, for example, but not limited to, HcPro, TEV-p1/HC-Pro, BYV-p21, TBSV p19, TCV-CP, CMV-2b, PVX-p25, PVM-p11, PVS-p11, BScV-p16, CTV-p23, GLRaV-2 p24, GBV-p14, HLV-p10, GCLV-p16 or GVA-p10, may be co-expressed along with the nucleic acid sequence encoding the protein of interest to further ensure high levels of protein production within a plant.

Figure 7:
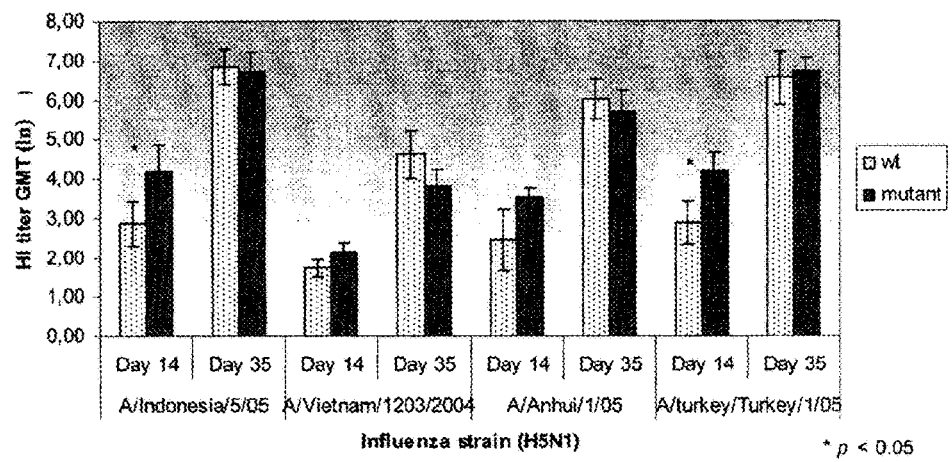
FIG. 7 represents hemagglutination-inhibition (HI) antibody titers after first and second dose. HI titers from rats immunized with the wt or the triple mutant VLP (non-glycosylated) were assessed 14 days after the first (Day 14)

VLPs of enveloped viruses generally acquire their envelope from the membrane they bud through. Plant plasma membranes have a phytosterol complement that may have immunostimulatory effects. To investigate this possibility, plant-made H5 VLPs were administered to animals in the presence of an adjuvant, and the HAI (hemagglutination inhibition antibody response) determined (FIG. 7).

The production of VLPs in plants presents several advantages over the production of these particles in insect cell culture. Plant lipids can stimulate specific immune cells and enhance the immune response induced. Plant membranes are made of lipids, phosphatidylcholine (PC) and phosphatidylethanolamine (PE), and also contain glycosphingolipids that are unique to plants and some bacteria and protozoa. Sphingolipids are unusual in that they are not esters of glycerol like PC or PE but rather consist of a long chain amino alcohol that forms an amide linkage to a fatty acid chain containing more than 18 carbons. PC and PE as well as glycosphingolipids can bind to CD1 molecules expressed by mammalian immune cells such as antigen-presenting cells (APCs) like dentritic cells and macrophages and other cells including B and T lymphocytes in the thymus and liver (Tsuji M, 2006). Furthermore, in addition to the potential adjuvant effect of the presence of plant lipids, the ability of plant N-glycans to facilitate the capture of glycoprotein antigens by antigen presenting cells (Saint-Jore-Dupas, 2007), may be advantageous of the production of VLPs in plants.

Without wishing to be bound by theory, it is anticipated that plant-made VLPs will induce a stronger immune reaction than VLPs made in other production/manufacturing systems and that the immune reaction induced by these plant-made VLPs will be stronger when compared to the immune reaction induced by live or attenuated whole virus vaccines.

Contrary to vaccines made of whole viruses, VLPs provide the advantage as they are non-infectious, thus restrictive biological containment is not as significant an issue as it would be working with a whole, infectious virus, and is not required for production. Plant-made VLPs provide a further advantage again by allowing the expression system to be grown in a greenhouse or field, thus being significantly more economical and suitable for scale-up.

Additionally, plants do not comprise the enzymes involved in synthesizing and adding sialic acid residues to proteins. VLPs may be produced in the absence of neuraminidase (NA), and there is no need to co-express NA, or to treat the producing cells or extract with sialidase (neuraminidase), to ensure VLP production in plants.

Particularly, the VLPs produced in accordance with the present invention do not comprise M1 protein which is known to bind RNA. RNA is a contaminant of the VLP preparation and is undesired when obtaining regulatory approval for the VLP product for use as a human vaccine.

5—Nucleic Acids

The present invention provides a nucleic acid comprising a nucleotide sequence encoding an influenza virus hemagglutinin (HA) antigen, operatively linked to a regulatory region active in a non-sialylating host organism.

The present invention describes, but is not limited to, the cloning of a nucleic acid encoding HA, for example but not limited to, a human influenza A virus HA into a host expression vector, and the production of influenza VLPs from the host, suitable for vaccine production. The VLPs may also be used to produce reagents comprised of recombinant influenza structural proteins that self-assemble into functional and immunogenic homotypic macromolecular protein structures, including subviral influenza particles and influenza VLP, in transformed hosts cells, for example plant cells or insect cells.

The present invention also includes nucleotide sequences H1 (encoded by SEQ ID NO:1), H2 (encoded by SEQ ID NO:2), H3 (encoded by SEQ ID NO:3), H4 (encoded by SEQ ID NO:4), H5 (encoded by SEQ ID NO:5), H6 (encoded by SEQ ID NO:6), H7 (encoded by SEQ ID NO:7), H8 (encoded by SEQ ID NO:8), H9 (encoded by SEQ ID NO:9), H10 (encoded by SEQ ID NO:10), H11 (encoded by SEQ ID NO:11), H12 (encoded by SEQ ID NO:12), H13 (encoded by SEQ ID NO:13), H14 (encoded by SEQ ID NO:14), H15 (encoded by SEQ ID NO:15), and H16 (encoded by SEQ ID NO:16).

Particularly, the present invention includes nucleotide sequences SEQ ID NO:1; SEQ ID NO:5; SEQ ID NO:7 encoding HA from H1, H5 or H7 respectively; a nucleotide sequence SEQ ID NO:1; SEQ ID NO:5; SEQ ID NO:7, that hybridizes under stringent hybridisation conditions to a nucleic acid that encodes the HA from H1, H5 or H7, respectively; or a nucleotide sequence SEQ ID NO:1; SEQ ID NO:5; SEQ ID NO:7, that hybridizes under stringent hybridization conditions to a complement of a nucleic acid encoding the HA from H1, H5 or H7 respectively; wherein the nucleotide sequence encodes a hemagglutinin protein that when expressed forms a VLP, and that the VLP induces the production of an antibody. For example, expression of the nucleotide sequence within a host cell forms a VLP, and the VLP may be used to produce an antibody that is capable of binding HA, including mature HA, HA0, HA1, or HA2. The VLP, when administered to a subject, induces an immune response.

Hybridization under stringent hybridization conditions are known in the art (see for example Current Protocols in Molecular Biology, Ausubel et al., eds. 1995 and supplements; Maniatis et al., in Molecular Cloning (A Laboratory Manual), Cold Spring Harbor Laboratory, 1982; Sambrook and Russell, in Molecular Cloning: A Laboratory Manual, 3rd edition 2001; each of which is incorporated herein by reference). An example of one such stringent hybridization conditions may be about 16-20 hours hybridization in 4×SSC at 65° C., followed by washing in 0.1×SSC at 65° C. for an hour, or 2 washes in 0.1×SSC at 65° C. each for 20 or 30 minutes. Alternatively, an exemplary stringent hybridization condition could be overnight (16-20 hours) in 50% formamide, 4×SSC at 42° C., followed by washing in 0.1×SSC at 65° C. for an hour, or 2 washes in 0.1×SSC at 65° C. each for 20 or 30 minutes, or overnight (16-20 hours), or hybridization in Church aqueous phosphate buffer (7% SDS; 0.5M NaPO4 buffer pH 7.2; 10 mM EDTA) at 65° C., with 2 washes either at 50° C. in 0.1×SSC, 0.1% SDS for 20 or 30 minutes each, or 2 washes at 65° C. in 2×SSC, 0.1% SDS for 20 or 30 minutes each.

Additionally, the present invention includes nucleotide sequences that are characterized as having about 70, 75, 80, 85, 87, 90, 91, 92, 93 94, 95, 96, 97, 98, 99, 100% or any amount therebetween, sequence identity, or sequence similarity, with the nucleotide sequence encoding HA from H1 (SEQ ID NO:1), H5 (SEQ ID NO:5) or H7 (SEQ ID NO:7), wherein the nucleotide sequence encodes a hemagglutinin protein that when expressed forms a VLP, and that the VLP induces the production of an antibody. For example, expression of the nucleotide sequence within a plant cell forms a VLP, and the VLP may be used to produce an antibody that is capable of binding HA, including mature HA, HA0, HA1, or HA2. The VLP, when administered to a subject, induces an immune response.

Sequence identity or sequence similarity may be determined using a nucleotide sequence comparison program, such as that provided within DNASIS (for example, using, but not limited to, the following parameters: GAP penalty 5, # of top diagonals 5, fixed GAP penalty 10, k-tuple 2, floating gap 10, and window size 5). However, other methods of alignment of sequences for comparison are well-known in the art for example the algorithms of Smith & Waterman (1981, Adv. Appl. Math. 2:482), Needleman & Wunsch (J. Mol. Biol. 48:443, 1970), Pearson & Lipman (1988, Proc. Nat'l. Acad. Sci. USA 85:2444), and by computerized implementations of these algorithms (e.g. GAP, BESTFIT, FASTA, and BLAST), or by manual alignment and visual inspection.

Therefore, the present invention further includes a suitable vector comprising the chimeric construct suitable for use with either stable or transient expression systems. The genetic information may be also provided within one or more than one construct. For example, a nucleotide sequence encoding a protein of interest may be introduced in one construct, and a second nucleotide sequence encoding a protein that modifies glycosylation of the protein of interest may be introduced using a separate construct. These nucleotide sequences may then be co-expressed within a host. However, a construct comprising a nucleotide sequence encoding both the protein of interest and the protein that modifies glycosylation profile of the protein of interest may also be used. In this case the nucleotide sequence would comprise a first sequence comprising a first nucleic acid sequence encoding the protein of interest operatively linked to a promoter or regulatory region, and a second sequence comprising a second nucleic acid sequence encoding the protein that modifies the glycosylation profile of the protein of interest, the second sequence operatively linked to a promoter or regulatory region.

By "co-expressed" it is meant that two, or more than two, nucleotide sequences are expressed at about the same time within the host, and within the same tissue of the host. However, the nucleotide sequences need not be expressed at exactly the same time. Rather, the two or more nucleotide sequences are expressed in a manner such that the encoded products have a chance to interact. For example, the protein that modifies glycosylation of the protein of interest may be expressed either before or during the period when the protein of interest is expressed so that modification of the glycosylation of the protein of interest takes place. The two or more than two nucleotide sequences can be co-expressed using a transient expression system, where the two or more sequences are introduced within the host at about the same time under conditions that both sequences are expressed. Alternatively, a platform host comprising one of the nucleotide sequences, for example the sequence encoding the protein that modifies the glycosylation profile of the protein of interest, may be transformed, either transiently or in a stable manner, with an additional sequence encoding the protein of interest. In this case, the sequence encoding the protein that modifies the glycosylation profile of the protein of interest may be expressed within a desired tissue, during a desired stage of development, or its expression may be induced using an inducible promoter, and the additional sequence encoding the protein of interest may be expressed under similar conditions and in the same tissue, to ensure that the nucleotide sequences are co-expressed.

The constructs of the present invention can be introduced into plant cells using Ti plasmids, Ri plasmids, plant virus vectors, direct DNA transformation, micro-injection, electroporation, etc. For reviews of such techniques see for example Weissbach and Weissbach, Methods for Plant Molecular Biology, Academy Press, New York VIII, pp. 421-463 (1988); Geierson and Corey, Plant Molecular Biology, 2d Ed. (1988); and Miki and Iyer, Fundamentals of Gene Transfer in Plants. In Plant Metabolism, 2d Ed. D T. Dennis, D H Turpin, D D Lefebvre, D B Layzell (eds), Addison Wesly, Langmans Ltd. London, pp. 561-579 (1997). Other methods include direct DNA uptake, the use of liposomes, electroporation, for example using protoplasts, micro-injection, microprojectiles or whiskers, and vacuum infiltration. See, for example Bilang, et al. (Gene 100: 247-250 (1991), Scheid et al. (Mol. Gen. Genet. 228: 104-112, 1991), Guerche et al. (Plant Science 52: 111-116, 1987), Neuhause et al. (Theor. Appl Genet. 75: 30-36, 1987), Klein et al., Nature 327: 70-73 (1987); Howell et al. (Science 208: 1265, 1980), Horsch et al. (Science 227: 1229-1231, 1985), DeBlock et al., Plant Physiology 91: 694-701, 1989), Methods for Plant Molecular Biology (Weissbach and Weissbach, eds., Academic Press Inc., 1988), Methods in Plant Molecular Biology (Schuler and Zielinski, eds., Academic Press Inc., 1989), Liu and Lomonossoff (J. Virol Meth, 105:343-348, 2002,), U.S. Pat. Nos. 4,945,050; 5,036, 006; and 5,100,792, U.S. patent application Ser. No. 08/438, 666, filed May 10, 1995, and Ser. No. 07/951,715, filed Sep. 25, 1992, (all of which are hereby incorporated by reference).

By "regulatory region" "regulatory element" or "promoter" it is meant a portion of nucleic acid typically, but not always, upstream of the protein coding region of a gene, which may be comprised of either DNA or RNA, or both DNA and RNA. When a regulatory region is active, and in operative association, or operatively linked, with a gene of interest, this may result in expression of the gene of interest. A regulatory element may be capable of mediating organ specificity, or controlling developmental or temporal gene activation. A "regulatory region" includes promoter elements, core promoter elements exhibiting a basal promoter activity, elements that are inducible in response to an external stimulus, elements that mediate promoter activity such as negative regulatory elements or transcriptional enhancers. "Regulatory region", as used herein, also includes elements that are active following transcription, for example, regulatory elements that modulate gene expression such as translational and transcriptional enhancers, translational and transcriptional repressors, upstream activating sequences, and mRNA instability determinants. Several of these latter elements may be located proximal to the coding region.

In the context of this disclosure, the term "regulatory element" or "regulatory region" typically refers to a sequence of DNA, usually, but not always, upstream (5') to the coding sequence of a structural gene, which controls the expression of the coding region by providing the recognition for RNA polymerase and/or other factors required for transcription to start at a particular site. However, it is to be understood that other nucleotide sequences, located within introns, or 3' of the sequence may also contribute to the regulation of expression of a coding region of interest. An example of a regulatory element that provides for the recognition for RNA polymerase or other transcriptional factors to ensure initiation at a particular site is a promoter element. Most, but not all, eukaryotic promoter elements contain a TATA box, a conserved nucleic acid sequence comprised of adenosine and thymidine nucleotide base pairs usually situated approximately 25 base pairs upstream of a transcriptional start site. A promoter element comprises a basal promoter element, responsible for the initiation of transcription, as well as other regulatory elements (as listed above) that modify gene expression.

There are several types of regulatory regions, including those that are developmentally regulated, inducible or constitutive. A regulatory region that is developmentally regulated, or controls the differential expression of a gene under its control, is activated within certain organs or tissues of an organ at specific times during the development of that organ or tissue. However, some regulatory regions that are developmentally regulated may preferentially be active within certain organs or tissues at specific developmental stages, they may also be active in a developmentally regulated manner, or at a basal level in other organs or tissues within the plant as well. Examples of tissue-specific regulatory regions, for example see-specific a regulatory region, include the napin promoter, and the cruciferin promoter (Rask et al., 1998, J. Plant Physiol. 152: 595-599; Bilodeau et al., 1994, Plant Cell 14: 125-130). An example of a leaf-specific promoter includes the plastocyanin promoter (FIG. 3; U.S. Pat. No. 7,125,978, which is incorporated herein by reference).

An inducible regulatory region is one that is capable of directly or indirectly activating transcription of one or more DNA sequences or genes in response to an inducer. In the absence of an inducer the DNA sequences or genes will not be transcribed. Typically the protein factor that binds specifically to an inducible regulatory region to activate transcription may be present in an inactive form, which is then directly or indirectly converted to the active form by the inducer. However, the protein factor may also be absent. The inducer can be a chemical agent such as a protein, metabolite, growth regulator, herbicide or phenolic compound or a physiological stress imposed directly by heat, cold, salt, or toxic elements or indirectly through the action of a pathogen or disease agent such as a virus. A plant cell containing an inducible regulatory region may be exposed to an inducer by externally applying the inducer to the cell or plant such as by spraying, watering, heating or similar methods. Inducible regulatory elements may be derived from either plant or non-plant genes (e.g. Gatz, C. and Lenk, I. R. P., 1998, Trends Plant Sci. 3, 352-358; which is incorporated by reference). Examples, of potential inducible promoters include, but not limited to, tetracycline-inducible promoter (Gatz, C., 1997, Ann. Rev. Plant Physiol. Plant Mol. Biol. 48, 89-108; which is incorporated by reference), steroid inducible promoter (Aoyama, T. and Chua, N. H., 1997, Plant J. 2, 397-404; which is incorporated by reference) and ethanol-inducible promoter (Salter, M. G., et al, 1998, Plant Journal 16, 127-132; Caddick, M. X., et al, 1998, Nature Biotech. 16, 177-180, which are incorporated by reference) cytokinin inducible IB6 and CKI1 genes (Brandstatter, I. and Kieber, J. J., 1998, Plant Cell 10, 1009-1019; Kakimoto, T., 1996, Science 274, 982-985; which are incorporated by reference) and the auxin inducible element, DR5 (Ulmasov, T., et al., 1997, Plant Cell 9, 1963-1971; which is incorporated by reference).

A constitutive regulatory region directs the expression of a gene throughout the various parts of a plant and continuously throughout plant development. Examples of known constitutive regulatory elements include promoters associated with the CaMV 35S transcript. (Odell et al., 1985, Nature, 313: 810-812), the rice actin 1 (Zhang et al, 1991, Plant Cell, 3: 1155-1165), actin 2 (An et al., 1996, Plant J., 10: 107-121), or tms 2 (U.S. Pat. No. 5,428,147, which is incorporated herein by reference), and triosephosphate isomerase 1 (Xu et. al., 1994, Plant Physiol. 106: 459-467) genes, the maize ubiquitin 1 gene (Cornejo et al, 1993, Plant Mol. Biol. 29: 637-646), the *Arabidopsis* ubiquitin 1 and 6 genes (Holtorf et al, 1995, Plant Mol. Biol. 29: 637-646), and the tobacco translational initiation factor 4A gene (Mandel et al, 1995 Plant Mol. Biol. 29: 995-1004). The term "constitutive" as used herein does not necessarily indicate that a gene under control of the constitutive regulatory region is expressed at the same level in all cell types, but that the gene is expressed in a wide range of cell types even though variation in abundance is often observed.

By "operatively linked" it is meant that the particular sequences, for example a regulatory element and a coding region of interest, interact either directly or indirectly to carry out an intended function, such as mediation or modulation of gene expression. The interaction of operatively linked sequences may, for example, be mediated by proteins that interact with the operatively linked sequences.

The one or more than one nucleotide sequence of the present invention may be expressed in any suitable plant host that is transformed by the nucleotide sequence, or constructs, or vectors of the present invention. Examples of suitable hosts include, but are not limited to, agricultural crops including alfalfa, canola, *Brassica* spp., maize, *Nicotiana* spp., alfalfa, potato, ginseng, pea, oat, rice, soybean, wheat, barley, sunflower, cotton and the like.

The one or more chimeric genetic constructs of the present invention can further comprise a 3' untranslated region. A 3' untranslated region refers to that portion of a gene comprising a DNA segment that contains a polyadenylation signal and any other regulatory signals capable of effecting mRNA processing or gene expression. The polyadenylation signal is usually characterized by effecting the addition of polyadenylic acid tracks to the 3' end of the mRNA precursor. Polyadenylation signals are commonly recognized by the presence of homology to the canonical form 5' AATAAA-3' although variations are not uncommon. One or more of the chimeric genetic constructs of the present invention can also include further enhancers, either translation or transcription enhancers, as may be required. These enhancer regions are well known to persons skilled in the art, and can include the ATG initiation codon and adjacent sequences. The initiation codon must be in phase with the reading frame of the coding sequence to ensure translation of the entire sequence.

Non-limiting examples of suitable 3' regions are the 3' transcribed non-translated regions containing a polyadenylation signal of *Agrobacterium* tumor inducing (Ti) plasmid genes, such as the nopaline synthase (Nos gene) and plant genes such as the soybean storage protein genes, the small subunit of the ribulose-1,5-bisphosphate carboxylase (ssRUBISCO; U.S. Pat. No. 4,962,028; which is incorporated herein by reference) gene, the promoter used in regulating plastocyanin expression (Pwee and Gray 1993; which is incorporated herein by reference). An example of a plastocyanin promoter is described in U.S. Pat. No. 7,125,978 (which is incorporated herein by reference)

As described herein, promoters comprising enhancer sequences with demonstrated efficiency in leaf expression, have been found to be effective in transient expression. Without wishing to be bound by theory, attachment of upstream regulatory elements of a photosynthetic gene by attachment to the nuclear matrix may mediate strong expression. For example up to −784 from the translation start site of the pea plastocyanin gene may be used mediate strong reporter gene expression.

The use of a regulatory region from a photosynthetic gene, for example but not limited to a plastocyanin regulatory region (U.S. Pat. No. 7,125,978; which is incorporated herein by reference), or a regulatory region obtained from Ribulose 1,5-bisphosphate carboxylase/oxygenase (RuBisCO; U.S. Pat. No. 4,962,028; which is incorporated herein by reference), chlorophyll a/b binding protein (CAB; Leutwiler et a; 1986; which is incorporated herein by reference), ST-LS1 (associated with the oxygen-evolving complex of photosystem II, Stockhaus et al. 1989; which is incorporated herein by reference) may be used in accordance with the present invention.

To aid in identification of transformed plant cells, the constructs of this invention may be further manipulated to include plant selectable markers. Useful selectable markers include enzymes that provide for resistance to chemicals such as an antibiotic for example, gentamycin, hygromycin, kanamycin, or herbicides such as phosphinothrycin, glyphosate, chlorosulfuron, and the like. Similarly, enzymes providing for production of a compound identifiable by colour change such as GUS (beta-glucuronidase), or luminescence, such as luciferase or GFP, may be used.

The resulting cDNA copies of these genes may be cloned in a suitable expression vector as required by the host expression system. Examples of appropriate expression vectors for plants are described below, alternatively, baculovirus expression vector, for example, pFastBacl (InVitrogen), resulting in pFastBacl-based plasmids, using known methods, and information provided by the manufacturer's instructions may be used.

The present invention is further directed to a gene construct comprising a nucleic acid encoding HA, as described above, operatively linked to a regulatory element that is operative in a plant. Examples of regulatory elements operative in a plant cell and that may be used in accordance with the present invention include but are not limited to a plastocyanin regulatory region (U.S. Pat. No. 7,125,978; which is incorporated herein by reference), or a regulatory region obtained from Ribulose 1,5-bisphosphate carboxylase/oxygenase (RuBisCO; U.S. Pat. No. 4,962,028; which is incorporated herein by reference), chlorophyll a/b binding protein (CAB; Leutwiler et al; 1986; which is incorporated herein by reference), ST-LS1 (associated with the oxygen-evolving complex of photosystem II, Stockhaus et al. 1989; which is incorporated herein by reference). If the construct is expressed in an insect cell, examples of regulatory elements operative in an insect cell include but are not limited to the polyhedron promoter, the gp64 promoter and the like.

The present invention further provides the cloning of a nucleic acid encoding an HA, for example but not limited to, human influenza A/Indonesia/5/05 virus HA (H5N1) into a plant, yeast or insect expression vector (e.g. baculovirus expression vector) and production of influenza vaccine candidates or reagents comprised of recombinant influenza structural proteins that self-assemble into functional and immunogenic homotypic macromolecular protein structures, including subviral influenza particles and influenza VLP, in transformed plant cells or transformed insect cells.

The nucleic acid encoding the HA, for example but not limited to, a human influenza A/New Calcdonia/20/99 (H1N1) virus HA, or the human influenza A/Indonesia/5/05 virus HA gene may be expressed, for example, using a Baculovirus Expression System in an appropriate cell line, for example, *Spodoptera frugiperda* cells (e.g. Sf-9 cell line; ATCC PTA-4047). Other insect cell lines may also be used.

The nucleic acid encoding the HA may, alternately, be expressed in a plant cell, or in a plant. The nucleic acid encoding HA may be synthesized by reverse transcription and polymerase chain reaction (PCR) using HA RNA. As an example, the RNA may be isolated from human influenza A/New Calcdonia/20/99 (H1N1) virus or human influenza A/Indonesia/5/05 (H5N1) virus, or from cells infected with an influenza virus. For reverse transcription and PCR, oligonucleotide primers specific for HA RNA, for example but not limited to, human influenza A/New Calcdonia/20/99 (H1N1) virus HA genes or human influenza A/Indonesia/5/ 05 (H5N1) virus HA0 genes can be used. Additionally, the nucleic acid encoding HA may be chemically synthesized using methods as would known to one of skill in the art.

6—Proteins

The present invention also includes one or more than one HA protein encoded by nucleotide sequences SEQ ID NO:1; SEQ ID NO:5; SEQ ID NO:7 (encoding HA from H1, H5 or H7, respectively), a nucleotide sequence SEQ ID NO:1; SEQ ID NO:5; SEQ ID NO:7, that hybridizes under stringent hybridisation conditions to a nucleic acid that encodes the HA from H1, H5 or H7, respectively, or a nucleotide sequence SEQ ID NO:1; SEQ ID NO:5; SEQ ID NO:7, that hybridizes under stringent hybridisation conditions to a compliment of a nucleic acid encoding the HA from H1, H5 or H7, respectively, wherein the nucleotide sequence encodes a hemagglutinin protein that when expressed forms a VLP, and that the VLP induces the production of an antibody.

Similarly, the present invention includes HAs associated with the following subtypes H1 (encoded by SEQ ID NO:1), H2 (encoded by SEQ ID NO:2), H3 (encoded by SEQ ID NO:3), H4 (encoded by SEQ ID NO:4), H5 (encoded by SEQ ID NO:5), H6 (encoded by SEQ ID NO:6), H7 (encoded by SEQ ID NO:7), H8 (encoded by SEQ ID NO:8), H9 (encoded by SEQ ID NO:9), H10 (encoded by SEQ ID NO:10), H11 (encoded by SEQ ID NO:11), H12 (encoded by SEQ ID NO:12), H13 (encoded by SEQ ID NO:13), H14 (encoded by SEQ ID NO:14), H15 (encoded by SEQ ID NO:15), H16 (encoded by SEQ ID NO:16); and nucleotide sequences that are characterized as having from about 60 to 100% or any amount therebetween sequence identity, particularly from about 70 to 100% of homology or any amount therebetween, 80 to 100% or any amount there between, 90-100% or any amount therebetween, or 95-100% or any amount therebetween, sequence identity with H1 (SEQ ID NO:1), H2 (SEQ ID NO:2), H3 (SEQ ID NO:3), H4 (SEQ ID NO:4), H5 (SEQ ID NO:5), H6 (SEQ ID NO:6), H7 (SEQ ID NO:7), H8 (SEQ ID NO:8), H9 (SEQ ID NO:9), H10 (SEQ ID NO:10), H11 (SEQ ID NO:11), H12 (SEQ ID NO:12), H13 (SEQ ID NO:13), H14 (SEQ ID NO:14), H15 (SEQ ID NO:15), H16 (SEQ ID NO:16), wherein the nucleotide sequence encodes a hemagglutinin protein that when expressed forms a VLP, and that the VLP induces the production of an antibody. For example, expression of the nucleotide sequence within a plant cell forms a VLP, and the VLP may be used to produce an antibody that is capable of binding HA, including mature HA, HA0, HA1, or HA2. The VLP, when administered to a subject, induces an immune response.

7—VLP

Therefore, the present invention is directed to a VLP comprising one or more than one HA type or subtype.

The term "virus like particle" (VLP), or "virus-like particles" or "VLPs" refers to structures that self-assemble and comprise structural proteins such as influenza HA protein. VLPs are generally morphologically and antigenically similar to virions produced in an infection, but lack genetic information sufficient to replicate and thus are non-infectious. In some examples, VLPs may comprise a single protein species, or more than one protein species. For VLPs comprising more than one protein species, the protein species may be from the same species of virus, or may comprise a protein from a different species, genus, subfamily or family of virus (as designated by the ICTV nomenclature). In other examples, one or more of the protein species comprising a VLP may be modified from the naturally occurring sequence. VLPs may be produced in suitable host cells including plant and insect host cells. Following extraction from the host cell and upon isolation and further purification under suitable conditions, VLPs may be purified as intact structures.

The invention also includes, but is not limited to, influenza derived VLPs that obtain a lipid envelope from the plasma membrane of the cell in which the VLP proteins are expressed. For example, if the VLP is expressed in a plant-based system, the VLP may obtain a lipid envelope from the plasma membrane of the cell.

Generally, the term "lipid" refers to a fat-soluble (lipophilic), naturally-occurring molecules. The term is also used more specifically to refer to fatty-acids and their derivatives (including tri-, di-, and monoglycerides and phospholipids), as well as other fat-soluble sterol-containing metabolites or sterols. Phospholipids are a major component of all biological membranes, along with glycolipids, sterols and proteins. Examples of phospholipids include phosphatidylethanolamine, phosphatidylcholine, phosphatidylinositol, phosphatidylserine, and the like. Examples of sterols include zoosterols (e.g., cholesterol) and phytosterols. Over 200 phytosterols have been identified in various plant species, the most common being campesterol, stigmasterol, ergosterol, brassicasterol, delta-7-stigmasterol, delta-7-avenasterol, daunosterol, sitosterol, 24-methylcholesterol, cholesterol or beta-sitosterol. As one of skill in the art would understand, the lipid composition of the plasma membrane of a cell may vary with the culture or growth conditions of the cell or organism from which the cell is obtained.

Cell membranes generally comprise lipid bilayers, as well as proteins for various functions. Localized concentrations of particular lipids may be found in the lipid bilayer, referred to as 'lipid rafts'. Without wishing to be bound by theory, lipid rafts may have significant roles in endo and exocytosis, entry or egress of viruses or other infectious agents, inter-cell signal transduction, interaction with other structural components of the cell or organism, such as intracellular and extracellular matrices.

The VLPs produced from influenza derived proteins, in accordance with the present invention do not comprise M1 protein. The M1 protein is known to bind RNA (Wakefield and Brownlee, 1989) which is a contaminant of the VLP preparation. The presence of RNA is undesired when obtaining regulatory approval for the VLP product, therefore a VLP preparation lacking RNA may be advantageous.

A VLP produced in a plant according to some aspects of the invention may be complexed with plant-derived lipids. The VLP may comprise an HA0, HA1 or HA2 peptide or combinations thereof. The plant-derived lipids may be in the form of a lipid bilayer, and may further comprise an envelope surrounding the VLP. The plant derived lipids may comprise lipid components of the plasma membrane of the plant where the VLP is produced, including, and one or more than one plant derived lipid, for example but not limited to phosphatidylcholine (PC), phosphatidylethanolamine (PE), glycosphingolipids, phytosterols or a combination thereof. A plant-derived lipid may alternately be referred to as a 'plant lipid'.

In plants, influenza VLPs bud from the plasma membrane, therefore the lipid composition of the VLPs reflects their origin. The VLPs produced according to the present invention comprise HA, complexed with plant derived lipids. Plant lipids can stimulate specific immune cells and enhance the immune response induced. Plant membranes are made of lipids, phosphatidylcholine (PC) and phosphatidylethanolamine (PE), and also contain glycosphingolipids, saponins, and phytosterols. Additionally, lipid rafts are also found in plant plasma membranes—these microdomains are enriched in sphingolipids and sterols. In plants, a variety of phytosterols are known to occur, including stigmasterol, sitosterol, 24-methylcholesterol and cholesterol (Mongrand et al., 2004).

PC and PE as well as glycosphingolipids can bind to CD1 molecules expressed by mammalian immune cells such as antigen-presenting cells (APCs) like dendritic cells and macrophages and other cells including B and T lymphocytes in the thymus and liver (Tsuji M,. 2006). CD1 molecules are structurally similar to major histocompatibility complex (MHC) molecules of class I and their role is to present glycolipid antigens to NKT cells (Natural Killer T cells). Upon activation, NKT cells activate innate immune cells such as NK cells and dendritic cells and also activate adaptive immune cells like the antibody-producing B cells and T-cells.

A variety of phytosterols may be found in a plasma membrane—the specific complement may vary depending on the species, growth conditions, nutrient resources or pathogen state, to name a few factors. Generally, beta-sitosterol is the most abundant phytosterol.

The phytosterols present in an influenza VLP complexed with a lipid bilayer, such as an plasma-membrane derived envelope may provide for an advantageous vaccine composition. Without wishing to be bound by theory, plant-made VLPs complexed with a lipid bilayer, such as a plasma-membrane derived envelope, may induce a stronger immune reaction than VLPs made in other expression systems, and may be similar to the immune reaction induced by live or attenuated whole virus vaccines.

Therefore, in some embodiments, the invention provides for a VLP complexed with a plant-derived lipid bilayer. In some embodiments the plant-derived lipid bilayer may comprise the envelope of the VLP.

8—Composition

Therefore, the present invention provides a composition comprising an effective dose of a VLP comprising an influenza virus HA protein, one or more than one plant lipid, and a pharmaceutically acceptable carrier. The influenza virus HA protein may be H5 Indonesia. Also provided is a method of inducing immunity to an influenza virus infection in a subject. The method comprising administering the virus like particle comprising an influenza virus HA protein, one or more than one plant lipid, and a pharmaceutically acceptable carrier. The virus like particle may be administered to a subject orally, intradermally, intranasally, intramuscularly, intraperitoneally, intravenously, or subcutaneously.

9—Method of Treatment

The present invention provides for a method of inducing immunity or "provoking an immune response" to an influenza virus infection in a subject, the method comprising administering the composition as defined herein.

An "immune response" generally refers to a response of the adaptive immune system. The adaptive immune system generally comprises a humoral response, and a cell-mediated response. The humoral response is the aspect of immunity that is mediated by secreted antibodies, produced in the cells of the B lymphocyte lineage (B cell). Secreted antibodies bind to antigens on the surfaces of invading microbes (such as viruses or bacteria), which flags them for destruction. Humoral immunity is used generally to refer to antibody production and the processes that accompany it, as well as the effector functions of antibodies, including Th2 cell activation and cytokine production, memory cell generation, opsonin promotion of phagocytosis, pathogen elimination and the like.

A cell-mediated response is an immune response that does not involve antibodies but rather involves the activation of macrophages, natural killer cells (NK), antigen-specific cytotoxic T-lymphocytes, and the release of various cytokines in response to an antigen. Cell-mediated immunity is used generally to refer to some Th cell activation, Tc cell activation and T-cell mediated responses. Cell mediated immunity is of particular importance in responding to viral infections.

The recombinant HA VLPs of the present invention can be used in conjunction with existing influenza vaccines, to supplement the vaccines, render them more efficacious, and to reduce the administration dosages necessary. As would be known to a person of skill in the art, the vaccine may be directed against one or more than one influenza virus. Examples of suitable vaccines include, but are not limited to those commercially available from Sanofi-Pasteur, ID Biomedical, Merial, Sinovac, Chiron, Roche, MedImmune, GlaxoSmithKline, Novartis, Sanofi-Aventis, Serono, Shire Pharmaceuticals and the like.

If desired, the VLPs of the present invention may be admixed with a suitable adjuvant as would be known to one of skill in the art. Furthermore, the VLP may be used in a vaccine composition comprising an effective dose of the VLP for the treatment of a target organism, as defined above. Furthermore, the VLP produced according to the present invention may be combined with VLPs obtained using different influenza proteins, for example, neuraminidase (NA).

Therefore, the present invention provides a method for inducing immunity to influenza virus infection in an animal or target organism comprising administering an effective dose of a vaccine comprising one or more than one VLP. The vaccine may be administered orally, intradermally, intranasally, intramuscularly, intraperitoneally, intravenously, or subcutaneously.

Figure 6:
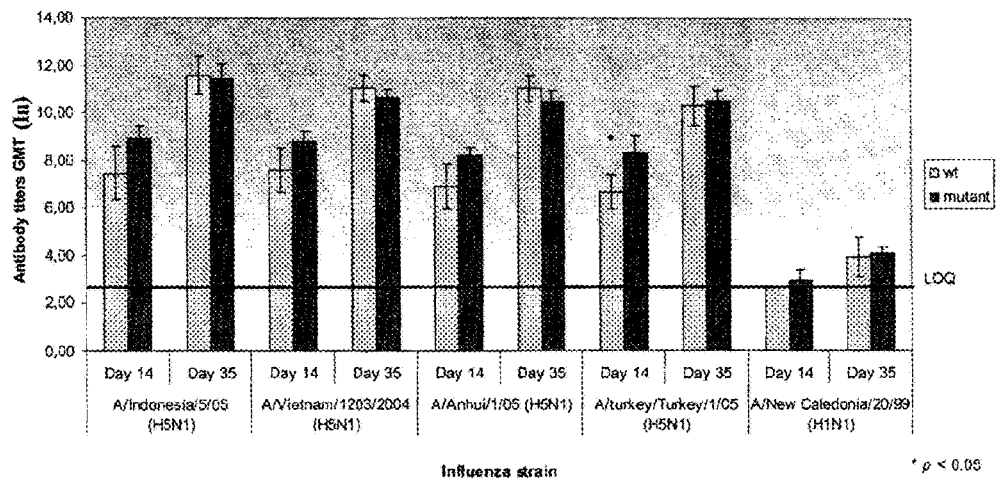
FIG. 6 shows antibody titers against Whole Inactivated Viruses (WIV) after first and second dose. The reactivity of sera from rats immunized with either the wt VLP or the triple mutant VLP (non-glycosylated) was assessed after the first (14 days) or the second immunization (35 days). Immunoreactivity was assessed against several H5N1 viruses.

As shown in FIGS. 6 and 7 in vitro assays showing cross-reactivity of antibodies raised against the mutated A/Indonesia/5/05 H5 VLPs and other influenza strains such as A/Vietnam/1203/04; A/Anhui/1/05 and A/Turkey/582/06 (all H5N1 strains), whereas it showed less hemagglutination reactivity against the only H1N1 tested (FIG. 7).

Significantly, the antibodies produced after a single dose of mutated H5N1 (unglycosylated H5 protein) induced a greater response against all H5 strains tested after 14 days than antibodies produced against the wild-type H5, indicating that this unglycosylated immunogen may provide more rapid response that the wild-type one.

These data, therefore, demonstrate that plant-made influenza VLPs comprising the mutated H5 hemagglutinin viral protein devoid of N-linked carbohydrates induce an immune response specific for pathogenic influenza strains, and that this response is cross-reactive and may be rapid after one single dose.

10—Subject

Examples of a subject or target organism that the VLPs of the present invention may be administered to include, but are not limited to, humans, primates, birds, water fowl, migratory birds, quail, duck, geese, poultry, turkey, chicken, swine, sheep, equine, horse, camel, canine, dogs, feline, cats, tiger, leopard, civet, mink, stone marten, ferrets, house pets, livestock, rabbits, mice, rats, guinea pigs or other rodents, seal, whale and the like. Such target organisms are exemplary, and are not to be considered limiting to the applications and uses of the present invention.

The present invention also pertains to influenza viruses which infect other mammals or host animals, for example humans, primates, horses, pigs, birds, avian water fowl, migratory birds, quail, duck, geese, poultry, turkey, chicken, camel, canine, dogs, feline, cats, tiger, leopard, civet, mink, stone marten, ferrets, house pets, livestock, mice, rats, seal, whale and the like.

Particularly, the subject being treated by the method as defined above may be selected from the group comprising humans, primates, horses, pigs, birds (avian) water fowl, migratory birds, quail, duck, geese, chicken, dogs, cats, ferrets, livestock and the like. Particularly, the subject may be a human patient or birds in general (including water fowl, migratory birds, poultry such as quail, duck, geese, turkey, chicken), particularly migratory birds or poultry for human consumption (quail, duck, geese, turkey, chicken). More particularly, the subject is human.

11—Containers, Syringes, and Kits Etc.

The present invention also provides for a container comprising the composition as defined herein. Particularly, the container contains single unit dose or in multiple dosage form with a preservative agent. More particularly, the container is a syringe "ready-for-use" pre-filled with the composition or the vaccine as defined herein.

More particularly, the invention also provides for a kit comprising a container comprising the vaccine or composition as defined herein, and instructions on how to use/administer said composition/vaccine.

The invention will now be described in detail by way of reference only to the following non-limiting examples.

Example 1

Material and Methods

1. Mutation of Wild-Type H5 from A/Indonesia/5/05 (SEQ ID NO.17) to obtain Mutated Unglycosylated H5.

Figure 4:
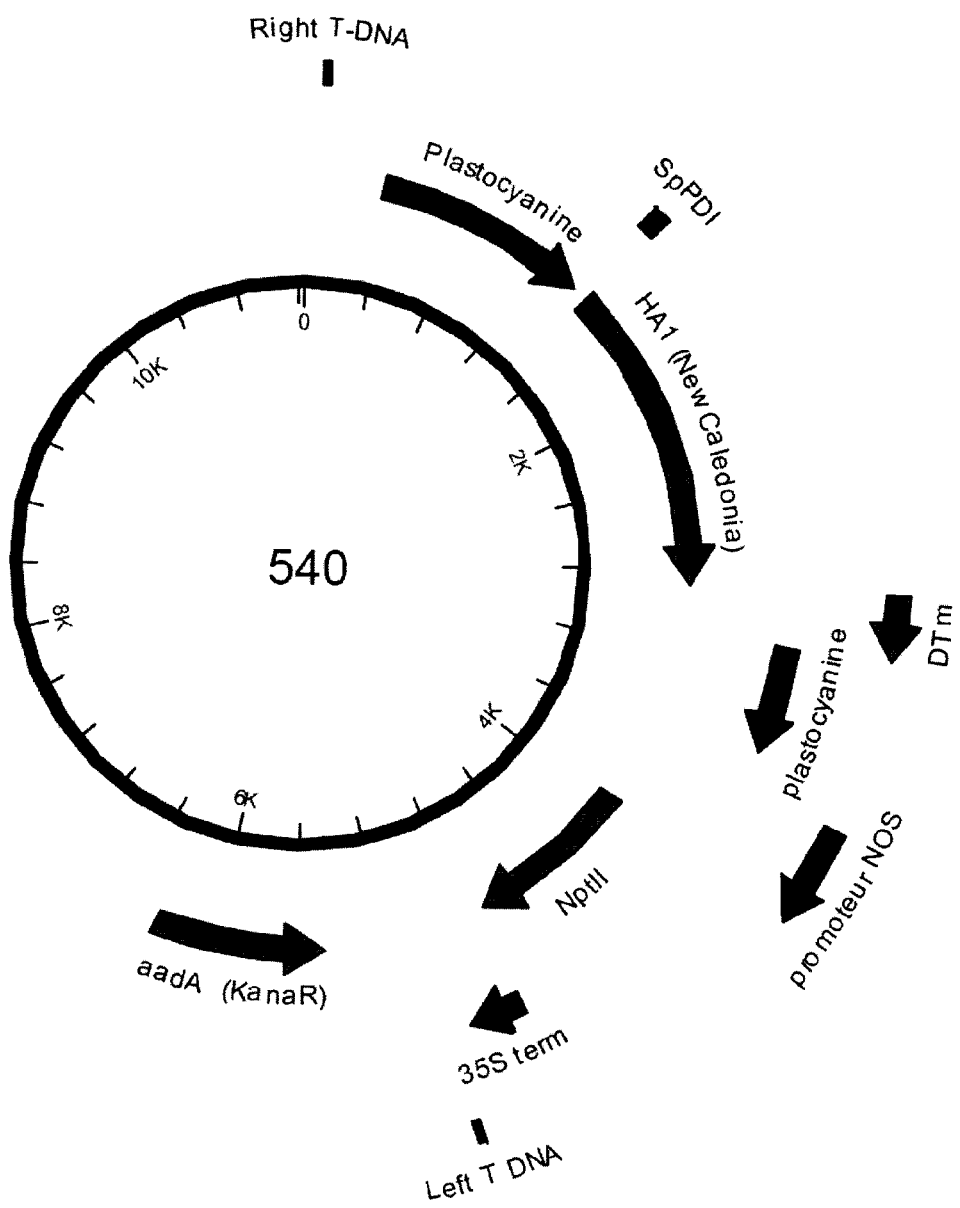
FIG. 4 shows a representation of plasmid 660 assembled for the expression of wild-type HA subtype H5 from A/Indonesia/5/05.

The triple mutant has been made by removing the glycosylation sites N1 54, N165, and N286 located on the globular head of wild type HAs, more specifically by replacing the Thr or Ser enclosed in the glycosylation sequence pattern N-X-T/S by an Ala residue. Therefore, the triple mutant contained the following three amino acid replacements: T156A, T167A and S288A (numbered according to the starting SEQ ID NO.34). The three amino acid replacement were performed by PCR-based ligation method presented in Darveau et al. (1995) using the wild type HA expression vector (660 construct, FIG. 4) as the template.

Briefly, three PCR amplification were performed in parallel on 660 pCAMBIA expression vector as the template with 3 different pairs of primers:

1) Plato-443c (SEQ ID NO: 18) and HA5-T156A.r (SEQ ID NO:19);

2) HA5-T167A.c (SEQ ID NO:20) and HA5-S288A.r (SEQ ID NO: 21); and

3) HA5-S288A.c (SEQ ID NO:22) and HA(Ind)-SacI.r (SEQ ID NO: 23).

Figure 5:
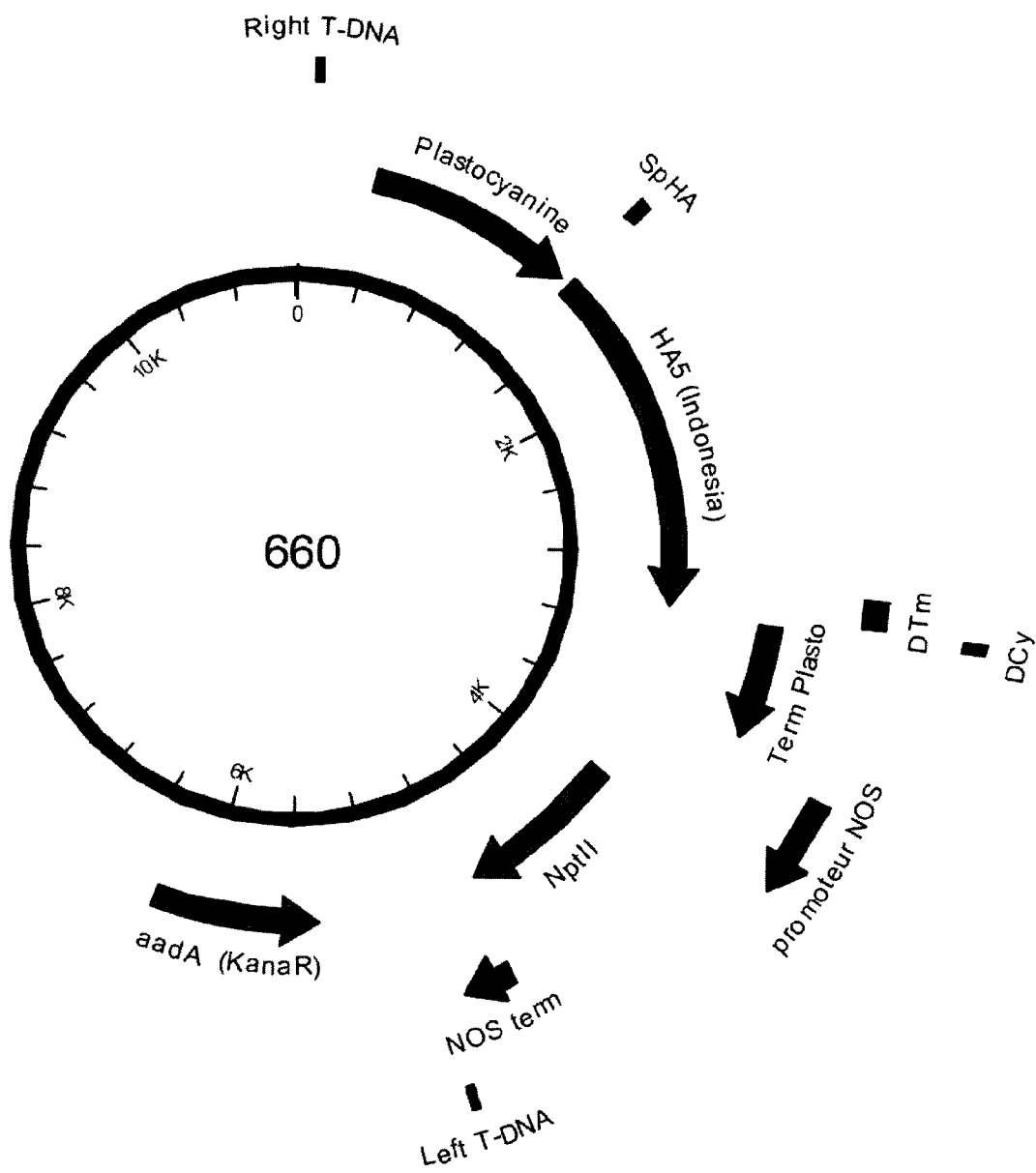
FIG. 5 shows a representation of plasmid 680 assembled for the expression of unglycosylated mutated HA subtype H5 from A/Indonesia/5/05.

The amplification products obtained from the three reactions were mixed together and the mixture served as template for a fourth reaction (assembling reaction) using Plato-443c (SEQ ID NO: 18) and HA(Ind)-Sac.r (SEQ ID NO: 23) as primers. The resulting fragment was digested with BamHI (located in the plastocyanin promoter) and SacI (at the 3' end of the fragment) and cloned into pCAMBIAPlasto previously digested with the same enzymes. The resulting plasmid, named 680, is presented in FIG. 5 (SEQ ID NO.29).

2. Assembly of Expression Cassettes

All manipulations were carried out using the general molecular biology protocols of Sambrook and Russell (2001; which is incorporated herein by reference). The first cloning step consisted in assembling a receptor plasmid containing upstream and downstream regulatory elements of the alfalfa plastocyanin gene. The plastocyanin promoter and 5'UTR sequences were amplified from alfalfa genomic DNA using oligonucleotide primers XmaI-pPlas.c (SEQ ID NO: 24) and SacI-ATG-pPlas.r (SEQ ID NO: 25). The resulting amplification product was digested with XmaI and SacI and ligated into pCAMBIA2300 (Cambia, Can berra, Australia), previously digested with the same enzymes, to create pCAMBIApromo Plasto. Similarly, the 3'UTR sequences and terminator of the plastocyanin gene was amplified from alfalfa genomic DNA using the following primers: SacI-PlasTer.c (SEQ ID NO: 26) and EcoRI-Plas-Ter.r (SEQ ID NO: 27), and the product was digested with SacI and EcoRI before being inserted into the same sites of pCAMBIApromoPlasto to create pCAMBIAPlasto.

3. Assembly of H5 Expression Cassette

A fragment encoding hemagglutinin from influenza strain A/Indonesia/5/05 (H5N1; Acc. No. LANL ISDN125873) was synthesized by Epoch Biolabs (Sugar Land, Tex., USA). The fragment produced, containing the complete H5 coding region (SEQ ID NO.17) including the native signal peptide flanked by a HindIII site immediately upstream of the initial ATG, and a SacI site immediately downstream of the stop (TAA) codon, is presented in SEQ ID NO: 28 (and SEQ ID NO.29 in the case of the mutant H5). The H5 coding region was cloned into a plastocyanin-based expression cassette by the PCR-based ligation method presented in Darveau et al. (1995). Briefly, a first PCR amplification was obtained using primers Plato-443c (SEQ ID NO: 30) and SpHA(Ind)-Plastos (SEQ ID NO:31) and pCAMBIA promoPlasto as template. In parallel, a second amplification was performed with primers Plasto-SpHA(Ind).c (SEQ ID NO: 6) and HA(Ind)-Sac.r (SEQ ID NO:32) with H5 coding fragment as template. The amplification obtained from both reactions were mixed together and the mixture served as template for a third reaction (assembling reaction) using Plato-443c (SEQ ID NO: 4) and HA(Ind)-Sac.r (SEQ ID NO: 33) as primers. The resulting fragment was digested with BamHI (in the plastocyanin promoter) and SacI (at the 3' end of the fragment) and cloned into pCAMBIAPlasto previously digested with the same enzymes. The resulting plasmid, named 660, is presented in FIG. 5 whereas the plasmid resulting from the "mutated" H5 protein was named 680.

An HcPro construct (35HcPro) was prepared as described in Hamilton et al. (2002). All clones were sequenced to confirm the integrity of the constructs. The plasmids were used to transform *Agrobacterium tumefaciens* (AGL1; ATCC, Manassas, Va. 20108, USA) by electroporation (Mattanovich et al., 1989). The integrity of all *A. tumefaciens* strains were confirmed by restriction mapping.

4. Preparation of Plant Biomass, Inoculum, Agroinfiltration, and Harvesting

*Nicotiana benthamiana* plants were grown from seeds in flats filled with a commercial peat moss substrate. The plants were allowed to grow in the greenhouse under a 16/8 photoperiod and a temperature regime of 25° C. day/20° C. night. Three weeks after seeding, individual plantlets were picked out, transplanted in pots and left to grow in the greenhouse for three additional weeks under the same environmental conditions. Prior to transformation, apical and axillary buds were removed at various times as indicated below, either by pinching the buds from the plant, or by chemically treating the plant

*Agrobacteria* transfected with plasmids 660 or 680 were grown in a YEB medium supplemented with 10 mM 2-[N-morpholino]ethanesulfonic acid (MES), 20 μM acetosyringone, 50 μg/ml kanamycin and 25 μg/ml of carbenicillin pH5.6 until they reached an OD600 between 0.6 and 1.6. *Agrobacterium* suspensions were centrifuged before use and resuspended in infiltration medium (10 mM MgCl2 and 10 mM MES pH 5.6). Syringe-infiltration was performed as described by Liu and Lomonossoff (2002, Journal of Virological Methods, 105:343-348). For vacuum-infiltration, *A. tumefaciens* suspensions were centrifuged, resuspended in the infiltration medium and stored overnight at 4° C. On the day of infiltration, culture batches were diluted in 2.5 culture volumes and allowed to warm before use. Whole plants of *Nicotiana benthamiana* were placed upside down in the bacterial suspension in an air-tight stainless steel tank under a vacuum of 20-40 Torr for 2-min. Following syringe or vacuum infiltration, plants were returned to the greenhouse for a 4-5 day incubation period until harvest.

5. Leaf Sampling and Total Protein Extraction

Following incubation, the aerial part of plants was harvested, frozen at −80° C., crushed into pieces. Total soluble proteins were extracted by homogenizing (Polytron) each sample of frozen-crushed plant material in 3 volumes of cold 50 mM Tris pH 7.4, 0.15 M NaCl, and 1 mM phenylmethanesulfonyl fluoride. After homogenization, the slurries were centrifuged at 20,000 g for 20 min at 4° C. and these clarified crude extracts (supernatant) kept for analyses. The total protein content of clarified crude extracts was determined by the Bradford assay (Bio-Rad, Hercules, Calif.) using bovine serum albumin as the reference standard.

6. Protein Analysis and Immunoblotting

Protein concentrations were determined by the BCA protein assay (Pierce Biochemicals, Rockport Ill.). Proteins were separated by SDS-PAGE under reducing conditions and stained with Coomassie Blue. Stained gels were scanned and densitometry analysis performed using ImageJ Software (NIH).

Proteins from elution fraction from SEC were precipitated with acetone (Bollag et al., 1996), resuspended in ⅕ volume in equilibration/elution buffer and separated by SDS-PAGE under reducing conditions and electrotransferred onto polyvinylene difluoride (PVDF) membranes (Roche Diagnostics Corporation, Indianapolis, Ind.) for immunodetection. Prior to immunoblotting, the membranes were blocked with 5% skim milk and 0.1% Tween-20 in Tris-buffered saline (TBS-T) for 16-18 h at 4° C.

Immunoblotting was performed by incubation with the following antibodies: for the detection of H1, a mouse anti-influenza A monoclonal antibody (Fitzgerald Industries International, Concord, Mass., USA, Cat. No. 10-150) (2 μg/ml in 2% skim milk in TBS-Tween 20 0.1%), and for the detection of H5, a rabbit anti-H5 (Vietnam) antibody (Immune Technology, Woodside, N.Y., USA, Cat No. IT-003-005V) diluted 1/4000 in 2% skim milk in TBS-Tween 20 0.1%. A peroxidase-conjugated goat anti-mouse IgG (H+L) antibody (Jackson Immunoresearch Laboratories, West Grove, Pa., USA, Cat. No. 115-035-146) (diluted 1/12 000 in 2% skim milk in TBS-Tween 20 0.1%) was used as secondary antibody. Immunoreactive complexes were detected by chemiluminescence using luminol as the substrate (Roche Diagnostics Corporation). Horseradish peroxidase-enzyme conjugation of human IgG antibody was carried out by using the EZ-Link Plus® Activated Peroxidase conjugation kit (Pierce, Rockford, Ill.).

Hemagglutination assay for H5 was based on a method described by Nayak. and Reichl (2004). Briefly, serial double dilutions of the test samples (100 μl) were made in V-bottomed 96-well microtiter plates containing 100 μL PBS, leaving 100 μL of diluted sample per well. One hundred microliters of a 0.25% horse red blood cells suspension (Bio Link Inc., Syracuse, N.Y.) were added to each well, and plates were incubated for 2 h at room temperature. The reciprocal of the highest dilution showing complete hemagglutination was recorded as HA activity. In parallel, a recombinant HA standard (A/Vietnam/1203/2004 H5N1) (Protein Science Corporation, Meriden, Conn.) was diluted in PBS and run as a control on each plate.

7. H5 VLP Purification

Frozen 660- or 680-infiltrated leaves of *N. benthamiana* were homogenized in 1.5 volumes of 50 mM Tris pH 8, NaCl 50 mM and 0.04% sodium meta-bisulfite using a commercial blender. The resulting extract was supplemented with 1 mM PMSF and adjusted to pH 6 with 1 M acetic acid before being heated at 42° C. for 5 min. Diatomaceous earth (DE) was added to the heat-treated extract to adsorb the contaminants precipitated by the pH shift and heat treatment, and the slurry was filtered through a Whatman paper filter. The resulting clarified extract was centrifuged at 10,000×g for 10 minutes at RT to remove residual DE, passed through 0.8/0.2 μM Acropack 20 filters and loaded onto a fetuin-agarose affinity column (Sigma-Aldrich, St-Louis, Mo., USA). Following a wash step in 400 mM NaCl, 25 mM Tris pH 6, bound proteins were eluted with 1.5 M NaCl, 50 mM MES pH 6. Eluted VLP were supplemented with Tween-80 to a final concentration of 0.0005% (v/v). VLP were concentrated on a 100 kDa MWCO Amicon membrane, centrifuged at 10,000×g for 30 minutes at 4° C. and resuspended in PBS pH 7.4 with 0.01% Tween-80 and 0.01% thimerosal. Suspended VLPs were filter-sterilized before use.

8. Animal Studies

Studies on the immune response to influenza VLP administration were performed with 6-8 week old female Wistar rats (Charles River Laboratories). Thirteen rats were randomly divided into three groups ranging from three for the control group to five animals for both the plant-made VLP H5 wild type vaccine (660) and the mutant (680) vaccine groups. Eight groups were used for intramuscular immunization and six groups were used to test intranasal route of administration. All groups were immunized in a two-dose regiment, the boost immunization being done 14 days following the first immunization.

For intramuscular administration in hind legs, unanaesthetized rats were immunized with either the plant-made VLP H5 vaccine (15 μg), the plant-made VLP H5 mutant form of the vaccine or PBS.

All antigen preparations were mixed with Alhydrogel to a final concentration of 1% (alum; Accurate Chemical and Scientific Corporation, Wesbury, N.Y., US) in a 1:1 volume ratio prior to immunizations.

Blood Collection and Spleen Collection

Jugular vein blood collection was performed fourteen days after the first immunization and fourteen days after second immunization on anaesthetized animal. Serum was collected by centrifuging at 8000 g for 10 min.

Three weeks after second immunisation, rats were anaesthetized with CO2 gas and immediately upon termination, cardiac puncture was used to collect blood.

Spleen collection was performed on rats Collected spleens were placed in RPMI supplemented with gentamycin and mashed in a 50 ml conical tube with plunger from a 10 ml syringe. Mashed spleens were rinsed 2 times and centrifuged at 2000 rpm for 5 min and resuspended in ACK lysing buffer for 5 min at room temperature. The splenocytes were washed in PBS-gentamycin, resuspended in 5% RPMI and counted. Splenocytes were used for proliferation assay.

Antibody Titers:
A/Vietnam/1203/2004 (H5N1); A/Anhui/1/05 (H5N1); A/turkey/Turkey/1/05 (H5N1);
A/New Calcdonia/20/99 (H1N2

Anti-influenza antibody titers of sera were measured at 14 days after the first immunization as well as 21 days after the second immunisation (at sacrifice). The titers were determined by enzyme-linked immunosorbent assay (ELISA) using the inactivated virus A/Indonesia/5/05 as the coating antigen. The end-point (titers were expressed as the reciprocal value of the highest dilution that reached an OD value of at least 0.1 higher than that of negative control samples.

For antibody class determination (IgG1, IgG2a, IgG2b, IgG3, IgM), the titers were evaluated on final bleeding by ELISA as previously described.

Hemagglutination Inhibition (HI) Titers

Hemagglutination inhibition (HI) titers of sera were measured at days 14 and 35 after the second immunisation as previously described (WHO 2002; Kendal 1982). Inactivated virus preparations from strains A/Indonesia/5/05; A/Anhui/1/05 (H5N1); A/turkey/Turkey/1/05 (H5N1) or A/Vietnam/1203/2004 were used to test rat serum samples for HI activity. Sera were pre-treated with receptor-destroying enzyme II (RDE II) (Denka Seiken Co., Tokyo, Japan) prepared from *Vibrio cholerae* (Kendal 1982). HI assays were performed with 0.5% horse red blood cells. HI antibody titres were defined as the reciprocal of the highest dilution causing complete inhibition of agglutination.

Results

The reactivity of the sera from rats immunized with either the wt VLP or the mutant VLP was assessed 14 days after the first (Day 14) or the second immunization (Day 35). All rats were immunized with 15 μg of the antigen formulated with alum. Immunoreactivity was assessed against H5N1 viruses of clade 1 (A/Vietnam/1203/04), clade 2.1 (A/Indonesia/5/05), clade 2.2 (A/turkey/Turkey/1/05) and clade 2.3 (A/Anhui/1/05). After the first dose, the mutant VLP induced a higher antibody reaction than the wt for all H5N1 strains tested (FIG. 6). The immunoreactivity against the avian strain A/turkey/Turkey/1/05 was statistically significant (p<0.05) after the first dose. Immunoreactivity was also assessed against H1N1 viruses (A/New Calcdonia/20/99) showing immunoreactivity after boost injection. GMT: geometric mean titer. Values are the GMT (ln) of reciprocal end-point titers of five rats per group. Bars represent mean deviation. *p<0.05 compared to the wt VLP HI titers from rats immunized with the wt or the mutant VLP were assessed 14 days after the first (Day 14) or the second (Day 35) immunization. HI antibody responses were measured using inactivated whole H5N1 viruses. After the first immunization, the mutant VLP induces a higher HI antibody response than the wt VLP against all H5N1 viruses tested (FIG. 7). Statistical significance was reached for A/Indonesia/5/05 and A/turkey/Turkey/1/05 influenza strains. GMT: geometric mean titer. Values are the GMT (ln) of reciprocal end-point titers of five rats per group. Bars represent mean deviation. *p<0.05 and compared to wt VLP.

These data strongly suggest that the "mutated" unglycosylated H5 protein represents a very interesting alternative to the native H5 protein for the production of VLPs as broad-spectrum and fast-active flu vaccine.

All citations are hereby incorporated by reference.

The present invention has been described with regard to one or more particular embodiments. However, it will be apparent to persons skilled in the art that a number of variations and modifications can be made without departing from the scope of the invention as defined in the claims.

REFERENCES

Abe Y. et al. *Journal of virology*. (2004) 78: 9605-9611.

Bollag, D. M., Rozycki, M. D., and Edelstein, S. J. (1996) *Protein methods* ($2^{nd}$ edition). Wiley-Liss, New York, USA.

Bligh, E. G., & Dyer, W. J. *Can. J. Med. Sci.* 37, 911-917 (1959).

Bright et al. *Virology*. (2003) 308: 270-278.

Chen, B. J., Leser, G. P., Morita, E., and Lamb R. A. (2007) Influenza virus hemagglutinin and neuraminidase, but not the matrix protein, are required for assembly and budding of plasmid-derived virus-like particles. J. Virol. 81, 7111-7123.

Crawford, J., Wilkinson, B., Vosnesensky, A., Smith, G., Garcia, M., Stone, H., and Perdue, M. L. (1999). Baculovirus-derived hemagglutinin vaccines protect against lethal influenza infections by avian H5 and H7 subtypes. Vaccine 17, 2265-2274.

Darveau, A., Pelletier, A. & Perreault, J. PCR-mediated synthesis of chimeric molecules. *Methods Neurosc.* 26, 77-85 (1995).

Grgacic E V L, Anderson D A. Virus-like particles: passport to immune recognition. Methods 2006; 40: 60-65.

Gillim-Ross, L., and Subbarao, K. (2006) Emerging respiratory viruses: challenges and vaccine strategies. Clin. Microbiol. Rev. 19, 614-636.

Gomez-Puertas, P., Mena, I., Castillo, M., Vivo, A., Perez-Pastrana, E. and Portela, A. (1999) Efficient formation of influenza virus-like particles: dependence on the expression level of viral proteins. J. Gen. Virol. 80, 1635-1645.

Gomez-Puertas, P., Albo, C., Perez-Pastrana, E., Vivo, A., and Portela, A. (2000) Influenza Virus protein is the major driving force in virus budding. J. Virol. 74, 11538-11547.

Hamilton, A., Voinnet, O., Chappell, L. & Baulcombe, D. Two classes of short interfering RNA in RNA silencing. *EMBO J.* 21, 4671-4679 (2002).

Höfgen, R. & Willmitzer, L. Storage of competent cells for *Agrobacterium* transformation. *Nucleic Acid Res.* 16, 9877 (1988).

Harbury P B, Zhang T, Kim P S, Alber T. (1993) A switch between two-, three-, and four-stranded coiled coils in GCN4 leucine zipper mutants. Science; 262: 1401-1407)

Horimoto T., Kawaoka Y. Strategies for developing vaccines against h5N1 influenza a viruses. Trends in Mol. Med. 2006; 12(11):506-514.

Huang Z, Elkin G, Maloney B J, Beuhner N, Arntzen C J, Thanavala Y, Mason H S. Virus-like particle expression and assembly in plants: hepatitis B and Norwalk viruses. Vaccine. 2005 Mar. 7; 23(15):1851-8.

Johansson, B. E. (1999). Immunization with influenza A virus hemagglutinin and neuraminidase produced in recombinant baculovirus results in a balanced and broadened immune response superior to conventional vaccine. Vaccine 17, 2073-2080.

Kapila, J., De Rycke, R., Van Montagu, M. & Angenon, G. An *Agrobacterium*-mediated transient gene expression system for intact leaves. *Plant Sci.* 122, 101-108 (1997).

Kuroda et al. (1990) *Virology*. 174: 418-429.

Latham, T., and Galarza, J. M. (2001). Formation of wild-type and chimeric influenza virus-like particles following simultaneous expression of only four structural proteins. J. Virol. 75, 6154-6165.

Lefebvre, B. et al. *Plant Physiol.* 144, 402-418 (2007).

Liu, L & Lomonossoff, G. P. Agroinfection as a rapid method for propagating Cowpea mosaic virus-based constructs. *J. Virol. Methods* 105, 343-348 (2002).

Macala, L. J., Yo, R. K. & Ando, S. *J Lipid Res.* 24, 1243-1250 (1983)

Mattanovich, D., Rüker, F., da Câmara Machado, A., Laimer, M., Regner, F., Steinkellner, H., Himmler, G., and Katinger, H. (1989) Efficient transformation of *Agrobacterium* spp. By electroporation. *Nucl. Ac. Res.* 17, 6747.

Mena, I., Vivo, A., Perez, E., and Portela, A. (1996) Rescue of synthetic chloramphenicol acetyltransferase RNA into influenza virus-like particles obtained from recombinant plasmids. J. Virol. 70, 5016-5024.

Mongrand S, Morel J, Laroche J, Clayerol S, Carde J P, Hartmann M A et al. Lipid rafts in higher plant cells. The Journal of Biological Chemistry 2004; 279(35): 36277-36286.

Neumann, G., Watanabe, T., and Kawaoka, Y. (2000) Plasmid-driven formation of virus-like particles. J. Virol. 74, 547-551.

Nayak D P, Reichl U. (2004) Neuraminidase activity assays for monitoring MDCK cell culture derived influenza virus. J Virol Methods 122(1):9-15.

Olsen, C. W., McGregor, M. W., Dybdahl-Sissoko, N., Schram, B. R., Nelson, K. M., Lunn, D., Macklin, M. D., and Swain, W. F. (1997). Immunogenicity and efficacy of baculovirus-expressed and DNA-based equine influenza virus hemagglutinin vaccines in mice. Vaccine 15, 1149-1156.

Quan F S, Huang C, Compans R W, Kang S M. Virus-like particle vaccine induces protective immunity against homologous and heterologous strains of influenza virus. Journal of Virology 2007; 81(7): 3514-3524.

Saint-Jore-Dupas C, Faye L, Gomord V. (2007) From plants to pharma with glycosylation in the toolbox. Trends in biotech, 25(7) 317-323.

Sambrook J, and Russell D W. Molecular cloning: a laboratory manual. Cold Spring Harbor, N.Y. Cold Spring Harbor Laboratory Press, 2001.

Suzuki, Y. (2005) Sialobiology of influenza. Molecular mechanism of host range variation of influenza viruses. Biol. Pharm. Bull 28, 399-408.

Tsuji M., Cell. Mol. Life. Sci., 63 (2006); 1889-1898.

Vigerust D J et al. *Journal of virology*. (2007) 81: 8593-8600.

Wakefield L., G. G. Brownlee Nuc Acid Res. 17 (1989); 8569-8580.

Kendal, A P, Pereira Miss., Skehel J. Concepts and procedures for laboratory-based influenza surveillance. Atlanta: CDC; 1982. p. B17-B35.

WHO. Manual on animal influenza diagnosis and surveillance. Department of communicable disease surveillance and response. World Health Organisation Global Influenza Program. 2002.

The invention claimed is:

1. A method of producing influenza virus like particles (VLPs) in a plant, a portion thereof, or a plant cell, said method comprising:
   a) introducing by agroinfiltration into the plant, the portion thereof, or the plant cell a nucleic acid comprising a nucleotide sequence having from 90% to 100% identity to SEQ ID NO: 17, the nucleotide sequence encoding an influenza virus hemagglutinin (HA) comprising a HA1 domain, wherein said HA1 domain is modified to be free of N-linked glycosylation sites at positions 154 and/or 156; at positions 165 and/or 167; and at positions 286 and/or 288, wherein at least one of positions 154, 165, or 286 are modified to be an amino acid other than asparagine, or at least one of positions 156, 167, or 288 are modified to be an alanine or an amino acid other than serine, or threonine, wherein the numbering of said positions are compared to SEQ ID NO: 34 wherein the nucleotide sequence is operatively linked to a nucleic acid sequence encoding a signal peptide and a regulatory region active in the plant, the portion thereof, or the plant cell; and wherein the HA has hemagglutinin activity as determined by using a hemagglutination assay;

b) incubating the plant, the portion thereof, or the plant cell under conditions that permit expression of the nucleic acid, thereby producing said VLPs, wherein the nucleic acid is transiently expressed in the plant, the portion thereof, or the plant cell;

c) harvesting the plant, the portion thereof, or the plant cell; and d) purifying the VLPs, wherein the VLPs are characterized as not passing through a 100 kDa membrane.

2. A virus like particle (VLP) produced by the method of claim 1.

3. The virus like particle (VLP) of claim 2 comprising an influenza virus hemagglutinin (HA) and one or more than one plant lipid.

4. The VLP according to claim 2 for use as a vaccine for the prevention or treatment of a viral infection in a subject.

5. A composition comprising an effective dose of a VLP according to claim 2, in admixture with a pharmaceutically acceptable carrier.

6. A method of inducing immunity to an influenza virus infection in a subject, the method comprising administering the VLP according to claim 2, and a pharmaceutically acceptable carrier.

7. A plant or plant cell that has been produced according to the method of claim 1.

8. The method of claim 1, wherein said nucleotide sequence encodes an influenza virus hemagglutinin (HA) comprising SEQ ID NO: 34, wherein each residue at amino acid positions 154, 165, and 286 is an amino acid other than asparagine.

9. The method of claim 1, wherein said nucleotide sequence encodes an influenza virus hemagglutinin (HA) comprising SEQ ID NO: 34, wherein residues at amino acid positions 156, 167, and 288 are each selected from the group consisting of alanine, an amino acid other than serine, and an amino acid other than threonine.

10. The method of claim 1, wherein the nucleotide sequence has from 90% to 100% identity to the sequence of SEQ ID NO. 29 whereby residues encoding amino acids 154, 165 and 286 are identical to those of SEQ ID NO. 29.

11. The VLP according to claim 2, wherein said influenza virus is of type A or type B.

12. The VLP according to claim 11, wherein said HA is from one or more than one A subtype selected from the group consisting of: H1, H2, H3, H4, H5, H6, H7, H8, H9, H10, H11, H12, H13, H14, H15 and H16.

13. The method of claim 1, wherein said regulatory region is selected from the group consisting of: plastocyanin regulatory region; napin promoter, the cruciferin promoter, or a regulatory region obtained from Ribulose 1,5 bisphosphate carboxylase/oxygenase (RuBisCO), chlorophyll a/b binding protein, ST-LS1 gene promoter from *Solanum tuberosum*, polyhedron promoter, and the gp64 promoter.

14. The method of claim 1, wherein said plastocyanin regulatory region is from alfalfa (*Medicago sativa*).

15. The method of claim 1, wherein the nucleotide sequence is as defined according to SEQ ID NO. 29.

16. The method of claim 1, wherein the nucleotide sequence has 90% identity to SEQ ID NO. 29, whereby residues encoding amino acids 154, 165 and 286 are identical to those of SEQ ID NO. 29.

17. The method of claim 1, wherein amino acids at positions 154, 165 or 286 are selected from the group consisting of Leu, Ile, Val, Thr, Ser and Ala.

18. The method of claim 1, wherein amino acids at positions 156, 167 or 288 are selected from the group consisting of Ala, Val, Ile and Leu.

19. The method of claim 1, wherein the nucleotide sequence is as defined according to SEQ ID NO. 29.

20. The method of claim 1, wherein amino acids at positions 154, 165 or 286 are selected from the group consisting of Leu, Ile, Val, Thr, Ser and Ala.

21. The method of claim 1, wherein amino acids at positions 156, 167 or 288 are selected from the group consisting of Ala, Val, Ile and Leu.

22. The method of claim 6, wherein the VLP is administered to the subject once as a single dose.

23. The method of claim 1, wherein the VLP does not comprise neuraminidase (NA).

* * * * *

UNITED STATES PATENT AND TRADEMARK OFFICE
CERTIFICATE OF CORRECTION

PATENT NO. : 9,546,375 B2  Page 1 of 1
APPLICATION NO. : 13/054452
DATED : January 17, 2017
INVENTOR(S) : Manon Couture, Louis-Philippe Vezina and Nathalie Landry It is certified that error appears in the above-identified patent and that said Letters Patent is hereby corrected as shown below:

Column 10, Line 19, "cytoplasic" should be --cytoplasmic--.

Column 12, Line 66, "oft-DNA" should be --of t-DNA--.

Column 21, Line 51, "Calcdonia" should be --Caledonia--.

Column 21, Line 62, "Calcdonia" should be --Caledonia--.

Column 21, Line 66, "Calcdonia" should be --Caledonia--.

Column 27, Line 9, "Can berra" should be --Canberra--.

Column 27, Line 17, "pCAMBIAPIasto" should be --pCAMBIAPlasto--.

Column 27, Line 32, "Plastos" should be --Plasto.r--.

Column 30, Line 6, "Calcdonia" should be --Caledonia--.

Column 30, Line 44, "Calcdonia" should be --Caledonia--.

Signed and Sealed this
Twenty-fifth Day of July, 2017

Joseph Matal
*Performing the Functions and Duties of the*
*Under Secretary of Commerce for Intellectual Property and*
*Director of the United States Patent and Trademark Office*